(12) United States Patent
Monga et al.

(10) Patent No.: US 12,180,474 B2
(45) Date of Patent: *Dec. 31, 2024

(54) METHODS OF TREATING PORPHYRIA

(71) Applicant: University of Pittsburgh—Of the Commonwealth System of Higher Education, Pittsburgh, PA (US)

(72) Inventors: Satdarshan Monga, Wexford, PA (US); Kari Nejak-Bowen, Wexford, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 883 days.

This patent is subject to a terminal disclaimer.

(21) Appl. No.: 17/194,706

(22) Filed: Mar. 8, 2021

(65) Prior Publication Data

US 2021/0222172 A1 Jul. 22, 2021

Related U.S. Application Data

(63) Continuation of application No. 16/509,734, filed on Jul. 12, 2019, now Pat. No. 10,961,534.

(60) Provisional application No. 62/697,548, filed on Jul. 13, 2018.

(51) Int. Cl.
| | |
|---|---|
| *C12N 15/113* | (2010.01) |
| *A61K 31/444* | (2006.01) |
| *A61K 31/519* | (2006.01) |
| *A61P 1/16* | (2006.01) |

(52) U.S. Cl.
CPC .......... *C12N 15/113* (2013.01); *A61K 31/444* (2013.01); *A61K 31/519* (2013.01); *A61P 1/16* (2018.01); *C12N 2310/14* (2013.01)

(58) Field of Classification Search
CPC ..... A61P 1/16; C12N 15/113; C12N 2310/14; C12N 2320/30; A61K 31/444; A61K 31/519
USPC ......... 435/6.1, 91.1, 91.31, 455, 458; 514/1, 514/44 A; 536/23.1, 24.5
See application file for complete search history.

(56) References Cited

U.S. PATENT DOCUMENTS

| | | |
|---|---|---|
| 6,066,500 A | 5/2000 | Bennett et al. |
| 8,293,743 B2 | 10/2012 | Kahn |
| 8,546,396 B2 | 10/2013 | Cheng et al. |
| 9,783,550 B2 | 10/2017 | Lum et al. |
| 9,926,320 B2 | 3/2018 | Ho et al. |
| 10,047,079 B2 | 8/2018 | Bhamra et al. |
| 10,202,375 B2 | 2/2019 | Bhamra et al. |
| 10,238,652 B2 | 3/2019 | An |
| 10,961,534 B2 * | 3/2021 | Monga ................ A61K 31/519 |
| 2016/0186176 A1 | 6/2016 | Brown et al. |
| 2018/0153884 A1 | 6/2018 | Qin et al. |

FOREIGN PATENT DOCUMENTS

WO 2014165232 A1 10/2014

OTHER PUBLICATIONS

Singla et al., "Oxidative stress, Nrf2 and keratin upregulation associate with Mallory-Denk body formation in mouse erythropoietic protoporphyria" Hepatology, 2012, pp. 322-331, vol. 56.
Smith et al., "Drugs and the hepatic porphyrias", Clinics in Haematology, 1980, pp. 399-425, vol. 9.
Tan et al., "Conditional deletion of beta-catenin reveals its role in liver growth and regeneration", Gastroenterology, 2006, pp. 1561-1572, vol. 131.
Tao et al., "Wnt/beta-catenin signaling protects mouse liver against oxidative stress-induced apoptosis through the inhibition of forkhead transcription factor FoxO3", J Biol Chem, 2013, pp. 17214-17224, vol. 288, No. 24.
Tephly et al., "Studies on the mechanism of experimental porphyria and ferrochelatase inhibition produced by 3,5-diethoxycarbonyl-1,4-dihydrocollidine", Int J Biochem, 1980, pp. 993-998, vol. 12.
Thomas et al. "Genome-wide tissue-specific farnesoid X receptor binding in mouse liver and intestine", Hepatology, 2010, pp. 1410-1419, vol. 51, No. 4.
Thompson et al., "beta-catenin regulation of farnesoid X receptor signaling and bile acid metabolism during murine cholestasis.", Hepatology, 2018, pp. 955-971, vol. 67, No. 3.
Thompson et al., "Spontaneous repopulation of beta-catenin null livers with beta-catenin positive hepatocytes after chronic murine liver injury", Hepatology, 2011, pp. 1333-1343, vol. 54, No. 4.
Vargas et al. "Detection of c-type cytochromes using enhanced chemiluminescence", Anal Biochem, 1993, pp. 323-326, vol. 209.
Wang et al., "The Development of Highly Potent Inhibitors for Porcupine", J. Med. Chem., 2013, pp. 2700-2704, vol. 56, No. 6.
Yamazaki et al., "Nuclear receptor CAR (NR1I3) is essential for DDC-induced liver injury and oval cell proliferation in mouse liver", Lab Invest, 2011, pp. 1624-1633, vol. 91, No. 11.
Yang et al. "Beta-catenin signaling in murine liver zonation and regeneration: A Wnt-Wnt situation!", Hepatology, 2014, pp. 964-976, vol. 60, No. 3.
Yasuda et al., "RNAi-mediated silencing of hepatic Alas1 effectively prevents and treats the induced acute attacks in acute intermittent porphyria mice." Proc Natl Acad Sci, 2014, pp. 7777-7782, vol. 111, No. 21.
Yeh et al. "Liver-specific beta-catenin knockout mice have bile canalicular abnormalities, bile secretory defect, and intrahepatic cholestasis", Hepatology, 2010, pp. 1410-1419, vol. 52, No. 4.
You et al., "Development of a triazole class of highly potent Porcn inhibitors", Bioorg. Med. Chem. Lett., 2016, pp. 5891-5895, vol. 26, No. 24.

(Continued)

*Primary Examiner* — Jane J Zara
(74) *Attorney, Agent, or Firm* — The Webb Law Firm

(57) ABSTRACT

A method of treating *porphyria* in a patient is provided comprising knocking down or reducing expression or activity of β-catenin in the patient. e.g., in the liver of a patient, to an extent effective to treat *porphyria* in a patient.

19 Claims, 45 Drawing Sheets
(19 of 45 Drawing Sheet(s) Filed in Color)
Specification includes a Sequence Listing.

(56) References Cited

OTHER PUBLICATIONS

Zatloukal et al., "From Mallory to Mallory-Denk bodies: what, how and why?", Exp Cell Res, 2007, pp. 2033-2049, vol. 313.

Zhang et al., "Conditional beta-catenin loss in mice promotes chemical hepatocarcinogenesis: role of oxidative stress and platelet-derived growth factor receptor alpha/phosphoinositide 3-kinase signaling", Hepatology, 2010, pp. 954-965, vol. 52, No. 3.

Ajioka et al., "Biosynthesis of heme in mammals", Biochim Biophys Acta 2006, pp. 723-736, vol. 1763.

Alpini et al., "Bile acid feeding induces cholangiocyte proliferation and secretion: evidence for bile acid-regulated ductal secretion", Gastroenterology, 1999, pp. 179-186, vol. 116.

Apte et al., "Wnt/beta-catenin signaling mediates oval cell response in rodents", Hepatology, 2008, pp. 288-295, vol. 47.

Balwani et al., "The porphyrias: advances in diagnosis and treatment", Blood, 2012, vol. 120, pp. 4496-4504.

Bhamra et al., "Porcupine inhibitor RXC004 enhances immune response in pre-clinical models of cancer", Poster presented at Association for Cancer Research Annual Meeting, 2018, Chicago, IL.

Brady et al., "Inhibition of ferrochelatase and accumulation of porphyrins in mouse hepatocyte cultures exposed to porphyrinogenic chemicals", Arch Toxicol, 1992, pp. 175-181, vol. 66.

Braeuning et al., "Gender-specific interplay of signaling through beta-catenin and CAR in the regulation of xenobiotic-induced hepatocyte proliferation", Toxicol Sci, 2011, pp. 113-122, vol. 123.

Braeuning et al., "Zonation of heme synthesis enzymes in mouse liver and their regulation by beta-catenin and Ha-ras", Biol Chem, 2010, pp. 1305-1313, vol. 391.

Chen et al., "IRE1: ER stress sensor and cell fate executor", Trends Cell Biol, 2013, pp. 547-555, vol. 23, No. 11.

Chen et al., "Small molecule-mediated disruption of Wnt-dependent signaling in tissue regeneration and cancer", Nat. Chem. Biol., 2009, pp. 100-107, vol. 5:2.

Cheng et al., "Discovery of Pyridinyl Acetamide Derivatives as Potent, Selective, and Orally Bioavailable Porcupine Inhibitors", ACS Med. Chem. Lett., 2016, pp. 676-680, vol. 7.

Correia et al., "Cytochrome P450 regulation: the interplay between its heme and apoprotein moieties in synthesis, assembly, repair, and disposal", Drug Metab Rev, 2011, pp. 1-26, vol. 43.

Dailey et al., "Bovine ferrochelatase. Kinetic analysis of inhibition by N-methylprotoporphyrin, manganese, and heme", J Biol Chem, 1983, pp. 11453-11459, vol. 258, No. 19.

Dailey et al., "Erythroid heme biosynthesis and its disorders", Cold Spring Harb Perspect Med, 2013; 3:a011676.

Donohue et al., "Induction of Covalently Crosslinked p62 Oligomers with Reduced Binding to Polyubiquitinated Proteins by the Autophagy Inhibitor Verteporfin", PLOS One, 2014, vol. 9:e114964.

Dudek et al., "Knockdown of β-catenin with Dicer-Substrate siRNAs Reduces Liver Tumor Burden In vivo", The American Society of Gene & Cell Therapy, 2014, pp. 92-101, vol. 22, No. 1.

Elenbaas et al., "A precursor-inducible zebrafish model of acute protoporphyria with hepatic protein aggregation and multiorganelle stress", FASEB J, 2016, pp. 1798-1810, vol. 30.

Essers et al., "Functional interaction between beta-catenin and FOXO in oxidative stress signaling", Science, 2005, pp. 1181-1184, vol. 308.

Fickert et al., "A new xenobiotic-induced mouse model of sclerosing cholangitis and biliary fibrosis" Am J Pathol, 2007, pp. 525-536, vol. 171, No. 2.

Fickert et al., "Bile acid-induced Mallory body formation in drug-primed mouse liver", Am J Pathol., 2002, pp. 2019-2026, vol. 161, No. 6.

Ganesh et al., "Direct Pharmacological Inhibition of β-Catenin by RNA Interference in Tumors of Diverse Origin", Molecular Cancer Therapeutics, 2016, pp. 2143-2155, vol. 15, No. 9.

Glaser et al., "Cholangiocyte proliferation and liver fibrosis" Expert Rev Mol Med, 2009, vol. 11:e7.

Gougelet et al., "T-cell factor 4 and beta-catenin chromatin occupancies pattern zonal liver metabolism in mice", Hepatology, 2014, pp. 2344-2357, vol. 59.

Gross et al., "Induction of hepatic delta-aminolevulinic acid synthetase activity in strains of inbred mice", J Biol Chem, 1971, pp. 606-614, vol. 246, No. 3.

Hanada et al., "Gender dimorphic formation of mouse Mallory-Denk bodies and the role of xenobiotic metabolism and oxidative stress", Gastroenterology, 2010, pp. 1607-1617, vol. 138.

Harada et al., "Autophagy activation by rapamycin eliminates mouse Mallory-Denk bodies and blocks their proteasome inhibitor-mediated formation", Hepatology, 2008, pp. 2026-2035, vol. 47.

Hunter et al., "Molecular enzymology of 5-aminolevulinate synthase, the gatekeeper of heme biosynthesis", Biochim Biophys Acta, 2011, pp. 1467-1473, vol. 1814.

Jiang et al., "A novel porcupine inhibitor blocks WNT pathways and attenuates cardiac hypertrophy." Biochim. Biophys. Acta, Mol. Basis Dis., 2018, pp. 3459-3467, vol. 1864.

Kikuchi et al., "Heme oxygenase and heme degradation.", Biochem Biophys Res Commun, 2005, pp. 558-567, vol. 338.

Ku et al., "Keratins let liver live: Mutations predispose to liver disease and crosslinking generates Mallory-Denk bodies", Hepatology, 2007, pp. 1639-1649, vol. 46.

Ku et al., "Studying simple epithelial keratins in cells and tissues", Methods Cell Biol, 2004; pp. 489-517, vol. 78.

Ledford, "CRISPR editing wreaks chromosomal mayhem in human embryos", Nature, 2020, pp. 17-18, vol. 583.

Liu et al., "Targeting Wnt-driven cancer through the inhibition of Porcupine by LGK974", PNAS., 2013, pp. 20224-20229, vol. 110, No. 50.

Madan et al., "Wnt addiction of genetically defined cancers reversed by PORCN inhibition", Oncogene, 2016, pp. 2197-2207, vol. 35.

Maitra et al., "Ambient Light Promotes Selective Subcellular Proteotoxicity after Endogenous and Exogenous Porphyrinogenic Stress", J Biol Chem, 2015, pp. 23711-23724, vol. 290.

Musunuru, "Genome Editing: The recent history and perspective in cardiovascular disease", J. Am. Coll. Cardiol., 2017, pp. 2808-2821, vol. 70, No. 22.

Nejak-Bowen et al., "Beta-catenin regulates vitamin C biosynthesis and cell survival in murine liver", J. Biol. Chem., 2009, pp. 28115-28127, vol. 284, No. 41.

Nejak-Bowen et al., "Beta-catenin-NF-kappaB interactions in murine hepatocytes: a complex to die for", Hepatology, 2013; pp. 763-774, vol. 57.

Okabe et al., "Wnt signaling regulates hepatobiliary repair following cholestatic liver injury in mice", Hepatology, 2016, pp. 1652-1666, vol. 64.

Ortiz de Montellano et al., "N-Alkylprotoporphyrin IX formation in 3,5-dicarbethoxy-1,4-dihydrocollidine-treated rats. Transfer of the alkyl group from the substrate to the porphyrin.", J Biol Chem, 1981, pp. 6708-6713, vol. 256.

Ortiz de Montellano et al., "Inhibition of hepatic ferrochelatase by the four isomers of N-methylprotoporphyrin IX.", Biochem Biophys Res Commun, 1980, pp. 1436-1442, vol. 97.

Popov et al., "Second-generation antisense oligonucleotides against β-catenin protect mice against diet-induced hepatic steatosis and hepatic and peripheral insulin resistance", Faseb J., 2016, pp. 1207-1217, vol. 30.

Prakash et al., "Targeted delivery of antisense oligonucleotides to hepatocytes using triantennary N-acetyl galactosamine improves potency 10-fold in mice", Nucleic Acids Research, 2014, pp. 8796-8807, vol. 42, No. 13.

Proffitt et al., "Pharmacological Inhibition of the Wnt Acyltransferase PORCN Prevents Growth of WNT-Driven Mammary Cancer", Cancer Res., 2013, pp. 502-507, vol. 73, No. 2.

Puy et al., "Porphyrias", Lancet, 2010, pp. 924-937, vol. 375.

Sachar et al., "Chronic Treatment with Isoniazid Causes Protoporphyrin IX Accumulation in Mouse Liver", Chem Res Toxicol 2016; pp. 1293-1297, vol. 29, No. 8.

Saggi et al., "Loss of hepatocyte β-catenin protects mice from experimental porphyria-associated liver injury", pp. 1-33.

(56) References Cited

OTHER PUBLICATIONS

Saggi et al., "Loss of hepatocyte β-catenin protects mice from experimental porphyria-associated liver injury", J. Hepatol, 2018, https://doi.org/10.1016/j.jhep.2018.09.023.
Schultz et al., "Iron and porphyrin trafficking in heme biogenesis", J Biol Chem, 2010, pp. 26753-26759, vol. 285.
Singla et al., "Lamin aggregation is an early sensor of porphyria-induced liver injury", J Cell Sci, 2013, pp. 3105-3112, vol. 126.

* cited by examiner

```
AGGATACAGCGGCTTCTGCGCGACTTATAAGAGCTCCTTGTGCGGCGCCATTTTAAGCCTCTCGGTCTGTGGCA
GCAGCGTTGGCCCGGCCCCGGGAGCGGAGAGCGAGGGGAGGCGGAGACGGAGGAAGGTCTGAGGAGCAGCTTCA
GTCCCCGCCGAGCCGCCACCGCAGGTCGAGGACGGTCGGACTCCCGCGGCGGGAGGAGCCTGTTCCCCTGAGGG
TATTTGAAGTATACCATACAACTGTTTTGAAAATCCAGCGTGGACAATGGCTACTCAAGCTGATTTGATGGAGT
TGGACATGGCCATGGAACCAGACAGAAAAGCGGCTGTTAGTCACTGGCAGCAACAGTCTTACCTGGACTCTGGA
ATCCATTCTGGTGCCACTACCACAGCTCCTTCTCTGAGTGGTAAAGGCAATCCTGAGGAAGAGGATGTGGATAC
CTCCCAAGTCCTGTATGAGTGGGAACAGGGATTTTCTCAGTCCTTCACTCAAGAACAAGTAGCTGATATTGATG
GACAGTATGCAATGACTCGAGCTCAGAGGGTACGAGCTGCTATGTTCCCTGAGACATTAGATGAGGGCATGCAG
ATCCCATCTACACAGTTTGATGCTGCTCATCCCACTAATGTCCAGCGTTTGGCTGAACCATCACAGATGCTGAA
ACATGCAGTTGTAAACTTGATTAACTATCAAGATGATGCAGAACTTGCCACACGTGCAATCCCTGAACTGACAA
AACTGCTAAATGACGAGGACCAGGTGGTGGTTAATAAGGCTGCAGTTATGGTCCATCAGCTTTCTAAAAAGGAA
GCTTCCAGACACGCTATCATGCGTTCTCCTCAGATGGTGTCTGCTATTGTACGTACCATGCAGAATACAAATGA
TGTAGAAACAGCTCGTTGTACCGCTGGGACCTTGCATAACCTTTCCCATCATCGTGAGGGCTTACTGGCCATCT
TTAAGTCTGGAGGCATTCCTGCCCTGGTGAAAATGCTTGGTTCACCAGTGGATTCTGTGTTGTTTTATGCCATT
ACAACTCTCCACAACCTTTTATTACATCAAGAAGGAGCTAAAATGGCAGTGCGTTTAGCTGGTGGGCTGCAGAA
AATGGTTGCCTTGCTCAACAAAACAAATGTTAAATTCTTGGCTATTACGACAGACTGCCTTCAAATTTTAGCTT
ATGGCAACCAAGAAAGCAAGCTCATCATACTGGCTAGTGGTGGACCCCAAGCTTTAGTAAATATAATGAGGACC
TATACTTACGAAAACTACTGTGGACCACAAGCAGAGTGCTGAAGGTGCTATCTGTCTGCTCTAGTAATAAGCC
GGCTATTGTAGAAGCTGGTGGAATGCAAGCTTTAGGACTTCACCTGACAGATCCAAGTCAACGTCTTGTTCAGA
ACTGTCTTTGGACTCTCAGGAATCTTTCAGATGCTGCAACTAAACAGGAAGGGATGGAAGGTCTCCTTGGGACT
CTTGTTCAGCTTCTGGGTTCAGATGATATAAATGTGGTCACCTGTGCAGCTGGAATTCTTTCTAACCTCACTTG
CAATAATTATAAGAACAAGATGATGGTCTGCCAAGTGGGTGGTATAGAGGCTCTTGTGCGTACTGTCCTTCGGG
CTGGTGACAGGGAAGACATCACTGAGCCTGCCATCTGTGCTCTTCGTCATCTGACCAGCCGACACCAAGAAGCA
GAGATGGCCCAGAATGCAGTTCGCCTTCACTATGGACTACCAGTTGTGGTTAAGCTCTTACACCCACCATCCCA
CTGGCCTCTGATAAAGGCTACTGTTGGATTGATTCGAAATCTTGCCCTTTGTCCCGCAAATCATGCACCTTTGC
GTGAGCAGGGTGCCATTCCACGACTAGTTCAGTTGCTTGTTCGTGCACATCAGGATACCCAGCGCCGTACGTCC
ATGGGTGGGACACAGCAGCAATTTGTGGAGGGGGTCCGCATGGAAGAAATAGTTGAAGGTTGTACCGGAGCCCT
TCACATCCTAGCTCGGGATGTTCACAACCGAATTGTTATCAGAGGACTAAATACCATTCCATTGTTTGTGCAGC
TGCTTTATTCTCCCATTGAAAACATCCAAAGAGTAGCTGCAGGGGTCCTCTGTGAACTTGCTCAGGACAAGGAA
GCTGCAGAAGCTATTGAAGCTGAGGGAGCCACAGCTCCTCTGACAGAGTTACTTCACTCTAGGAATGAAGGTGT
GGCGACATATGCAGCTGCTGTTTTGTTCCGAATGTCTGAGGACAAGCCACAAGATTACAAGAAACGGCTTTCAG
TTGAGCTGACCAGCTCTCTCTTCAGAACAGAGCCAATGGCTTGGAATGAGACTGCTGATCTTGGACTTGATATT
GGTGCCCAGGGAGAACCCCTTGGATATCGCCAGGATGATCCTAGCTATCGTTCTTTTCACTCTGGTGGATATGG
CCAGGATGCCTTGGGTATGGACCCCATGATGGAACATGAGATGGGTGGCCACCACCCTGGTGCTGACTATCCAG
TTGATGGGCTGCCAGATCTGGGGCATGCCCAGGACCTCATGGATGGGCTGCCTCCAGGTGACAGCAATCAGCTG
GCCTGGTTTGATACTGACCTGTAAATCATCCTTTAGGTAAGAAGTTTTAAAAAGCCAGTTTGGGTAAAATACTT
TTACTCTGCCTACAGAACTTCAGAAAGACTTGGTTGGTAGGGTGGGAGTGGTTTAGGCTATTTGTAAATCTGCC
ACAAAAACAGGTATATACTTTGAAAGGAGATGTCTTGGAACATTGGAATGTTCTCAGATTTCTGGTTGTTATGT
GATCATGTGTGGAAGTTATTAACTTTAATGTTTTTGCCACAGCTTTTGCAACTTAATACTCAAATGAGTAACA
TTTGCTGTTTTAAACATTAATAGCAGCCTTTCTCTCTTTATACAGCTGTATTGTCTGAACTTGCATTGTGATTG
GCCTGTAGAGTTGCTGAGAGGGCTCGAGGGGTGGCTGGTATCTCAGAAAGTGCCTGACACACTAACCAAGCTG
AGTTCCTATGGGAACAATTGAAGTAAACTTTTGTTCTGGTCCTTTTGGTCGAGGAGTAACAATACAAATGG
ATTTTGGGAGTGACTCAAGAAGTGAAGAATGCACAAGAATGGATCACAAGATGGAATTTATCAAACCCTAGCCT
TGCTTGTTAAATTTTTTTTTTTTTTTTTAAGAATATCTGTAATGGTACTGACTTTGCTTGCTTTGAAGTAGC
TCTTTTTTTTTTTTTTTTTTTTTGCAGTAACTGTTTTTAAGTCTCTCGTAGTGTTAAGTTATAGTGAAT
ACTGCTACAGCAATTTCTAATTTTTAAGAATTGAGTAATGGTGTAGAACACTAATTCATAATCACTCTAATTAA
TTGTAATCTGAATAAAGTGTAACAATTGTGTAGCCTTTTGTATAAAATAGACAAATAGAAAATGGTCCAATTA
GTTTCCTTTTAATATGCTTAAAATAAGCAGGTGGATCTATTTCATGTTTTTGATCAAAAACTATTTGGGATAT
GTATGGGTAGGGTAAATCAGTAAGAGGTGTTATTTGGAACCTTGTTTTGGACAGTTTACCAGTTGCCTTTTATC
CCAAAGTTGTTGTAACCTGCTGTGATACGATGCTTCAAGAGAAATGCGGTTATAAAAAATGGTTCAGAATTAA
ACTTTTAATTCATTCGATTG
```

FIG. 1

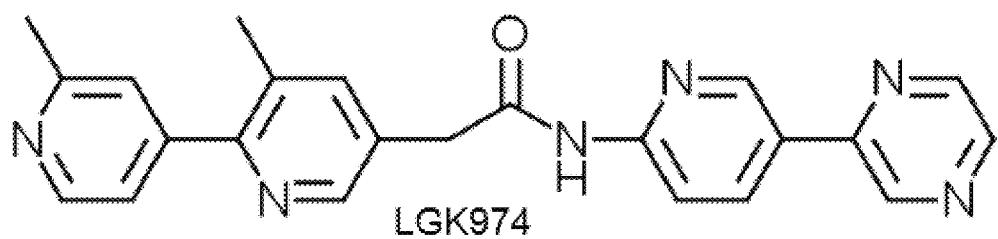
LGK974
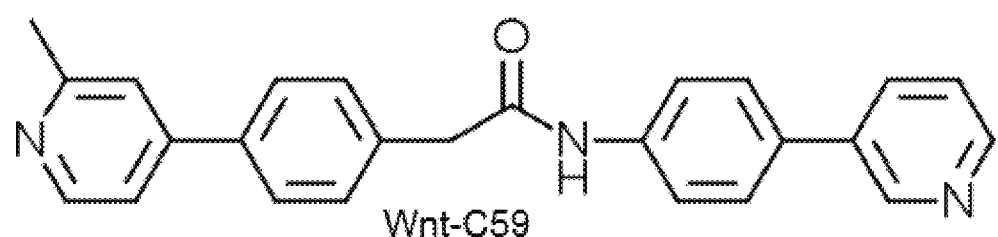
Wnt-C59
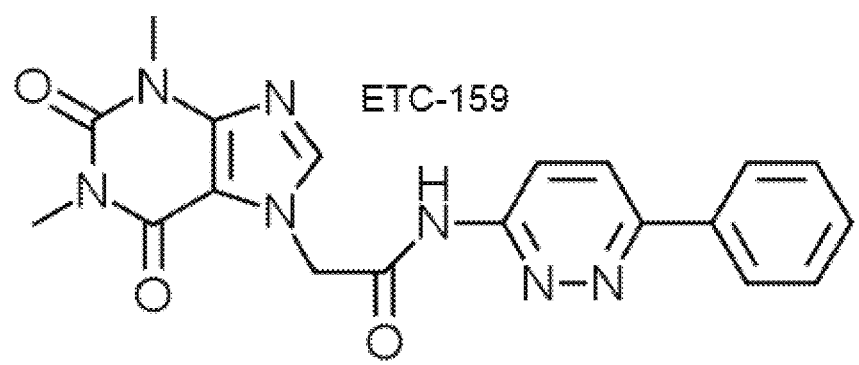
ETC-159
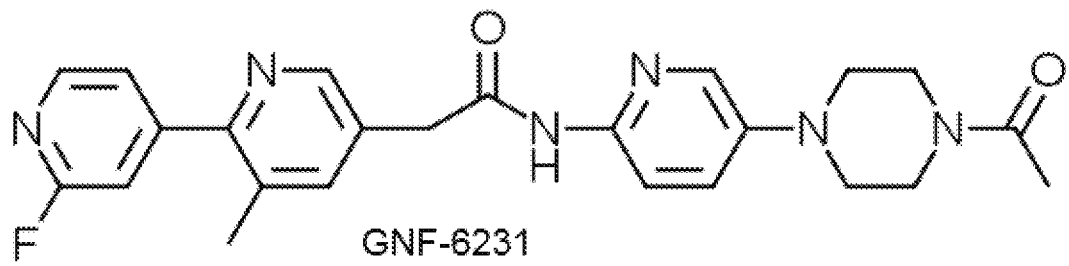
GNF-6231
FIG. 3C

WT1: β-catenin loxp +/+ Albumin Cre -/-
KO1: β-catenin loxp +/+ Albumin Cre +/-
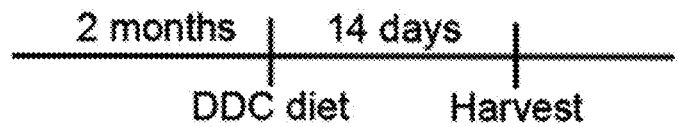
FIG. 4A
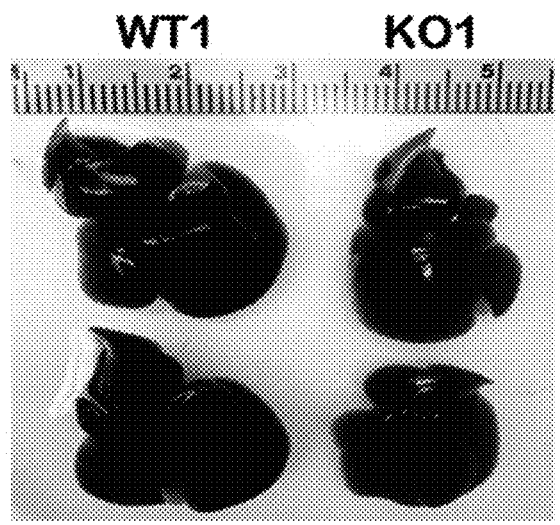
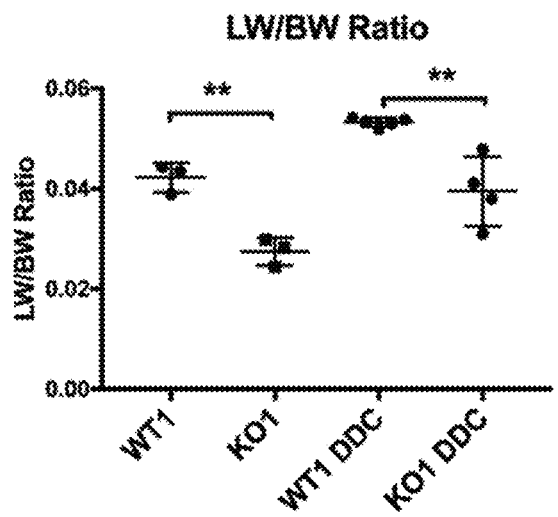
FIG. 4B

WT2: LRP5/6 loxp +/+ Albumin Cre -/-
KO2: LRP5/6 loxp +/+ Albumin Cre +/-

GS IHC

H&E

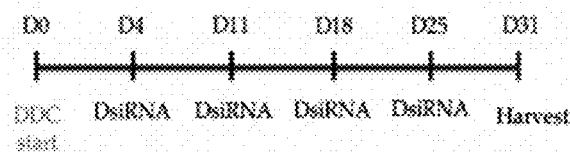
FIG. 9A
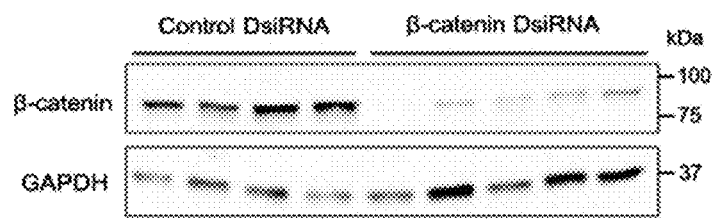
FIG. 9B
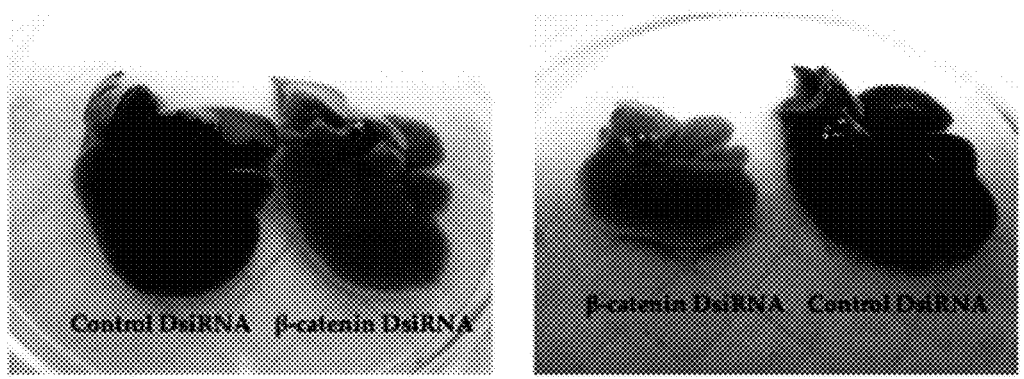
LW/BW Ratio
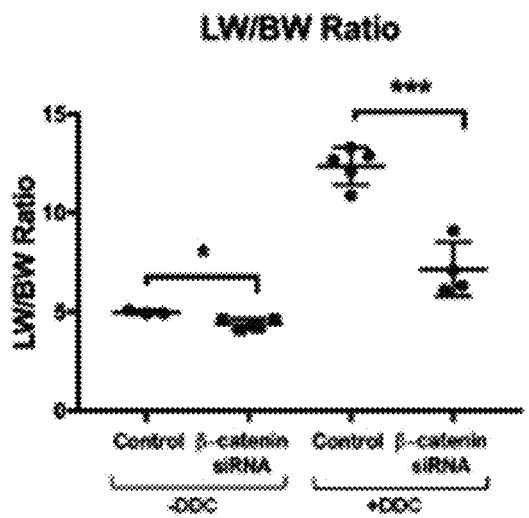
FIG. 9C

METHODS OF TREATING PORPHYRIA

CROSS REFERENCE TO RELATED APPLICATIONS

This application is a continuation of U.S. patent application Ser. No. 16/509,734 filed Jul. 12, 2019, which claims the benefit of U.S. Provisional Patent Application No. 62/697,548 filed Jul. 13, 2018, each of which is incorporated herein by reference in its entirety.

STATEMENT REGARDING FEDERALLY SPONSORED RESEARCH

This invention was made with government support under Grant Nos. DK062277; DK100287 and DK103775, awarded by the National Institutes of Health. The government has certain rights in the invention.

REFERENCE TO A SEQUENCE LISTING SUBMITTED VIA EFS-WEB

The content of the ASCII text file of the sequence listing named "2101318_ST25.txt" which is 36,824 bytes in size was created on Mar. 2, 2021 and electronically submitted via EFS-Web herewith the application is incorporated herein by reference in its entirety.

Provided herein are methods of treating *porphyria*.

Porphyrins are tetrapyrrole compounds and heme precursors, with heme being a co-factor for functionally diverse hemoproteins such as cytochrome-P450, hemoglobin, and peroxidases. Heme biosynthesis starts in mitochondria, where glycine and succinyl Co-A are combined to form the first committed metabolite of the pathway, δ-aminolevulinic acid (ALA), catalyzed by ALA-synthase (ALA-S). ALA leaves the mitochondria, and is sequentially converted in the cytosol to porphobilinogen, hydroxymethylbilane, uroporphyrin (Uro) and then to coproporphyin (Copro), which re-enters mitochondria. In the penultimate step, protoporphyrin-IX is generated, which is metallated by ferrochelatase to form the iron containing heme.

3,5-Diethoxycarbonyl-1,4-dihydrocollidine (DDC), a porphyrinogenic compound, has been widely used to induce hepatic *porphyria* and Mallory-Denk bodies in mouse models. DDC perturbs porphyrin biosynthesis at multiple steps. DDC N-methylates heme residues of some hepatic cytochrome-P450 enzymes, which subsequently demetallates and releases the tetrapyrrole moiety in the form of N-methyl protoporphyrin IX. N-methyl protoporphyrin IX is a potent inhibitor of ferrochelatase and blocks conversion of protoporphyrin-IX to heme. Thus, hepatic NMP accumulation causes buildup of tetrapyrrole precursors, including protoporphyrin-IX. Additionally, ALA-S is under negative feedback regulation of heme. Inhibition of ferrochelatase by N-methyl protoporphyrin IX, and the subsequent heme-deficient state, de-represses ALA-S expression, which in turn generates more ALA that feeds forward into the heme biosynthetic pathway, leading to accumulation of toxic porphyrins.

DDC has also been used widely to study formation of Mallory-Denk bodies, which are hepatocellular inclusions found in diseases like alcoholic and non-alcoholic steatohepatitis and metabolic liver diseases. Aggregates of keratin proteins K8 and K18 constitute a major component of Mallory-Denk bodies as they are early sensors of porphyrin-mediated liver injury. Protein aggregation perturbs protein clearance, causing proteasomal inhibition and induction of autophagy. Chronic DDC exposure also results in pericholangitis, ductular reaction, oval cell response and periductal fibrosis, similar to that seen in primary sclerosing cholangitis patients, owing to crystallized porphyrin obstructing small bile ducts.

SUMMARY OF THE INVENTION

A method of treating *porphyria* in a patient is provided. The method comprises: decreasing expression or activity of β-catenin in the patient, e.g., in the patient's liver, and optionally targeting delivery to the patient's liver, thereby decreasing porphyrin production and/or accumulation, or reducing one or more symptoms of *porphyria*, such as liver injury in the patient. Related reagents and uses for the reagents also are provided.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1: An exemplary, but non-limiting sequence for β-catenin (SEQ ID NO: 1), from *Homo sapiens* catenin beta 1 (CTNNB1), mRNA transcript variant 1.

FIGS. 3A-3C provide structures of exemplary PORCN inhibitors.

FIGS. 4A-4F: Alb-cre β-catenin KO have lesser injury than WT after 2 weeks of DDC. (FIG. 4A) Treatment regimen for WT1 and Alb-cre β-catenin KO (KO1) on DDC. (FIG. 4B) Gross liver specimens from WT1 and KO1 mice on 2 week DDC demonstrate that WT1 livers become enlarged and turn dark brown in color, while the KO1 livers are smaller and lighter in color (right panel). Liver weight to body weight ratios are lower in KO1 compared to WT1 after DDC (left panel). (FIG. 4C) Both biliary and hepatocyte injury are decreased in KO1 after DDC, as assessed by ALP and ALT. (FIG. 4D) Glutamine synthetase IHC confirms loss of β-catenin in KO1. (FIG. 4E) H&E shows lesser porphyrin accumulation in KO1 compared to WT1 after DDC. (FIG. 4F) Sirius red staining shows equivalent fibrosis in KO1 after DDC compared to WT1. n=3 for WT1 and KO1 baseline, n=5 WT1+DDC, n=4 KO1+DDC; *P<0.05, **P<0.01 by Student's t test.

(FIG. 5A) WB demonstrates absent β-catenin and cyclin D1 expression in β-catenin KO (KO1) livers. Yap expression increases in KO1; however, the inactivated, S127 p-Yap form also increases as well. (FIG. 5B) WB shows that in LRP5/6 KO (KO2) livers after DDC. β-catenin is still present; however, cyclin D1 is significantly decreases. Yap and p-Yap are not significantly changed between WT2 and KO2.

(FIG. 6A) IHC shows a significant decrease in both cyclin D1 and Ki67 staining in KO1 after DDC. (FIG. 6B) Ductular response is equivalent in WT1 and KO1 livers, as assessed by EpCAM and Sox9 IHC. (FIG. 6C) There is lesser inflammation in KO1 livers after DDC, as demonstrated by decreased CD45, CD68, and neutrophil elastase staining in KO1 livers. For IHC, n≥3 liver sections from n≥3 animals from both groups were analyzed; representative images are shown.

(FIG. 7A) Treatment regimen for WT2 and Alb-cre LRP5/6 KO (KO2) on DDC. (FIG. 7B) Gross liver specimens show that WT2 livers are larger and darker than KO2 livers after DDC. (FIG. 7C) Liver weight to body weight ratios are lower in KO2 compared to WT2 after DDC. (FIG. 7D) Biliary injury is decreased in KO2 after DDC, as assessed by lower ALP serum levels. (FIG. 7E) Glutamine synthetase IHC confirms loss of β-catenin transcriptional activation in KO1. (FIG. 7F) H&E shows a modest decrease in porphyrin accumulation in KO2 compared to WT2 after DDC. (FIG. 7G) Sirius red staining shows equivalent fibrosis in KO2 after DDC compared to WT. n=3 for WT2 and KO2 baseline, n=5 WT2+DDC, n=4 KO2+DDC; *P<0.001; **P<0.0001 by Student's t test.

(FIG. 8A) IHC shows a significant decrease in cyclin D1 in KO2 after DDC; however, hepatocyte proliferation appears to be unimpaired. (FIG. 8B) Ductular response is equivalent in WT2 and KO2 livers, as assessed by EpCAM and Sox9 IHC. (FIG. 8C) Inflammation is decased in KO2 livers after DDC, as shown by decreased CD45, F4/80, and neutrophil elastase staining. For IHC, n≥3 liver sections from n≥3 animals from both groups were analyzed; representative images are shown.

FIGS. 9A-9F: Exogenous inhibition of β-catenin using DsiRNA results in decreased injury after 4 weeks of DDC. (FIG. 9A) Treatment regimen for administration of DsiRNAs after DDC. (FIG. 9B) Western blot confirms decreased β-catenin protein after DsiRNA treatment. (FIG. 9C) Gross liver specimens demonstrate that control livers become enlarged and dark red after DDC, while β-catenin DsiRNA treated livers are smaller and lighter in color. Liver weight to body weight ratios confirm decrease in β-catenin DsiRNA-treated livers after DDC. (FIG. 9D) Both biliary and hepatocyte injury are decreased after β-catenin DsiRNA and DDC, as assessed by ALP and ALT. (FIG. 9E) Sirius red staining shows a reduction in fibrosis after DDC and β-catenin DsiRNA treatment compared to control DsiRNA and DDC. (FIG. 9F) Channel splitting and quantification of representative Sirius red images demonstrates a significant decrease in percent area of fibrosis in β-catenin DsiRNA treated livers after DDC. For C, n=3 for control and n=4 for β-catenin siRNA at baseline, n=5 control+DDC, n=4 β-catenin+DDC; for D, n=3 for control and n=4 for β-catenin siRNA at baseline, n=11 control+DDC, n=11 β-catenin+DDC; *P<0.05; P<0.01; *P<0.001; ****P<0.0001 by Student's t test.

(FIG. 10A) GS IHC confirms loss of β-catenin in hepatocytes after DsiRNA treatment. (FIG. 10B) α-SMA expression is equivalent in control and β-catenin DsiRNA treated livers after DDC. (FIG. 10C) Hepatocyte proliferation is decreased in livers after β-catenin DsiRNA treatment, while cholangiocyte proliferation is unaffected. (FIG. 10D) Inflammatory markers CD45 and F4/80 are decreased after β-catenin DsiRNA, while neutrophil elastase is increased. (FIG. 10E) Sox9-positive cells extend into the parenchyma after β-catenin DsiRNA treatment and DDC. For IHC, n≥3 liver sections from n≥3 animals from both groups were analyzed; representative images are shown.

(FIG. 11A) The ratio of Yap to p-Yap is not significantly different between control siRNA and β-catenin DsiRNA treated livers after DDC. (FIG. 11B) Jagged1 mRNA expression is increased after β-catenin DsiRNA treatment and DDC compared to control; however, Notch1 expression is significantly decreased. n=3 mice per group analyzed in duplicate; *P<0.05 by Student's t-test.

(FIG. 12A) Transcription factor assay shows no significant changes in NF-κB activity between control and β-catenin DsiRNA livers after DDC. (FIG. 12B) Total bile acid accumulation in the liver is equivalent in control and β-catenin DsiRNA treated livers. (FIG. 12A) n=4 mice per group analyzed in triplicate; for (FIG. 12B), n=4 control DsiRNA-treated mice and n=6 β-catenin DsiRNA-treated mice.

(FIG. 13A) H&E shows fewer porphyrin inclusions (arrows) in livers treated with β-catenin DsiRNA and DDC compared to controls. (FIG. 13B) Plotting the percent porphyrin per image using ImageJ Fiji to separate color channels shows a quantifiable decrease in porphyrin after β-catenin DsiRNA treatment and DDC. (FIG. 13C) Determination of total liver porphyrins (except heme) by fluorescence assay confirms less porphyrin accumulation in β-catenin DsiRNA-treated livers. The data is expressed as mean with error bars representing standard error of measurements. n=3 control DsiRNA, n=3 β-catenin DsiRNA, n=3 Control DsiRNA+DDC, n=4 β-catenin DsiRNA+DDC. P<0.05; **P<0.0001 by Student's t-test. (FIG. 13D**) Measurement of porphyrin intermediates by LC-MS shows decreased PP-IX in livers treated with β-catenin DsiRNA after DDC compared to those treated with control DsiRNA and DDC. n=3 control DsiRNA, n=3 β-catenin DsiRNA, n=4 Control DsiRNA+DDC, n=4 β-catenin DsiRNA+DDC. *P<0.05; ****P<0.0001 by Student's t-test.

(FIG. 14A) Both Cyp3a1 and Cyp3a11 are increased in KO1 at baseline compared to WT1. (FIG. 14B) Expression of 2 Cyp3a isoforms, Cyp3a1 and Cyp3a11, are equivalent after β-catenin DsiRNA at baseline (before DDC). (FIG. 14C) Cyp3a1 protein expression is notably increased in livers treated with β-catenin DsiRNA and DDC compared to DDC alone. (FIG. 14D) CAR mRNA expression is decreased basally after β-catenin DsiRNA administration. After DDC, CAR expression is suppressed in controls to a similar extent as β-catenin DsiRNA treated livers before DDC. n=3 mice per group analyzed in duplicate. For A, *P<0.05; **P<0.01 by Student's t-test. For D, *P<0.05 vs. control DsiRNA, #P<0.05 vs. β-catenin DsiRNA, % P<0.05 vs. control+DDC, all by Student's t-test.

(FIG. 15A) WB shows decrease in ALA-S, the rate-limiting enzyme in the heme biosynthesis pathway, after β-catenin DsiRNA and DDC. (FIG. 15B) Ferrochelatase (FC) protein expression is equivalent in control and β-catenin DsiRNA livers after DDC. (FIG. 15C) ALA-aminolevulinic acid dehydratase (ALA-D) is decreased in livers of mice treated with β-catenin DsiRNA and DDC. (FIG. 15D) Expression of ALA-S and ALA-D are decreased after β-catenin DsiRNA at baseline (before DDC). (FIG. 15E) ALA-S and ALA-D are also significantly decreased in KO1 at baseline. (FIG. 15F) ALA-D is suppressed in KO2 compared to controls at baseline, while ALA-S is insignificantly decreased. n≥3 mice per group analyzed in duplicate; *P<0.05; P<0.01; *P<0.001 by Student's t-test.

FIG. 17A (panel A and panel C); 15% resolving gel: FIG. 17A (panel B and panel D), and exposed to film for the indicated times. Ponceau staining of the PVDF membranes are shown as a loading control, and show equal protein loading among different samples. For FIG. 17A (panels A, C), arrowheads represent bottom of the well, stacking-resolving gel junction, and end of the gel, respectively. For FIG. 17 (panels B and D), arrowheads represent the stacking-resolving gel junction. (FIG. 17B) Measurement of total heme content shows persistence of heme in livers treated with β-catenin DsiRNA after DDC compared to those treated with control DsiRNA and DDC. (FIG. 17C) HO-1 mRNA expression is suppressed in the absence of β-catenin before and after DDC compared to controls. For FIG. 17B, n=3 mice per group; % P<0.05 vs. control+DDC by Student's t-test. For FIG. 17C, n=3 mice per group analyzed in duplicate; *P<0.05 vs. control DsiRNA, #P<0.05 vs. β-catenin DsiRNA, % P<0.05 vs. control+DDC, all by Student's t-test.

FIG. 18 (panels A, B, C, and D) Total liver homogenates were separated on non-reducing denaturing PAGE, and heme content assayed as detailed in the Methods section. Ponceau staining of the PVDF membranes are shown as a loading control, and show equal protein loading among different samples.

FIG. 20A (panel A) Cytosolic K8 protein expression (in both monomer and HMW aggregate form) is increased in both control and β-catenin DsiRNA treated livers after DDC. FIG. 20A (panel B) Monomeric and aggregate forms of cytosolic K18 is also increased after DDC. FIG. 20A (panel C) Loss in monomeric nuclear lamin A/C after DDC was prevented in β-catenin DsiRNA treated livers. FIG. 20A (panel D) β-catenin DsiRNA treated livers also showed persistence of the momomeric form of nuclear lamin B1 after DDC. For FIG. 20A (panels A, B, C, and D), monomer (arrowhead, 'mono') appears after a short chemiluminescence exposure, while HMW aggregates in upper panel are after a longer exposure. (FIG. 20B) Relative change (with respect to control and β-catenin DsiRNA at baseline) in monomer band intensity after DDC feeding. (FIG. 20C) Quantification of HMW aggregates after DDC-feeding in control vs. β-catenin DsiRNA treated mice. The area of the blot quantified is shown in solid lined box. *P<0.05.

(FIG. 21A) WB for IRE1α, an indicator of ER stress and the UPR, shows decreased aggregates and an increase in the monomeric form after β-catenin DsiRNA and DDC compared to controls. (FIG. 21B) CHOP, another ER stress marker, is also increased in β-catenin DsiRNA-treated livers after DDC compared to DDC alone. (FIG. 21C) WB for p62, a ubiquitin/proteasomal marker, shows presence of the monomeric form in β-catenin DsiRNA treated livers despite formation of HMW aggregates due to DDC. (FIG. 21D) WB for Ub shows a similar extent of proteasomal inhibition in both control and β-catenin DsiRNA-treated mice after DDC. Dotted box indicates increased accumulation of HMW ubiquitinated proteins after DDC. (FIG. 21E) WB of LC3B proteins shows decrease in the amount of the LC3B I form after DDC, while HMW aggregates increase. Top panel shows HMW aggregate, and bottom panel shows LC3B I and II bands. (FIG. 21F) Quantification of band intensity from immunoblot shown in FIG. 21E demonstrates increased autophagy in controls after DDC but not in β-catenin DsiRNA treated livers (right panel). LC3B aggregates are also decreased in β-catenin DsiRNA treated livers (left panel). *P<0.05.

(FIG. 22A) In normal liver, DDC N-methylates heme to form NMP, which inhibits FC, causing heme depletion and accumulation of porphyrins such as Uro, Copro, and PP-IX. β-catenin regulates the expression of several genes, such as ALA-D and HO-1, that are involved in this process. The net result is exacerbation of injury when β-catenin is present. (FIG. 22B) In the absence of β-catenin, ALA-D expression decreases, resulting in less PP-IX accumulation and less heme depletion. Loss of β-catenin also reduces HO-1 expression, which further prevents heme depletion. The decrease in porphyrin intermediates and maintenance of cellular heme in turn reduces ALA-S expression. Purple arrows, effects mediated by DDC; green arrows, effects mediated by β-catenin.

(FIG. 23A) Both biliary and hepatic injury are decreased after DCC in Wnt-C59-treated livers. (FIG. 23B) Wnt-C59 suppresses transcriptional activation of Wnt/β-catenin target gene GS. (FIG. 23C) H&E shows less porphyrin in Wnt-C59-treated livers compared to controls after DCC (100×).

(FIG. 25A) SDS-PAGE stained with Coomassie Blue highlights changes in protein banding pattern (arrows with roman numerals i-v) as a function of DDC in control vs. β-catenin DsiRNA-treated livers. (FIG. 25B) WB shows decrease in the amount of the LC3BI form after β-catenin DsiRNA, while LC3BII increases, indicating increased autophagy. LC3B aggregates are also decreased in β-catenin DsiRNA+DDC.

DETAILED DESCRIPTION

Figure 2:
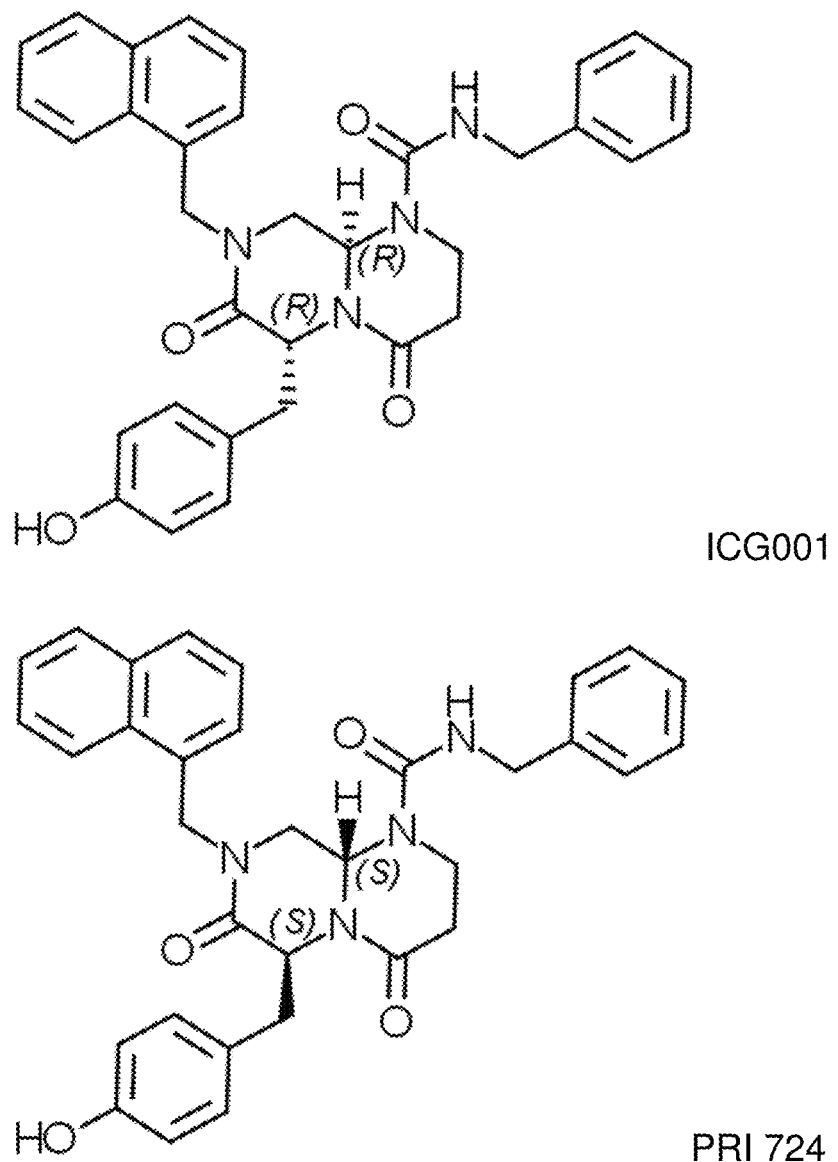
FIG. 2 provides structures of ICG001 and PRI 724.

The following description is merely exemplary in nature and is in no way intended to limit the invention, its application, or uses. While the description is designed to permit one of ordinary skill in the art to make and use the invention, and specific examples are provided to that end, they should in no way be considered limiting. It will be apparent to one of ordinary skill in the art that various modifications to the following will fall within the scope of the appended claims. The present invention should not be considered limited to the presently disclosed aspects, whether provided in the examples or elsewhere herein.

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions refer to word forms, cognates and grammatical variants of those words or phrases. As used herein "a" and "an" refer to one or more. Patent publications cited below are hereby incorporated herein by reference in their entirety to the extent of their technical disclosure and consistency with the present specification.

As used herein, the terms "comprising," "comprise" or "comprised," and variations thereof, are open ended and do not exclude the presence of other elements not identified. In contrast, the term "consisting of" and variations thereof is intended to be closed, and excludes additional elements in anything but trace amounts.

As used herein, the term "patient" or "subject" refers to members of the animal kingdom including but not limited to human beings and "mammal" refers to all mammals, including, but not limited to human beings.

As used herein, the "treatment" or "treating" of *porphyria* means administration to a patient by any suitable dosage regimen, procedure and/or administration route of a composition, device, or structure with the object of achieving a desirable clinical/medical end-point, including but not limited to, preventing, reducing, and/or eliminating any symptom of *porphyria*, such as liver damage, and/or reducing or decreasing porphyrin production and/or accumulation. An amount of any reagent or therapeutic agent, administered by any suitable route, effective to treat a patient is an amount capable of preventing, reducing, and/or eliminating any symptom of *porphyria*, such as liver damage, and/or reducing or decreasing porphyrin production and/or accumulation in a patient, e.g., ranging from 1 pg per dose to 10 g per dose, including any amount there between, such as 1 ng. 1 µg, 1 mg, 10 mg, 100 mg, or 1 g per dose. The therapeutic agent may be administered by any effective route, and, for example, may be administered as a single bolus, at regular or irregular intervals, in amounts and intervals as dictated by any clinical parameter of a patient, or continuously.

The compositions described herein can be administered by any effective route, such as parenteral, e.g., intravenous, intramuscular, subcutaneous, intradermal, etc., formulations of which are described below and in the below-referenced publications, as well as is broadly-known to those of ordinary skill in the art.

Active ingredients, such as nucleic acids or analogs thereof, may be compounded or otherwise manufactured into a suitable composition for use, such as a pharmaceutical dosage form or drug product in which the compound is an active ingredient. Compositions may comprise a pharmaceutically acceptable carrier, or excipient. An excipient is an inactive substance used as a carrier for the active ingredients of a medication. Although "inactive," excipients may facilitate and aid in increasing the delivery or bioavailability of an active ingredient in a drug product. Non-limiting examples of useful excipients include: antiadherents, binders, rheology modifiers, coatings, disintegrants, emulsifiers, oils, buffers, salts, acids, bases, fillers, diluents, solvents, flavors, colorants, glidants, lubricants, preservatives, antioxidants, sorbents, vitamins, sweeteners, etc., as are available in the pharmaceutical/compounding arts.

Useful dosage forms include: intravenous, intramuscular, or intraperitoneal solutions, oral tablets or liquids, topical ointments or creams and transdermal devices (e.g., patches). In one embodiment, the compound is a sterile solution comprising the active ingredient (drug, or compound), and a solvent, such as water, saline, lactated Ringer's solution, or phosphate-buffered saline (PBS). Additional excipients, such as polyethylene glycol, emulsifiers, salts and buffers may be included in the solution.

Suitable dosage forms may include single-dose, or multiple-dose vials or other containers, such as medical syringes, containing a composition comprising an active ingredient useful for treatment of *porphyria* as described herein.

Expression of a gene refers to the conversion of a DNA sequence of a gene, e.g., the CTNNB1 gene, to an active, mature gene product such as a polypeptide/protein, or a functional nucleic acid, and includes, for example, transcription, post-transcriptional modification (e.g., splicing) translation, and post-translational processing and/or modification of a protein. Expression of a gene can be reduced by any effective mechanism at any stage of the gene expression process, such as by affecting transcriptional activation, transcription, post-transcriptional RNA processing, translation, and post-translational processing or modification. Activity of a gene product, such as β-catenin, may be decreased not only by decreasing expression of the active protein product, but by affecting the mature protein product, such as by blocking, decoying, or otherwise interfering with the binding of the active product, or a complex containing the active product, to prevent its activity, e.g., of β-catenin in Wnt/β-catenin/TCF transcriptional activation.

Provided herein is a method of treating *porphyria* in a patient that comprises decreasing expression of β-catenin, or activity of β-catenin in a patient, e.g., in a patient's liver. There are a number of ways to decrease expression or activity of β-catenin in a patient, including, for example, and without limitation: RNA interference, antisense technology, and inhibition of the transcriptional activation activity of β-catenin through use of, e.g., small molecules or reagents that interfere with, e.g., Wnt/β-catenin/TCF transcriptional activation activity, such as decoys, binding reagents, antagonists, etc., as described in further detail below. Treatment of a patient results in a decrease in one or more symptoms of *porphyria*, such as liver damage, and results in decrease of porphyrin production and/or accumulation in the patient.

β-catenin (also Catenin beta-1, or CTNNB1, encoded in humans by the CTNNB1 gene, see, e.g., Gene ID: 1499, HGNC ID: HGNC: 2514, OMIM 116806, UniProtKB-P35222 (CTNB1_HUMAN)) is an adherens junction protein and a downstream component of the canonical Wnt signaling pathway. An exemplary, but non-limiting sequence for human β-catenin (SEQ ID NO: 1) is provided in FIG. 1.

Expression of β-catenin may be accomplished by RNA interference (RNAi), using an RNAi reagent, such as a nucleic acid or nucleic acid analog. United States Patent Application Publication No. 2016/0186176 A1 describes various RNAi reagents, e.g., Dicer substrate siRNA (DsiRNA) reagents, including first and second nucleic acid strands and duplexes. The reagents are nucleic acids or modified nucleic acids or nucleic acid analogs. Exemplary DsiRNAs, in reference to their designation in United States Patent Application Publication No. 2016/0186176 A1, include: βc-284, βc-288, βc-639, βc-830, βc-893, βc-894, βc-895, βc-900, βc-1306, βc-1310, βc-1314, βc-1541, βc-1545, βc-1566, βc-1567, βc-1568, βc-1569, βc-1652, βc-1662, βc-1667, βc-1681, βc-1682, βc-1683, βc-1820, βc-2097, βc-2144, βc-2151, βc-2277, βc-2350, βc-2442, βc-2445, βc-2517, βc-2521, βc-2525, βc-2611, βc-2612, βc-2620, βc-3111, βc-3195, βc-3389, βc-3393, βc-3399, βc-3500, βc-3534, βc-3589, βc-3591, βc-3653, βc-3659, βc-3708, βc-3712, βc-240, βc-244, βc-253, βc-259, βc-264, βc-496, βc-516, βc-540, βc-582, βc-686, βc-692, βc-697, βc-707, βc-753, βc-870, βc-889, βc-1060, βc-1070, βc-1154, βc-1180, βc-1412, βc-1418, βc-1579, βc-1620, βc-1816, βc-2282. βc-3203, βc-3333, βc-3354, βc-3426, βc-3431, βc-3605, βc-3615, βc-3674, βc-3686, βc-3691, βc-m1354, βc-m1515, βc-m1763, βc-m2568, βc-m2806, βc-m3092, βc-m3207, βc-m3444, βc-m3449, or βc-m3533, in one aspect they include βc-1545, βc-1683, βc-2097, βc-2277, βc-2612, βc-3111, βc-3195, βc-3389, βc-3393, βc-3399, βc-3534, βc-3653, βc-3659. βc-3708, βc-3712, βc-253, βc-259, βc-686, βc-692, βc-697, βc-870, βc-889, βc-1154, βc-1180, βc-1412, βc-2282, βc-3203, βc-3431, βc-m1763, βc-m2806, βc-m3207, or βc-m3533, and in one aspect, they are e.g., βc-1545, βc-1683, βc-3195, βc-3389, βc-3393, βc-3399, βc-3534, βc-3659. βc-3712, βc-253, or βc-3203, and in a further aspect, they include DsiRNAs of Table 18 of US 2016/0186176 A1, as follows:

```
                                           (SEQ ID NO: 2)
5'-CAGGGATTTTCTCAGTCCTTCACTCAA-3';

(SEQ ID NO: 3)
5'-TGATGGACAGTATGCAATGACTCGAGC-3';

(SEQ ID NO: 4)
5'-TGCTGCTCATCCCACTAATGTCCAGCG-3';

(SEQ ID NO: 5)
5'-GCAGAATACAAATGATGTAGAAACAGC-3';

(SEQ ID NO: 6)
5'-CACCTGTGCAGCTGGAATTCTTTCTAA-3';

(SEQ ID NO: 7)
5'-TGAACTTGCTCAGGACAAGGAAGCTGC-3';

(SEQ ID NO: 8)
5'-TAGCCTTGCTTGTTAAATTTTTTTTTT-3';

(SEQ ID NO: 9)
5'-GTAGAACACTAATTCATAATCACTCTA-3';

(SEQ ID NO: 10)
5'-TAAATCAGTAAGAGGTGTTATTTGGAA-3';

(SEQ ID NO: 11)
5'-AAAAATGGTTCAGAATTAAACTTTTAA-3';

(SEQ ID NO: 12)
5'-CAGGGATTTTCTCAGTCCTTC-3';

(SEQ ID NO: 13)
5'-TGATGGACAGTATGCAATGAC-3';

(SEQ ID NO: 14)
5'-TGCTGCTCATCCCACTAATGT-3';

(SEQ ID NO: 15)
5'-GCAGAATACAAATGATGTAGA-3';

(SEQ ID NO: 16)
5'-CACCTGTGCAGCTGGAATTCT-3';

(SEQ ID NO: 17)
5'-TGAACTTGCTCAGGACAAGGA-3';

(SEQ ID NO: 18)
5'-TAGCCTTGCTTGTTAAATTTT-3';

(SEQ ID NO: 19)
5'-GTAGAACACTAATTCATAATC-3';

(SEQ ID NO: 20)
5'-TAAATCAGTAAGAGGTGTTAT-3';
and
                                           (SEQ ID NO: 21)
5'-AAAAATGGTTCAGAATTAAAC-3',
``` or modified nucleic acids or nucleic acid analogs of any of the preceding, such as 2'-O-methyl-modified versions thereof.

In aspects, antisense reagents also may be used to knock down β-catenin expression (see, e.g., U.S. Pat. No. 6,066,500 and Popov, V. B., et al., Second-generation antisense oligonucleotides against β-catenin protect mice against diet-induced hepatic steatosis and hepatic and peripheral insulin resistance, *FASEB J.* 2016; 30 (3): 1207-1217).

In aspects, inhibitors, such as small molecule inhibitors of the activity of β-catenin also may be used to decrease β-catenin activity and thereby treat *porphyria*. In aspects, such inhibitors inhibit Wnt/β-catenin/TCF transcriptional activation activity. In one aspect the inhibitor is ICG001 or an isomer, stereoisomer, or enantiomer thereof, including pure or racemic mixtures of stereoisomers of ICG001.

ICG001 and related compounds are described in U.S. Pat. No. 8,293,743. PRI 724 is an enantiomer of ICG001, as seen in FIG. 2.

In further aspects, inhibitors of the activity of β-catenin include porcupine (PORCN) inhibitors, which also may be used to decrease β-catenin activity and thereby treat *porphyria*. PORCN is required for the synthesis of Wnt ligands, which participate in the Wnt signaling pathway. PORCN is a membrane-bound O-acyltransferase located in the endoplasmic reticulum of cells and mediates the palmitolyation/acylation of serine/threonine residues of the Wnt ligand. Successful palmitolyation/acylation causes the secretion of Wnt ligands and activates Wnt-mediated signaling through the accumulation of β-catenin in the cytoplasm of the cell. β-catenin is eventually translocated to the nucleus, where its accumulation drives the downstream regulation of gene expression. The dysregulation of this Wnt signaling pathway can lead to tumor cell proliferation and injury. The administration of PORCN inhibitors prevents the palmitolyation/acylation of the Wnt ligand, which prevents β-catenin accumulation. Without the Wnt ligand, β-catenin is phosphorylated in the cell cytoplasm and is degraded. Thus, lack of accumulation of β-catenin in the nucleus of the cell disrupts the Wnt signaling pathway.

Figure 3A:
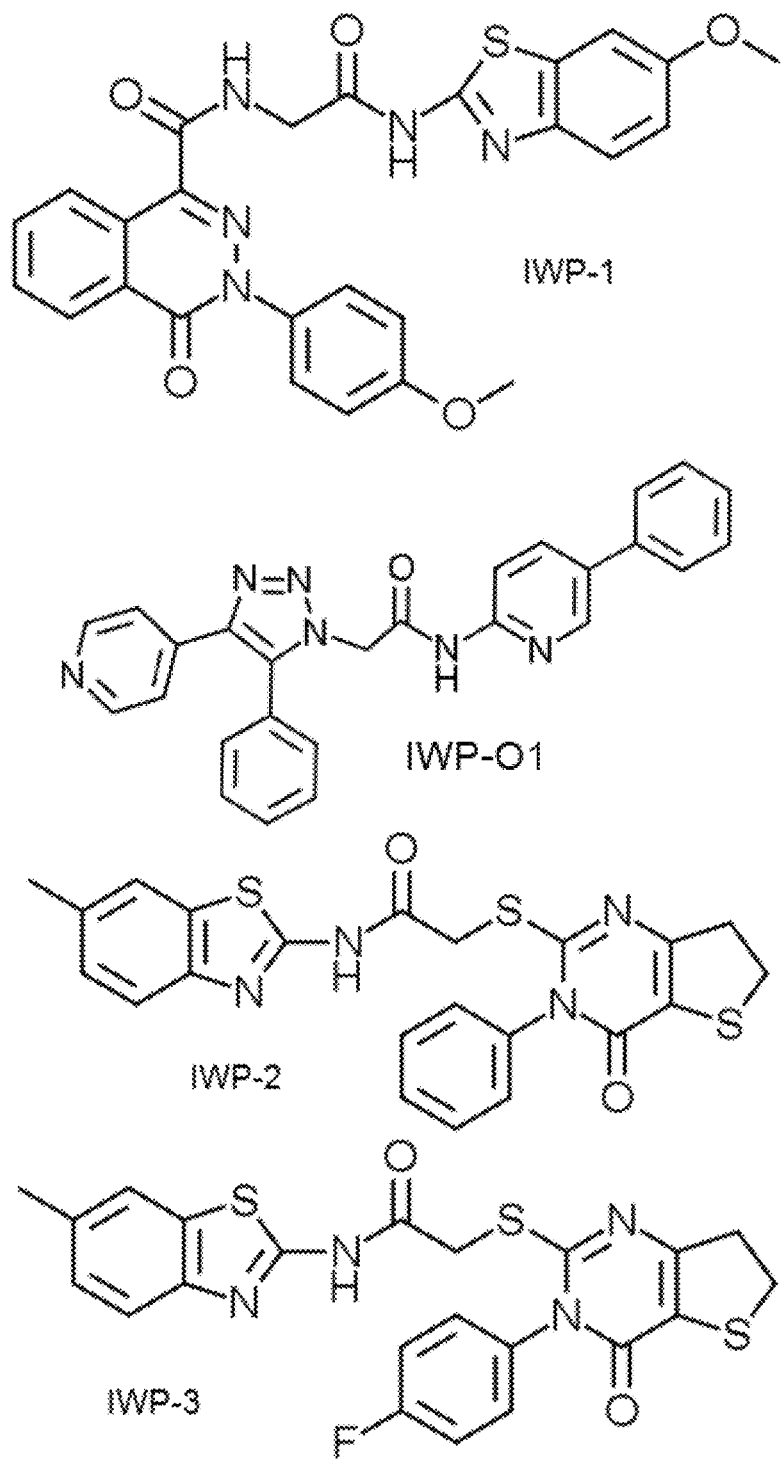
Figure 3B:
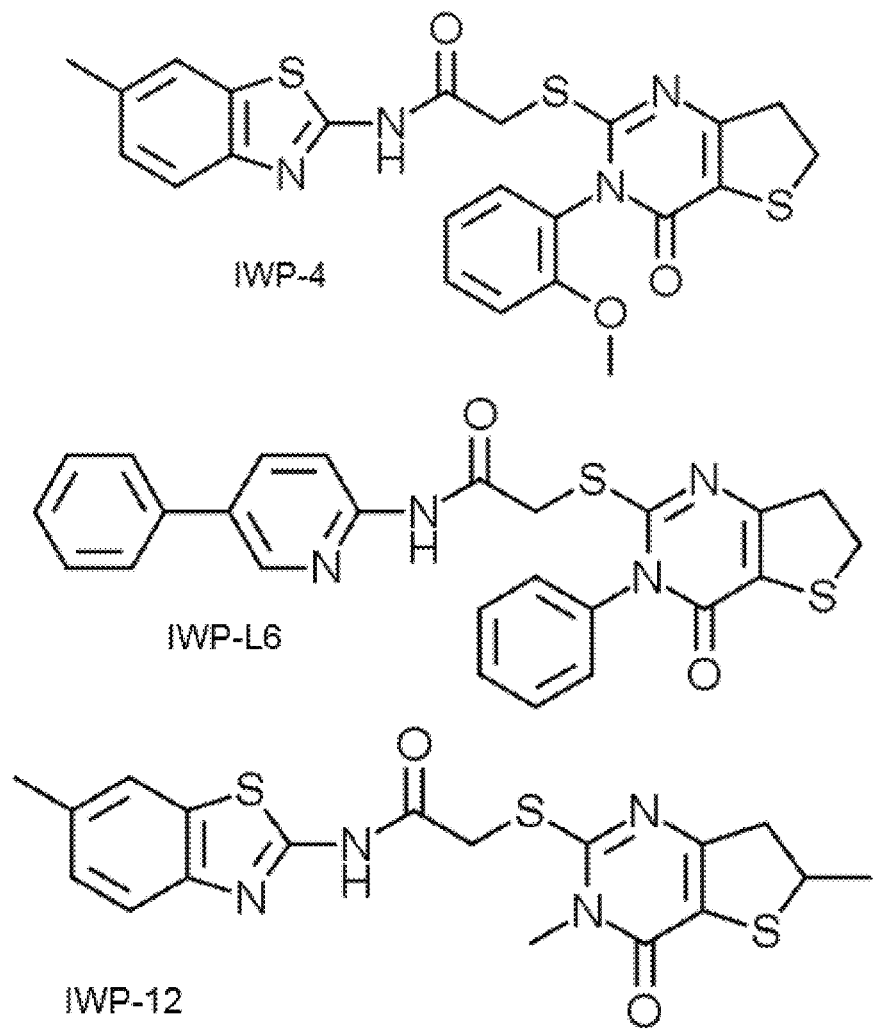

A number of PORCN inhibitors (FIGS. 3A-3C) are known, including, without limitation: LGK974 (see, e.g., U.S. Pat. No. 8,546,396 B2 and Liu J, et al., Targeting Wnt-driven cancer through the inhibition of Porcupine by LGK974. *Proc. Natl. Acad. Sci. U.S.A.* 2013; 110 (50): 20224-20229); CGX1321 (see, e.g., International Patent Application Publication No. WO 2014/165232 A1, United States Patent Application Publication No. 2018/0153884 A1, U.S. Pat. No. 10,238,652 B2, and Jiang, J., et al. A novel porcupine inhibitor blocks WNT pathways and attenuates cardiac hypertrophy. *Biochim. Biophys. Acta, Mol. Basis Dis.* 2018; 1864 (10): 3459-3467); Wnt-C59 (see, e.g., U.S. Pat. No. 8,546,396 B2 and Proffitt, K. D., et al. Pharmacological Inhibition of the Wnt Acyltransferase PORCN Prevents Growth of WNT-Driven Mammary Cancer. *Cancer Res.* 2013; 73 (2): 502-507); ETC-1922159 (ETC-159) (see, e.g., U.S. Pat. No. 9,926,320 B2 and Madan, B., et al. Wnt addiction of genetically defined cancers reversed by PORCN inhibition. *Oncogene* 2016; 35:2197-2207); IWP2 and IWP1 (see, e.g., U.S. Pat. No. 9,783,550 B2 and Chen, B., et al. Small molecule-mediated disruption of Wnt-dependent signaling in tissue regeneration and cancer. *Nat. Chem. Biol.* 2009; 5 (2): 100-107); IWP-O1 (see, e.g., You, L., et al. Development of a triazole class of highly potent Poren inhibitors. *Bioorg. Med. Chem. Lett.* 2016; 26 (24): 5891-5895); RXC004 (see, e.g., U.S. Pat. No. 10,202,375 B2, U.S. Pat. No. 10,047,079 B2, and Bhamra, I., et al. Novel Porcupine (PORCN) inhibitor RXC004: Evaluation in models of RNF43 loss of function cancers. *J. Clin. Oncol.* 2017; 35 (15)); IPW-3 and IPW-4 (see, e.g., U.S. Pat. No. 9,783, 550 B2); GNF-6231 (see, e.g., U.S. Pat. No. 8,546,396 B2, and Cheng, D., et al. Discovery of Pyridinyl Acetamide Derivatives as Potent, Selective, and Orally Bioavailable Porcupine Inhibitors. *ACS Med. Chem. Lett.* 2016; 7:676-680); IWP-12 (see, e.g., U.S. Pat. No. 9,783,550 B2 and Wang. X., et al. The Development of Highly Potent Inhibitors of for Porcupine. *J. Med. Chem.* 2013; 56 (6): 2700-2704); and IWP-L6 (see, e.g., U.S. Pat. No. 9,783,550 B2 and Wang, X. et al. *J. Med. Chem.* 2013; 56 (6): 2700-2704). International Patent Application Publication No. WO 2014/165232 A1 describes a number of PORCN inhibitors.

Reagents, such as siRNA, DsiRNA, antisense reagents, and small molecules such as PRI-724 or ICG001, can be targeted to a target organ, such as the liver, by conjugation to a targeting moiety, such as N-acetyl galactosamine (GalNAc) by a hydrolyzable bond such as an ester, which is cleaved in vivo, releasing the reagent locally. GalNAc, e.g., triantennary GalNAc, has been used to target oligonucleotides to the liver (Prakash, T. P., et al. Targeted delivery of antisense oligonucleotides to hepatocytes using triantennary N-acetyl galactosamine improves potency 10-fold in mice, *Nucl. Acids Res.* 2014; 42 (13): 8796-8807).

We have shown that mice lacking β-catenin in hepatocytes and cholangiocytes (albumin-cre β-catenin knockout (KO) mice; KO1) had fewer A6-positive atypical ductular cells in response to DDC (Apte, U., et al. Wnt/beta-catenin signaling mediates oval cell response in rodents. *Hepatology* 2008; 47:288-295), which was not due to decreased levels of total liver bile acids (Thompson, M. D., et al. Beta-catenin regulation of farnesoid X receptor signaling and bile acid metabolism during murine cholestasis. *Hepatology* 2018; 67 (3): 955-971). In the current study, we demonstrate that mice lacking Wnt/β-catenin pathway components or following pharmacologic β-catenin inhibition exhibited less hepatic injury after DDC. This was due to a novel role of Wnt/β-catenin pathway in regulating heme biosynthesis, which resulted in lesser porphyrin accumulation, fewer protein aggregates, and lesser overall hepatic injury. Thus, inhibiting Wnt/β-catenin signaling may represent a potential therapeutic strategy for patients with hepatic *porphyria*.

Example 1

Materials and Methods

Animals. Male mice with β-catenin loxp+/+ or LRP5/6 loxp+/+ were backcrossed to Alb-Cre+/− (all in a C57BL6 background) to generate β-catenin KO mice (KO1) or LRP5/6 double KO mice (KO2) in hepatocytes and cholangiocytes. Littermates with floxed alleles but without Cre were used as respective wildtype controls (WT1, WT2). Mice were fed a diet containing 0.1% DDC (Bioserve, Frenchtown, NJ) at 2 months of age for 14 days, as described previously. On the 15th day animals were sacrificed. Blood samples were collected from the inferior vena cava and serum isolated for biochemical analysis. Portions of the liver were fixed in 10% formalin and processed for paraffin embedding; the remaining liver was frozen in liquid nitrogen and stored at −80° C.

Therapeutic intervention with β-catenin DsiRNA LNP. Two-month old male CD-1 mice were started on 0.1% DDC. Three days after starting diet, mice received either one intravenous (i.v.) injection of β-catenin Dicer-substrate siRNA (DsiRNA) formulated in a lipid nanoparticle (LNP) from Dicerna Pharmaceuticals (Watertown, MA) at 3 mg/kg, or scrambled (control) DsiRNA LNP i.v. at the same concentration. Mice were dosed weekly thereafter with either control or β-catenin DsiRNA until the time of sacrifice (day 31 after the start of DDC). Livers from the control and experimental groups were utilized for immunohistochemistry (IHC), Western blotting, and biochemical assays.

Serum Biochemistry. Serum biochemical measurements were performed by the University of Pittsburgh Department of Pathology Laboratory Support Services. Total bilirubin, direct bilirubin, alkaline phosphatase (ALP), aspartate aminotransferase (AST), and alanine aminotransferase (ALT) were measured in samples taken before sacrifice at multiple time points.

Immunohistochemistry. Tissues fixed in 10% formalin were embedded in paraffin, and 4-μm sections cut onto Superfrost Plus glass slides (Thermo Fisher Scientific, Pittsburgh, PA) were used for H&E, Sirius Red, or immunohistochemical analysis as described elsewhere 1. Primary antibodies used include-catenin (1:100, sc-7199), glutamine synthetase (GS; 1:50, sc-9067), cyclin D1 (1:50, sc-753), and CD45 (1:100, sc-53665) from Santa Cruz Biotechnology, Dallas, TX; Ki67 (1:100, RM9106-S) from Thermo Fisher Scientific; CD68 (1:100, MCA1957) and F4/80 (1:100, MCA497GA) from Bio-Rad, Hercules, CA; Neutrophil Elastase (1:1500, ab68672) and Sox9 (1:100, ab5535) from Abcam, Cambridge, MA; and EpCAM (1:10, Clone G8.8) from Developmental Studies Hybridoma Bank, University of Iowa. Apoptosis was determined using terminal deoxynucleotidyl transferase dUTP nick-end labeling (TUNEL) staining (ApopTag Peroxidase in Situ Apoptosis Detection Kit, Millipore, Temecula, CA, USA).

Quantification of Staining Polarized light images were taken with an Olympus Provis microscope. Each image was split into red, green and blue channels using ImageJ Fiji, among which the red channel was chosen since it has the best separation. Next the staining was isolated by using Threshold setting 25 for the upper level and 255 for the lower level. Then the percentage of the stained area to the total image was measured.

Bright field images of H&E staining were split into hematoxylin, eosin and DAB channels using ImageJ Fiji. The color of porphyrin plugs was shown in the DAB channel. Next, the color of porphyrin plugs was isolated by using Threshold setting 0 for the upper level and 75 for the lower level. Then the percentage of the porphyrin area to the total image was measured.

Protein Extraction and Western Blot Analysis. Approximately 20 mg of liver was dounce homogenized in a buffer containing 25 mM Tris-HCl (pH 7.6), 150 mM NaCl, 1% Nonidet P-40, 1% sodium deoxycholate, 0.1% SDS (RIPA buffer) supplemented with protease inhibitor as described previously (Ajioka, R. S., et al. Biosynthesis of heme in mammals. *Biochim. Biophys. Acta* 2006; 1763:723-736). Protein assays were performed using bicinchoninic acid protein assay. Equal amounts of protein (10-50 μg) were resolved on Tris-HCl precast gels (Bio-Rad) by SDS-PAGE analysis using the Mini-PROTEAN 3 Electrophoresis Module Assembly (Bio-Rad). The resolved proteins were transferred to polyvinylidene difluoride membranes, followed by immunoblotting and visualization by enhanced chemiluminescence. The primary antibodies used were mouse antibody to β-catenin (1:1000, BD610154, BD Biosciences, San Jose, CA); total YAP (1:1000, 4912), Phospho-YAP Ser127 (1:1000, 4911), CHOP (1:2000, 2895), and IRE1α (1:2000, 3294) from Cell Signaling Technology, Los Angeles, CA; cyclin D1 (1:200, RB-9041-PO) from Thermo Fisher Scientific; GAPDH (1:400, sc-25778), GS (1:1000, sc-74430), ferrochelatase (1:100, sc-377377), ubiquitin (Ub; 1:2000, sc-8017), and lamin A/C (1:2000, sc-37624) from Santa Cruz; hydroxymethylbilane synthase (HMBS; 1:500, MBS9407926) from MyBioSource, San Diego, CA; Cyp3a1 (1:2000, ab22724), GST mu (1:2000, ab53942), and lamin B1 (1:2000, ab16048) from Abcam; aminolevulinic acid synthase (ALA-S; 1:1000, NB100-56415) from Novus Biologicals, Littleton, CO; aminolevulinic acid dehydratase (ALA-D; 1:1000, AV41657) from Sigma; and keratin 8 (1:2000, Troma) and keratin 18 (1:2000, Ab-46683) from Developmental Studies Hybridoma Bank. Horseradish peroxidase conjugated secondary antibodies were purchased from Millipore (Billerica, MA).

Porphyrin measurement from total liver homogenate. Porphyrin was measured in the liver lysate in the form of total fluorescent porphyrin content (including Uro, Copro, PP-IX, and NMP) utilizing the intrinsic fluorescence of the demetallated porphyrins. Briefly, 2 μl of the lysate was added to 200 μl of 1:1 mixture of ethanol: perchloric acid (0.9 N). The fluorescence of the resulting solution was measured in a Biotek Synergy HT 96-well plate reader using the filter sets 400/30 nm (excitation) and 590/35 nm (emission). The amount of total porphyrins was expressed as fluorescent intensity normalized to the protein content of the sample.

In-gel heme staining. Protein bound heme was detected utilizing a modification of a previously published method (Smith, A. G., et al. Drugs and the hepatic porphyrias. Clin. Haematol. 1980; 9:399-425). Briefly, frozen livers were homogenized in phosphate buffered saline (PBS) containing 1% Empigen BB. 5 mM EDTA, and supplemented with protease inhibitor cocktail. 100 μg of total protein was separated by reducing SDS-PAGE, or non-denaturing PAGE, in 4° C. at 60V, and the proteins were transferred to a PVDF membrane. After transfer the membrane was washed with PBS twice, and then visualized with enhanced chemiluminescence reagent and autoradiograph film.

Metabolomic analysis. Liver samples were homogenized in water (100 mg tissue in 500 uL water), and then a 200 uL aliquot of methanol: acetonitrile (v/v, 1:1) was added to 100 uL of liver homogenate. The mixture was vortexed twice for 1 min and centrifuged at 15,000 g for 20 minutes. One microliter of the supernatants from all samples was injected onto the ultra-performance liquid chromatography and quadrupole time-of-flight mass spectrometry (UPLC-QTOFMS) for analysis as described previously (Tephly, T. R., et al. Studies on the mechanism of experimental *porphyria* and ferrochelatase inhibition produced by 3,5-diethoxycarbonyl-1,4-dihydrocollidine. Int. J. Biochem. 1980; 12:993-998).

Ferrochelatase activity assay. Activity of ferrochelatase in control DsiRNA and β-catenin DsiRNA-treated livers after DDC was performed as previously described6. Briefly, mitochondria were isolated from mouse livers treated with DDC and either control or β-catenin DsiRNA. Mitochondrial membranes were isolated and suspended in 1.0% sodium cholate and 0.1 M KCl. The mixture was centrifuged to separate the solubilized enzyme from membrane fragments, and saturated ammonium sulfate added to the enzyme. After centrifugation and further fractionation by saturated ammonium sulfate, the resulting pellet was dissolved in 1% Triton X-100 and 0.5 M KCl and then applied to a sepharose column. Ferrochelatase was eluted from the column with 1% sodium cholate and 1.5 M KCl. Fractions exhibiting ferrochelatase activity were incubated with 0.1 mM porphyrin in 50 mM Tris acetate, pH 8.1, 5 mM dithiothreitol, 0.2 mM ferrous ammonium citrate, and 0.2% Triton X-100 at 37° C. in the dark for 30 minutes. The reaction was terminated by addition of 50 mM iodoacetamide, and the product quantitated with a spectrophotometer.

Measurement of liver bile acids. Liver total bile acids were measured using a total bile acids kit from Crystal Chem (Downers Grove, IL), as per the manufacturer's instructions. Briefly, frozen liver tissue was homogenized in 70% ethanol at room temperature and then incubated in tightly capped glass tubes at 50° C. for 2 hours. The homogenates were centrifuged at 6,000 g for 10 minutes to remove debris. Total bile acid levels were measured and concentrations determined using the calibration curve and mean change in absorbance value for each sample.

RNA isolation and real-time PCR. RNA was extracted from frozen livers using Trizol (Invitrogen). RNA was DNase-treated and equal microgram amounts of RNA from each sample were used to make individual cDNA samples with SuperScript III First-Strand Synthesis System for RT-PCR (Invitrogen). cDNA along with 1× Power SYBR-Green PCR Master Mix (Applied Biosystems) and the appropriate primers were used for each real-time PCR reaction. The Applied Biosystems StepOnePlus Real-Time PCR System was used for the analysis of the transcripts with the StepOne v2.1 software. The comparative ΔΔCT method was used for analysis of the data and all data is presented normalized to WT at baseline. GAPDH expression was used as the internal control.

cDNA arrays. Livers from control and β-catenin DsiRNA LNP treatment were harvested 31 days after the start of DDC and mRNA was isolated using TRIzol (Invitrogen, Carlsbad, CA). mRNA was then analyzed for NF-κB-regulated gene expression with a mouse NF-κB-regulated cDNA plate array (Signosis, Sunnyvale, CA) as per the manufacturer's instructions. Briefly, mRNA was reverse transcribed using a biotinlabeled NF-κB primer mix, mixed with hybridization buffer, and added to a plate containing 21 target genes. The plate was then incubated at 450C overnight, washed the next day, blocked, and developed with substrate. The plate was read on a BioTek HT (BioTek, Winooski, VT) with no filter to detect luminescence. The data were normalized to control (WT) values and then plotted on a bar graph.

Transcription factor assay. Nuclear lysates from control and β-catenin DsiRNA LNP treated livers harvested 31 days after starting DDC were analyzed for NF-κB activity using the NF-κB p65 EZ-TFA Transcription Factor Assay (Millipore, Billerica, MA) as per the manufacturer's instructions. Briefly, 15 μg of each sample was added to the plate and incubated with blocking reagent for 1.5 hours at room temperature. The plate was washed, incubated with NF-κB antibody provided by the manufacturer, washed and incubated with rabbit secondary antibody, and then developed with substrate. The plate was read on a BioTek HT at an absorbance of 450 nm.

Characterization of the ALA-D promoter region. ChIPseq studies of RXRα, FXR, TCF4, HNF4α, LXR, PPAR, CAR, H4K5Ac (transcriptionally active chromatin), and H3K4Me3 (active promoter regions) were aligned with RNAseq reads to identify binding regions. Data is derived from a manuscript in preparation by Tian and Locker; the FXR analysis is described in Correia, M. A., et al. Cytochrome P450 regulation: the interplay between its heme and apoprotein moieties in synthesis, assembly, repair, and disposal. *Drug Metab. Rev.* 2011; 43:1-26.

Statistical Analysis. All experiments were performed with three or more animals, and representative data are presented. Quantification of positive cells and serum biochemistry measurements were compared for statistical analysis by Student's t-test (Graphpad 6.0), and P<0.05 or 0.01 was considered significant or extremely significant, respectively.

Figure 4C:
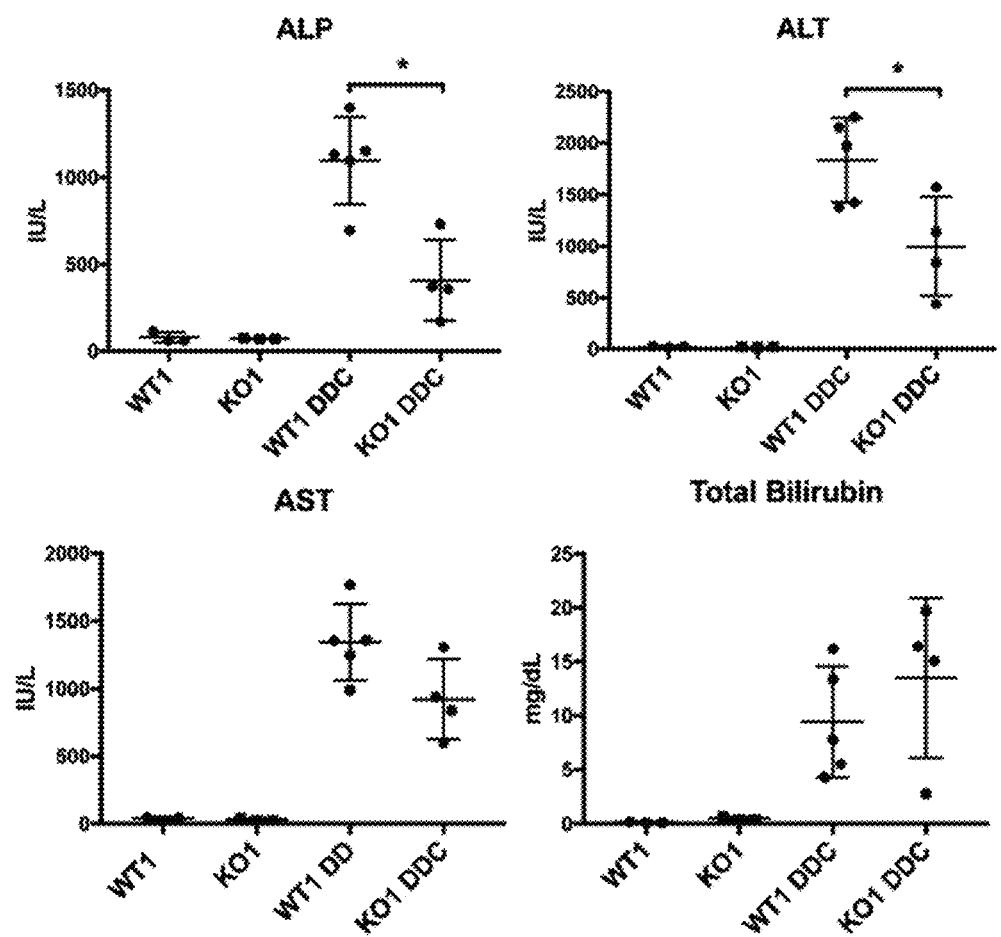

Results

β-catenin KO mice have less injury and inflammation than WT after 14 days of DDC. KO1 and WT1 littermates were fed DDC diet for 14 days and assessed for extent of injury (FIG. 4A). Gross examination revealed black-brown and enlarged WT1 livers, which is characteristic of DDC, while KO1 livers were smaller and normal looking (FIG. 4B). Likewise, KO1 showed decreased liver weight/body weight ratio. Notably, both hepatocellular and biliary injury are decreased in KO1, as shown by significantly lower serum alkaline phosphatase (ALP) and alanine aminotransferase (ALT) (FIG. 4C).

Figure 4D:
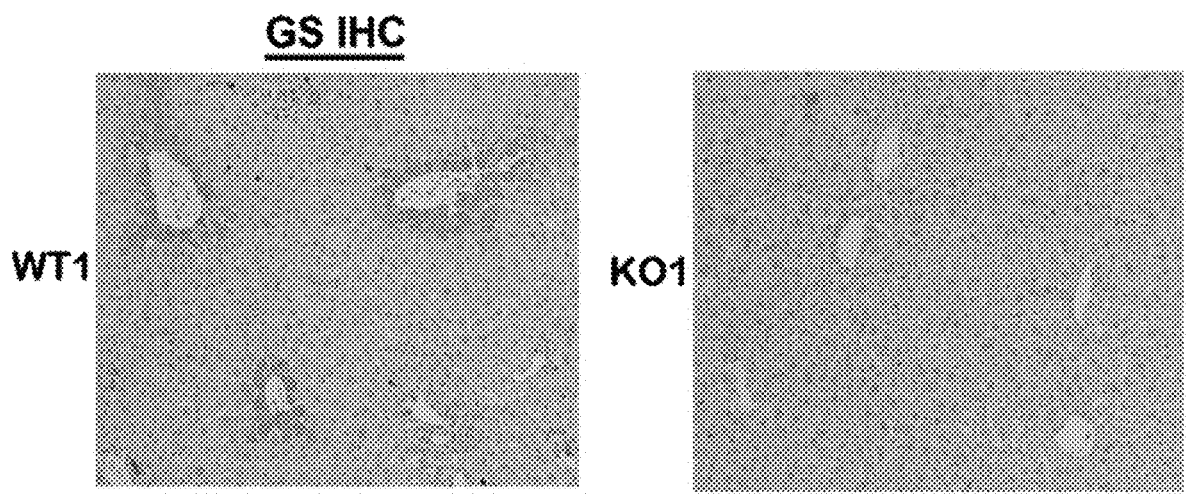
Figure 4E:
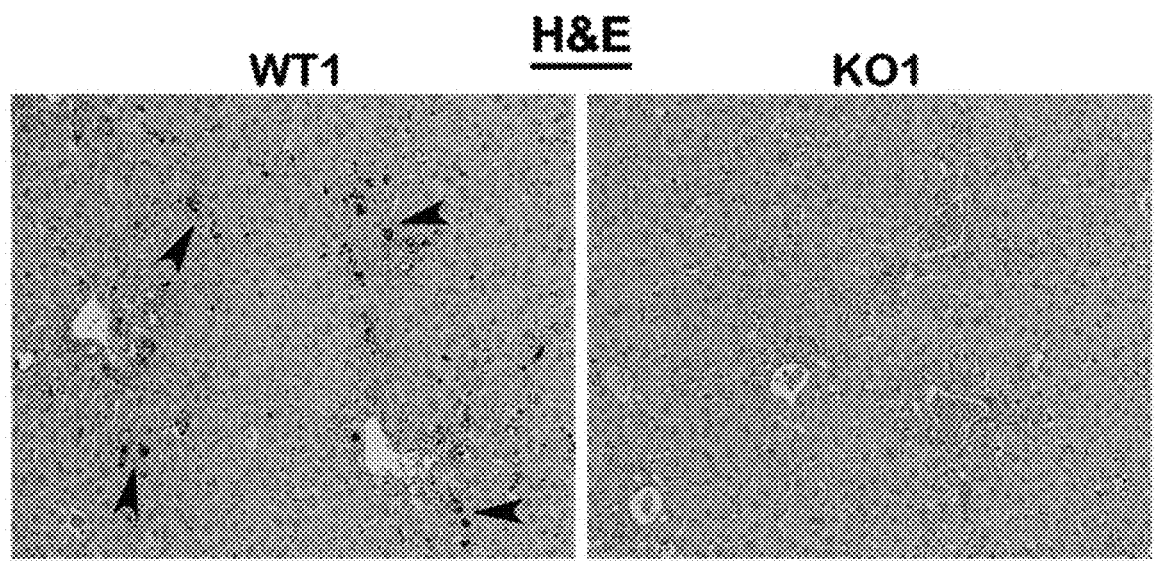
Figure 4F:
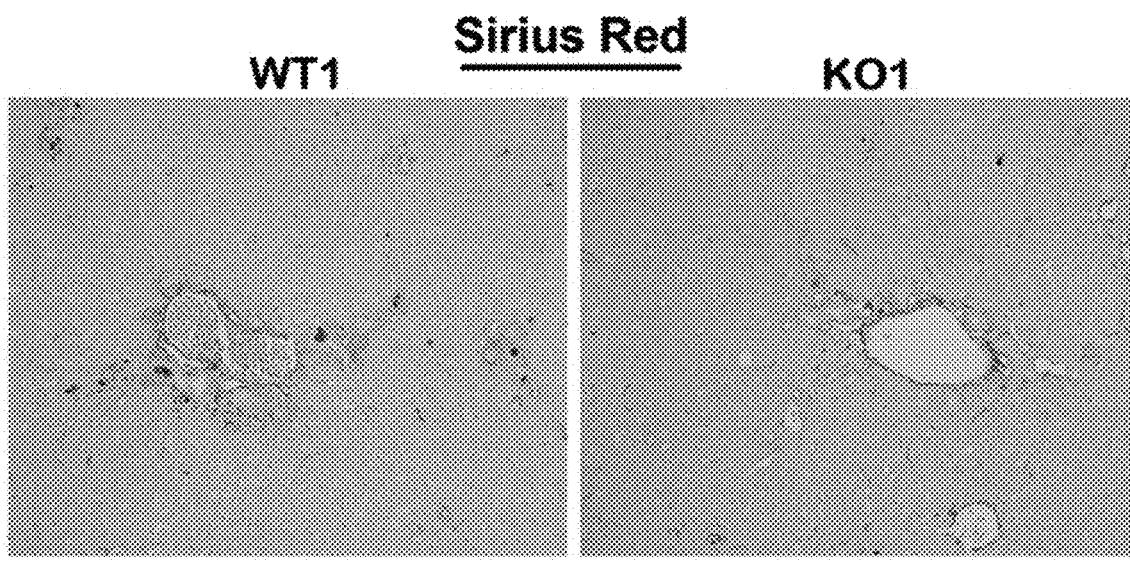
Figure 5A:
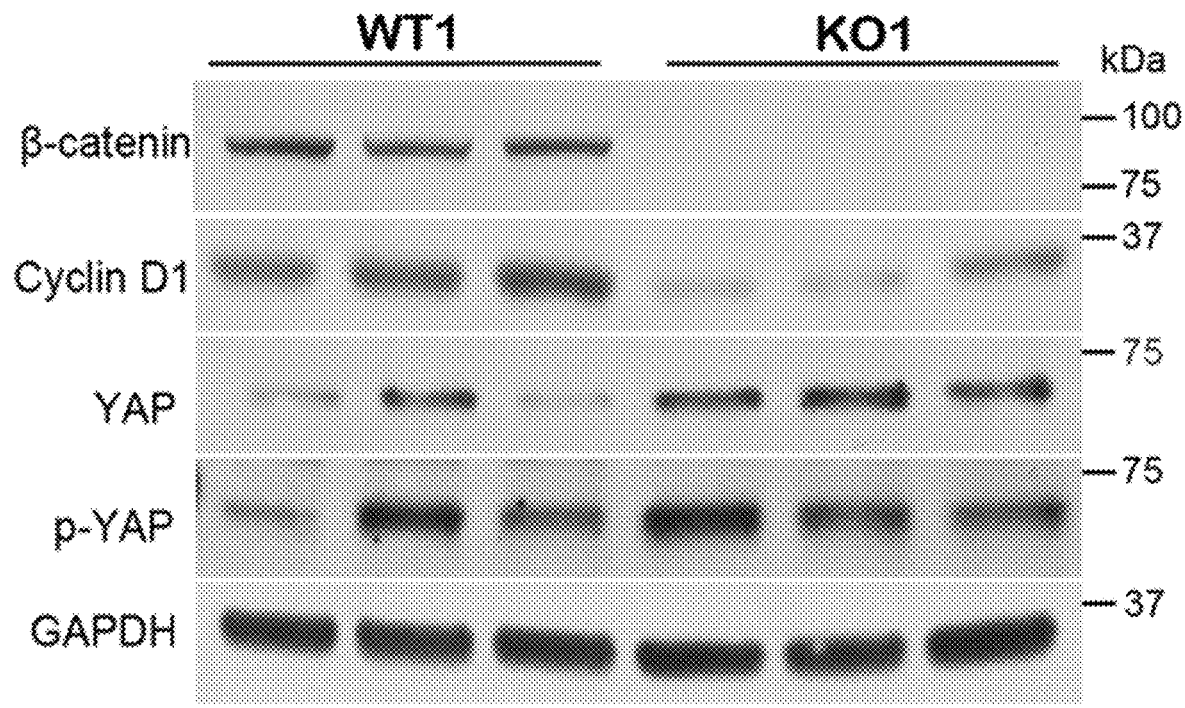
FIGS. 5A-5B: No change in biliary/cholangiocyte markers after β-catenin or Wnt signaling deletion and DDC.

Immunohistochemistry (IHC) for glutamine synthetase (GS), a transcriptional target of β-catenin, as well as WB for β-catenin, confirms β-catenin loss from hepatocytes in KO1 (FIG. 4D; FIG. 5A). Histology reveals KO1 livers have a noticeable decrease in dark brown pigmentation indicative of porphyrin accumulation compared to WT1 (FIG. 4E). However, fibrosis, as assessed by Sirius red, was equivalent in both genotypes (FIG. 4F).

Figure 6A:
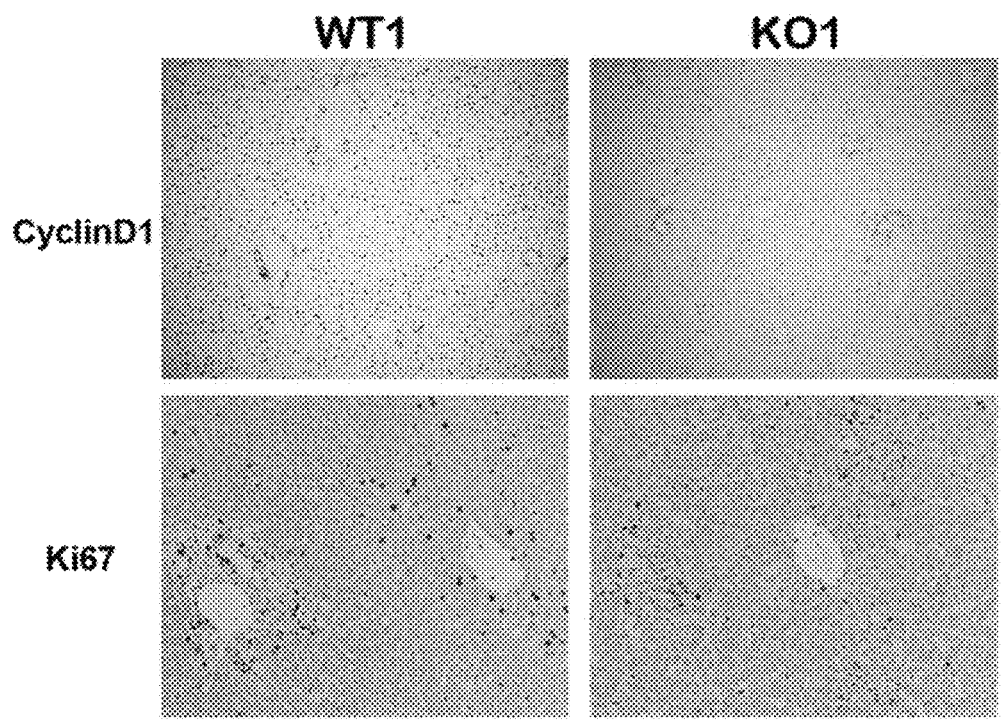
FIGS. 6A-6C: Proliferation and inflammation are decreased in KO1 livers after DDC.
Figure 6B:
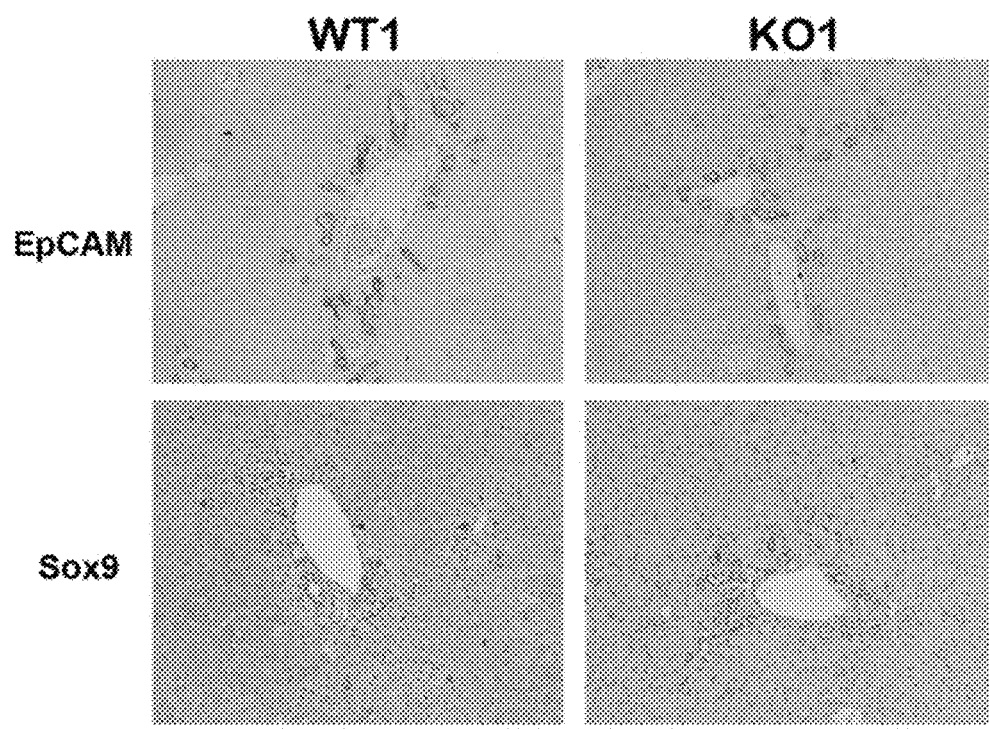

By IHC, we found significantly fewer cyclin D1 positive cells in KO1 livers due to loss of β-catenin, which was confirmed by WB (FIG. 5A; FIG. 6A). KI67 IHC also showed less hepatocyte proliferation in KO1 after DDC; however, cholangiocyte proliferation was still evident despite β-catenin loss (FIG. 6A). We next stained WT1 and KO1 livers with EpCAM and Sox9 and found equivalent ductular response in both phenotypes (FIG. 6B). Additionally, although total Yap protein was increased in KO1, the phosphorylated, inactive Yap increased as well, suggesting ductular mass is comparable in WT1 and KO1 (FIG. 5A).

Figure 6C:
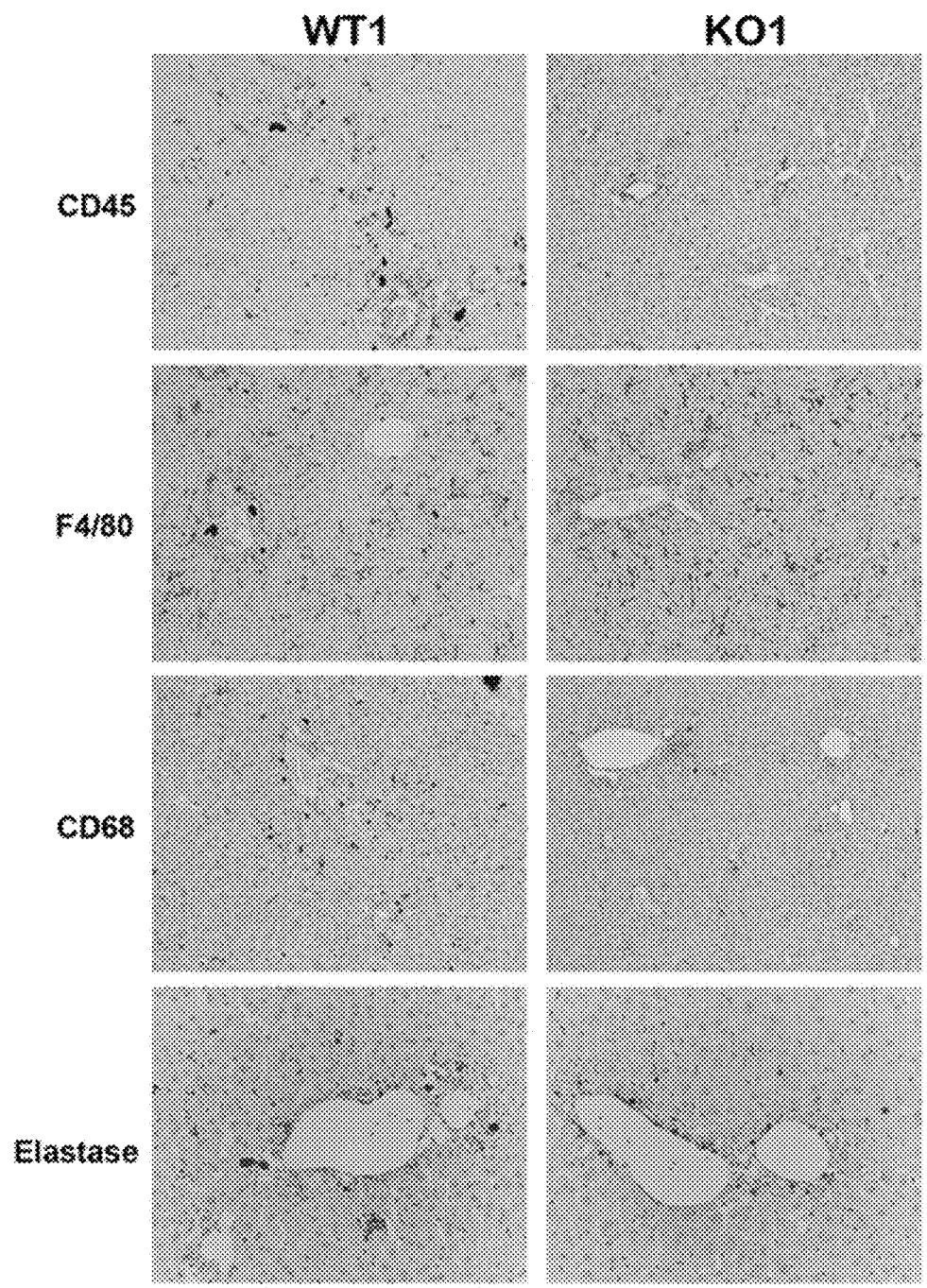

Finally, we examined hepatic inflammation in both groups after DDC. We observed a decrease in both CD68- and CD45-positive inflammatory cells in KO1 when compared to WT1 (FIG. 6C). There were also fewer elastase-positive neutrophils infiltrating the parenchymal tissue in periportal region. F4/80-stained macrophages were comparable in both groups. These findings suggest that on the whole, inflammation is less in KO1 compared to WT1 mice.

Figure 7A:
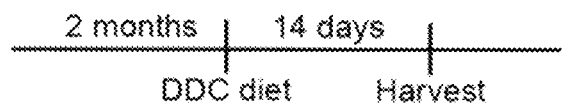
FIGS. 7A-7G: Alb-cre LRP5/6 KO have lesser injury than WT after DDC.
Figure 7B:
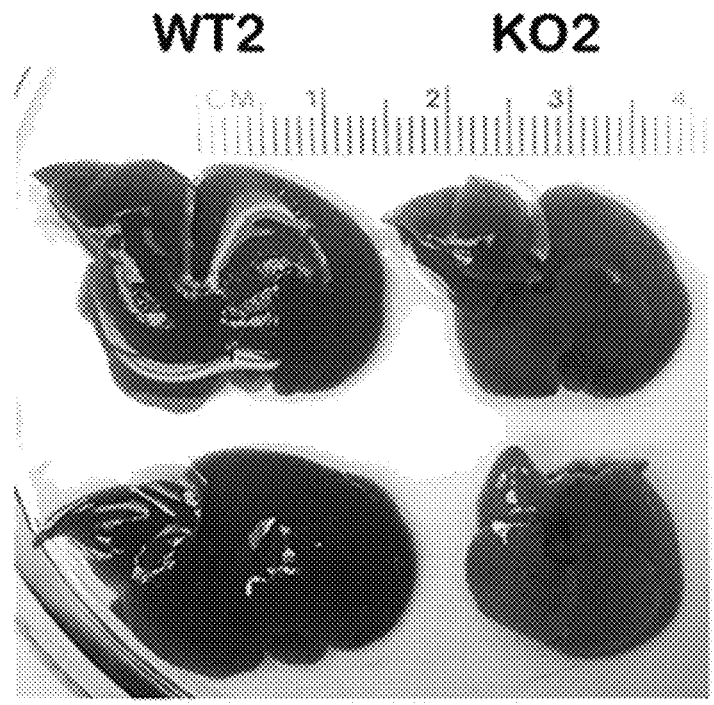
Figure 7C:
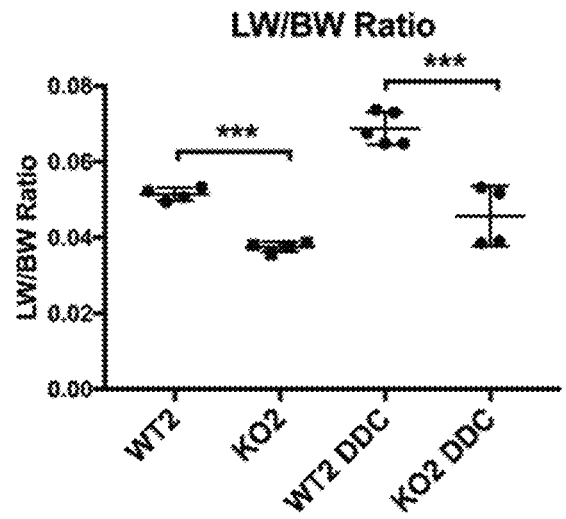
Figure 7D:
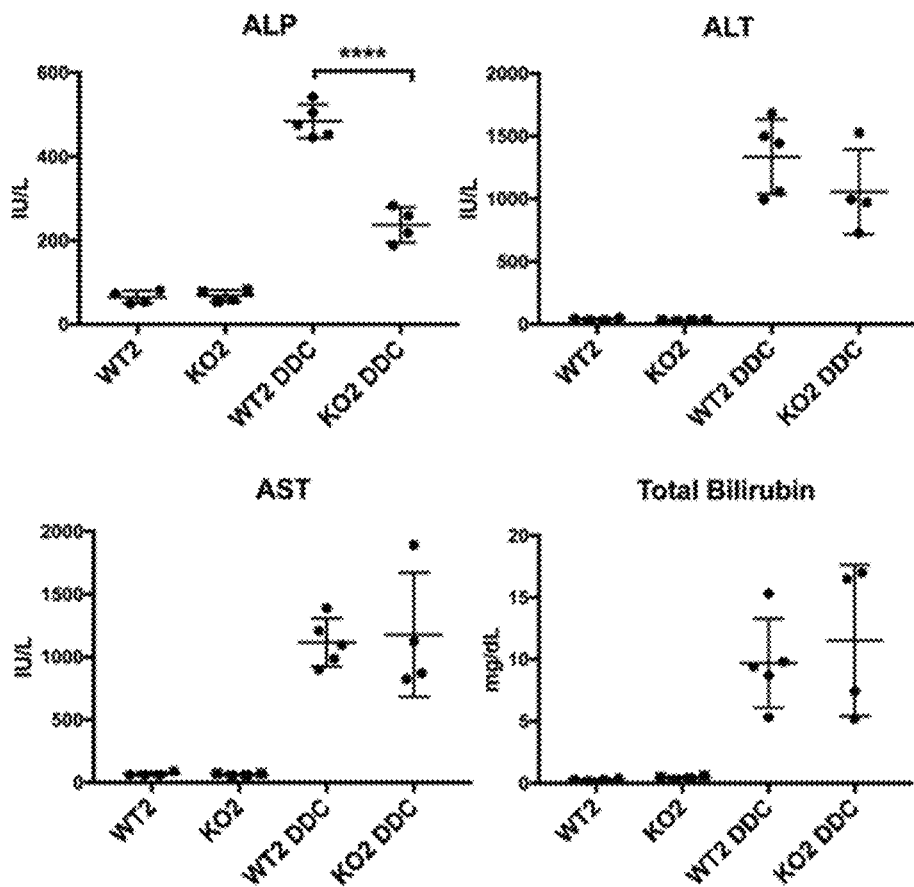

Mice lacking Wnt signaling show a similar protective phenotype as β-catenin KO after DDC feeding. Next, we assessed whether loss of upstream Wnt signaling also protects mice from DDC-induced liver injury. LRP5/6, a co-receptor for Wnt, is necessary to activate the canonical Wnt/β-catenin signaling pathway. LRP5/6-double KO mice (KO2) and littermate controls (WT2) were fed DDC for 14 days (FIG. 7A). KO2 mice had noticeably lighter-colored, smaller livers and decreased liver weight/body weight ratios compared with WT2 mice (FIG. 7B; FIG. 7C). In serum, ALP was significantly lower in KO2 than WT2 after DDC, with ALT approaching significance (FIG. 7D), indicating that like KO1, KO2 mice have less injury.

Figure 5B:
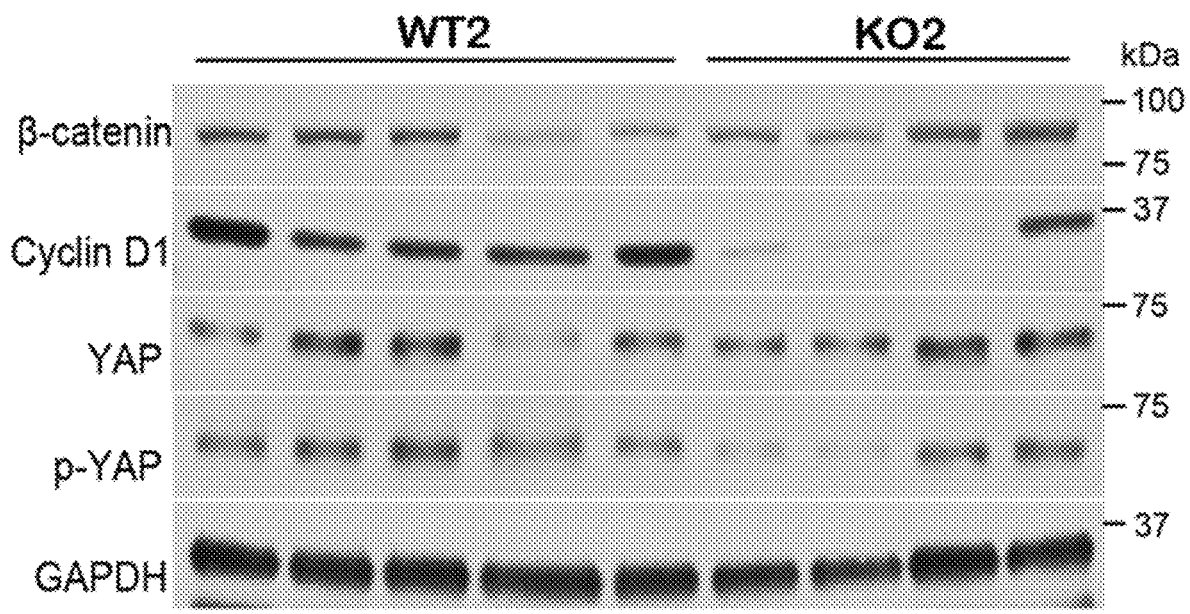
Figure 7E:
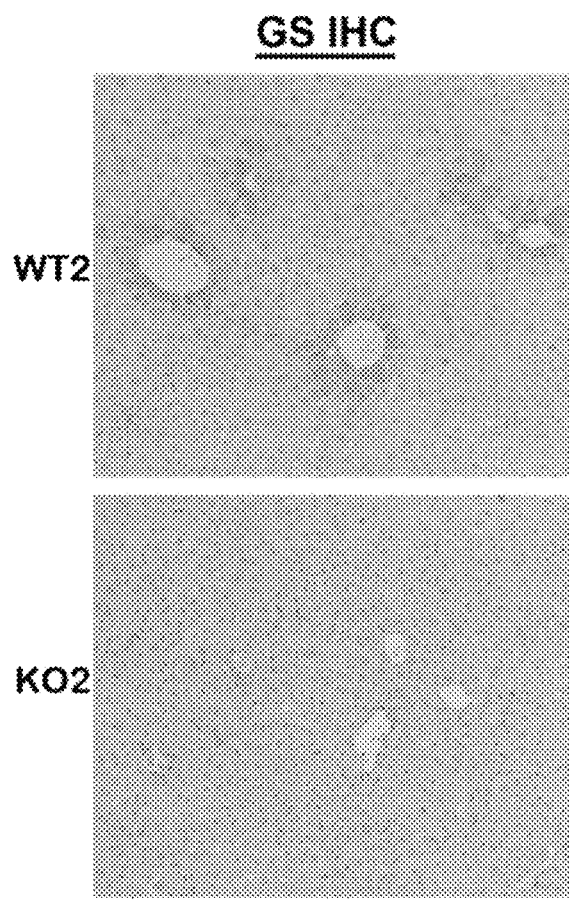
Figure 7F:
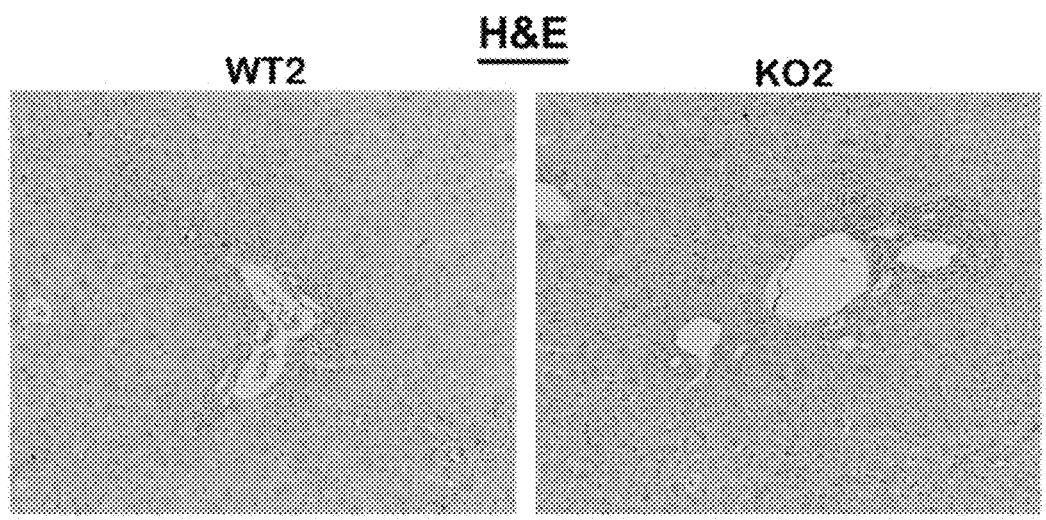
Figure 7G:
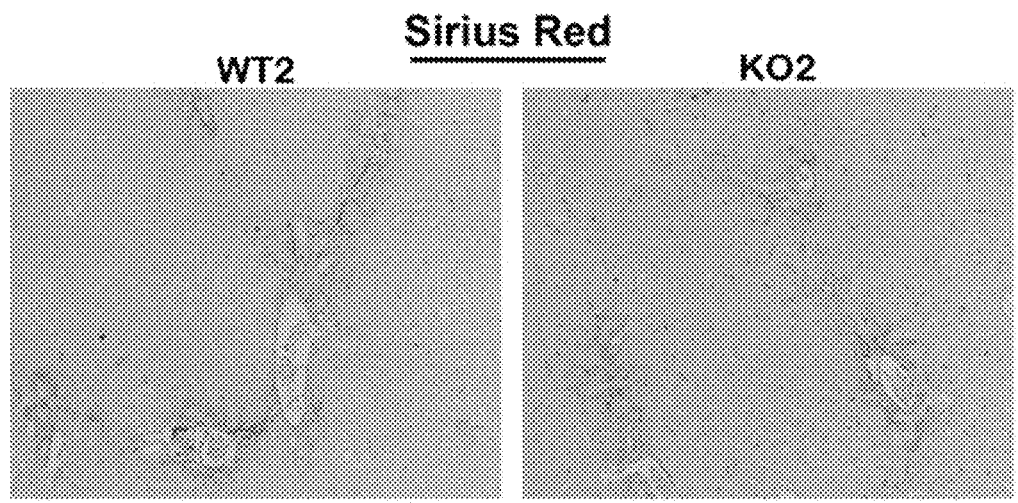
Figure 8A:
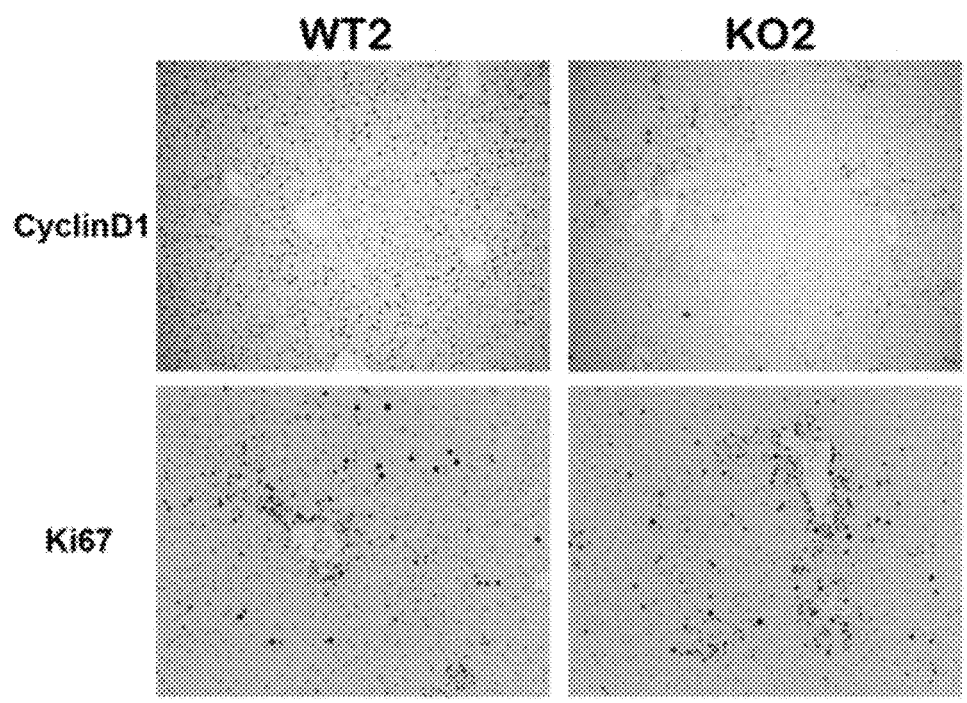
FIGS. 8A-8C: Like KO1, KO2 livers have decreased cyclin D1 expression and hepatic inflammation after DDC.
Figure 8B:
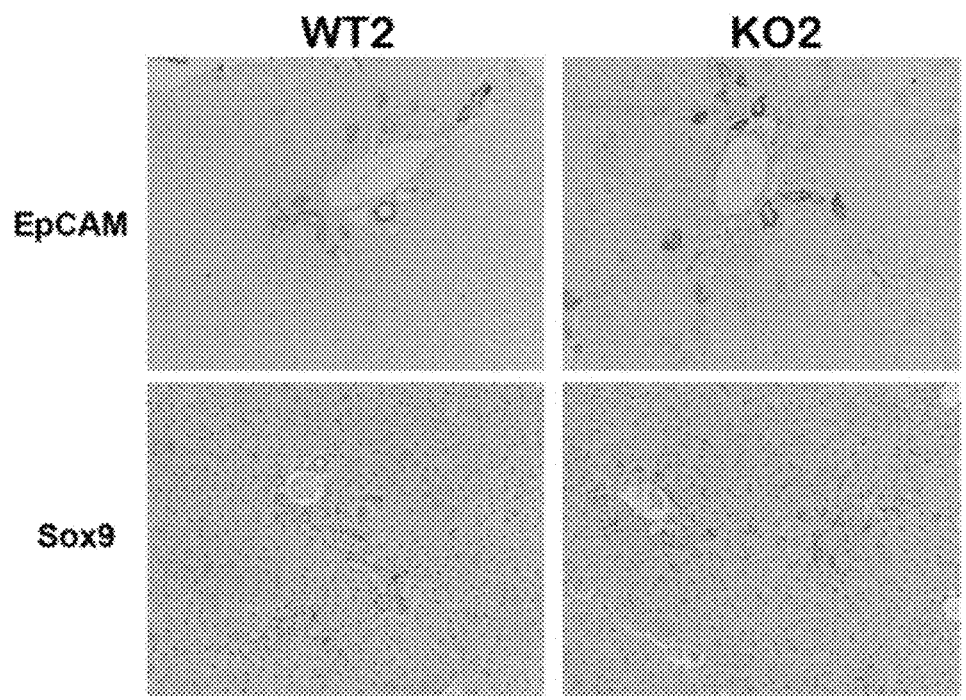
Figure 8C:
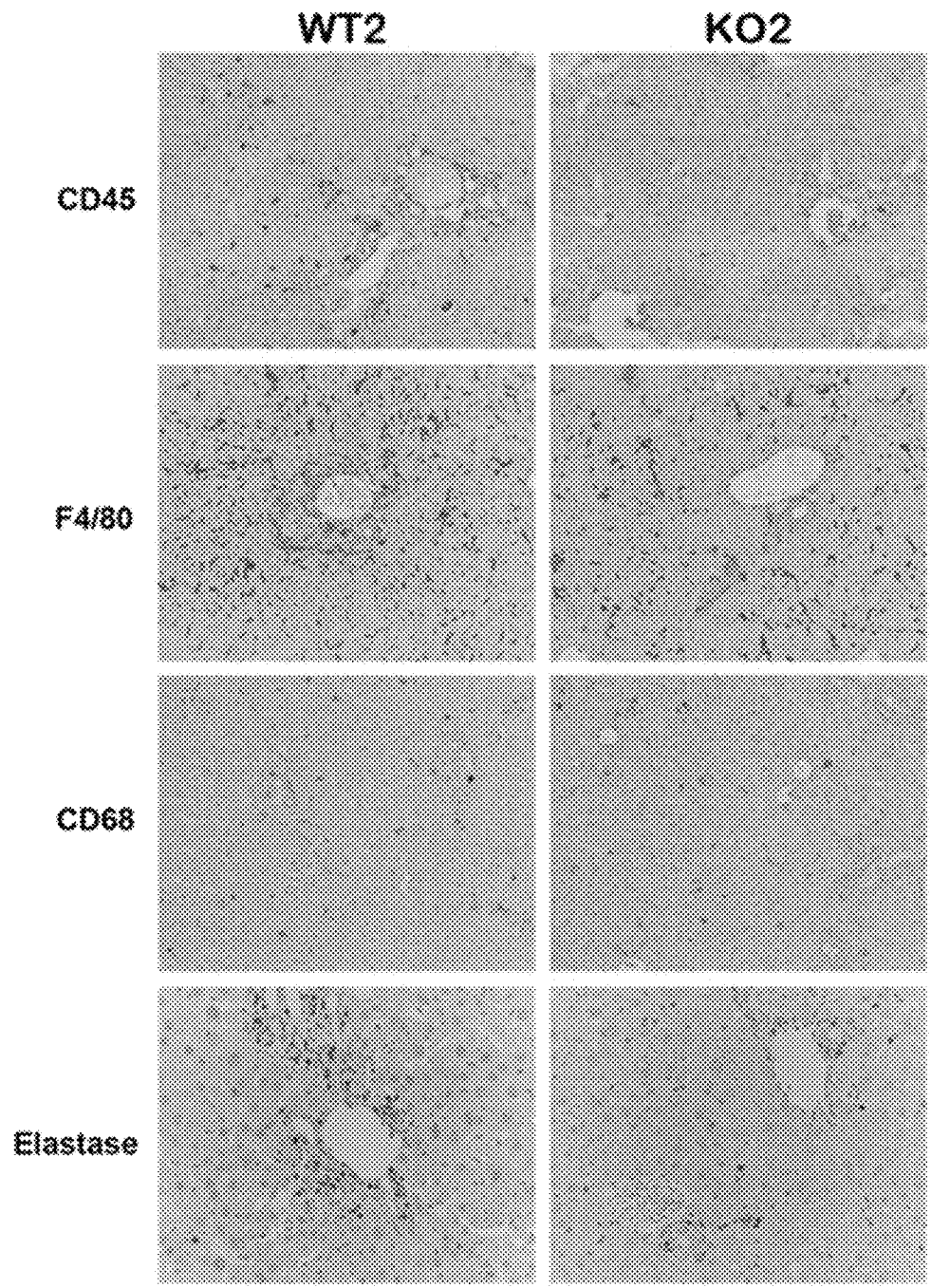

KO2 mice lack active β-catenin as confirmed by IHC for GS, despite the presence of hepatic β-catenin (FIG. 7E; FIG. 5B). H&E staining shows that like KO1, KO2 have decreased porphyrin accumulation compared to WT2, with comparable fibrosis (FIG. 7F; FIG. 7G). Interestingly, although cyclin D1 expression is dramatically decreased in KO2 after DDC, as demonstrated by both IHC and WB (FIG. 8A; FIG. 5B), Ki67-positive hepatocytes are still present in KO2 (FIG. 8A), suggesting Wnt/β-catenin-independent activation of proliferation. Similar to KO1, cholangiocyte proliferation is equivalent in WT2 and KO2, concomitant with equivalent Yap expression, indicating that β-catenin activation is not required for biliary repair after DDC (FIG. 5B; FIG. 8B). We also observed inflammatory markers CD45, F4/80, and elastase were decreased in KO2, while CD68 was equivalent in both genotypes (FIG. 8C). In summary, KO2 mice phenocopy key features of KO1 on DDC, including decreased biliary injury, inflammation, and porphyrin accumulation.

Exogenous inhibition of β-catenin using DsiRNA formulated in a lipid nanoparticle recapitulates the protective phenotype seen in β-catenin and LRP5/6 KO on DDC.

Figure 9D:
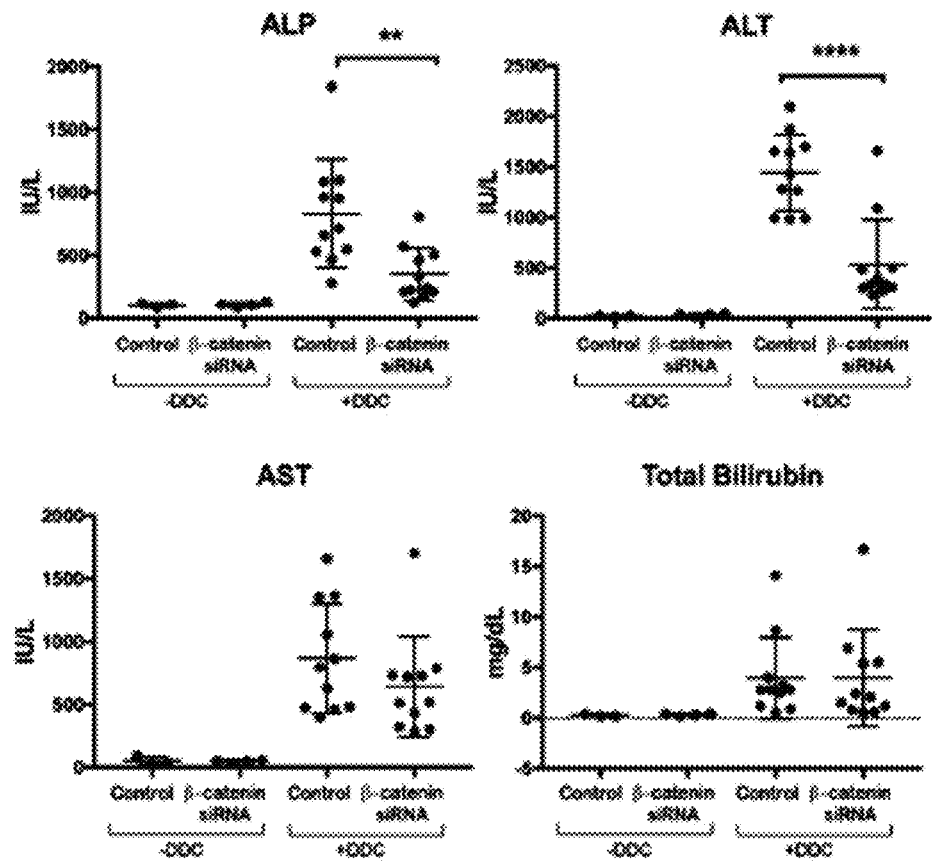
Figure 9E:
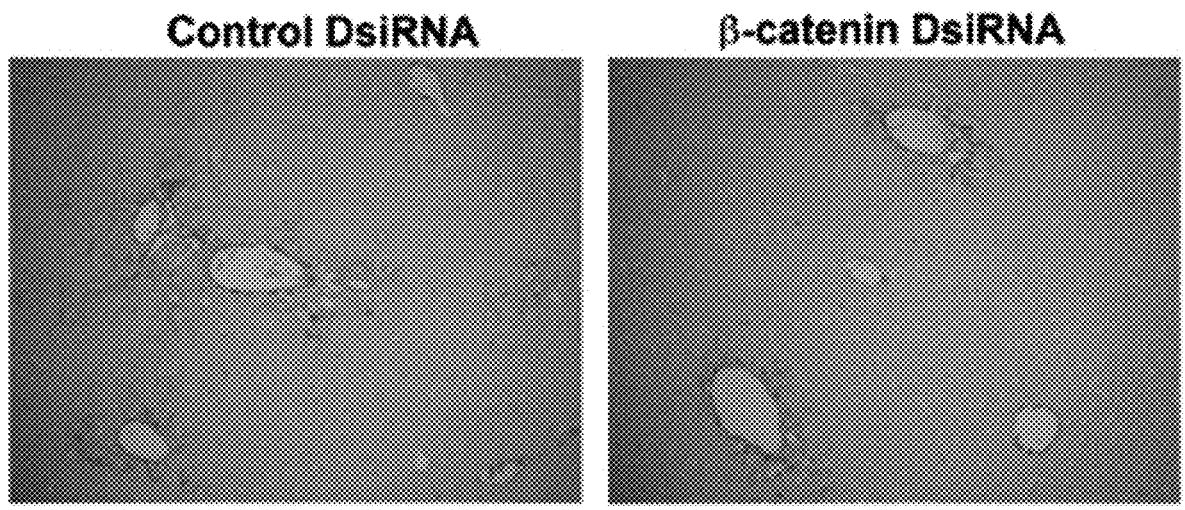
Figure 9F:
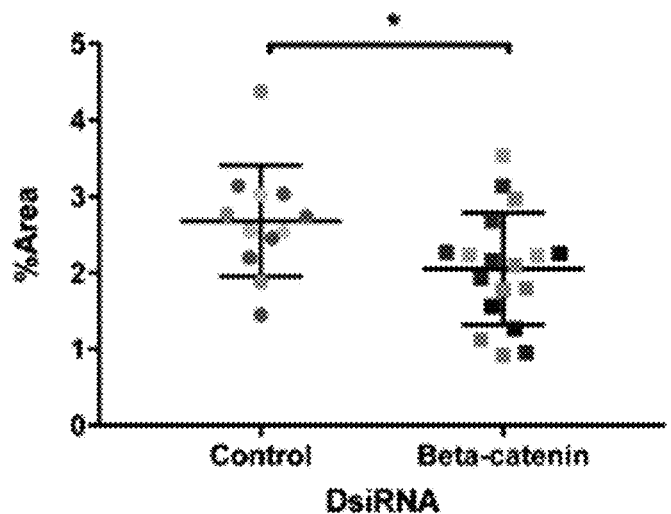
Figure 10A:
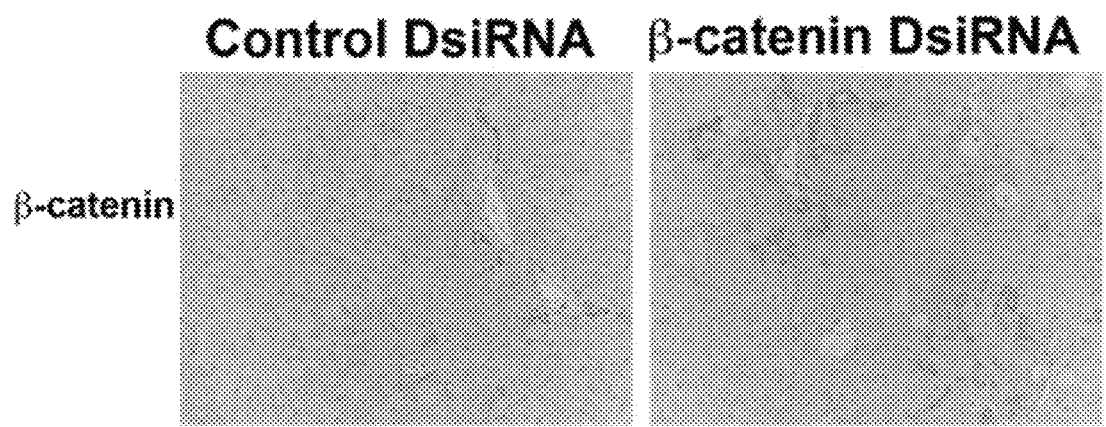
FIGS. 10A-10E: DsiRNA for β-catenin suppresses proliferation and inflammation after DDC.
Figure 10B:
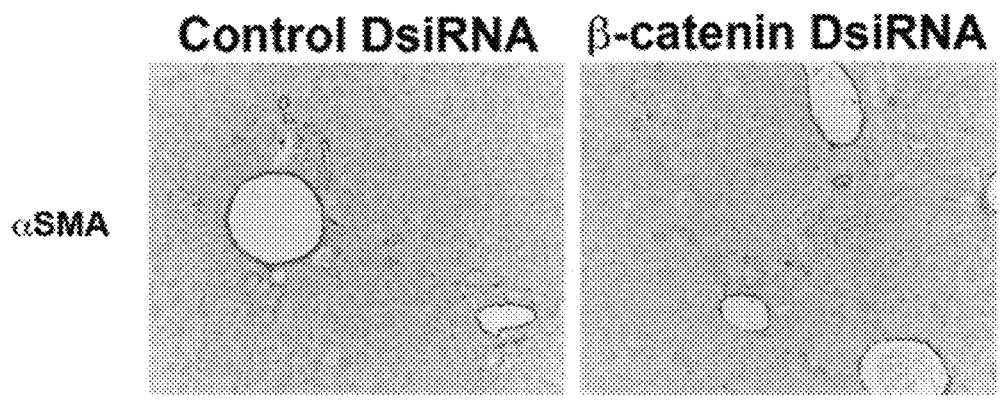
Figure 10C:
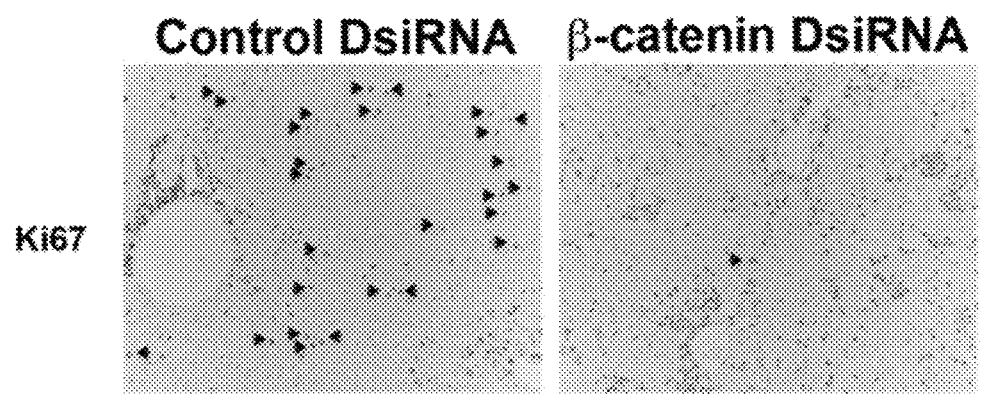
Figure 10D:
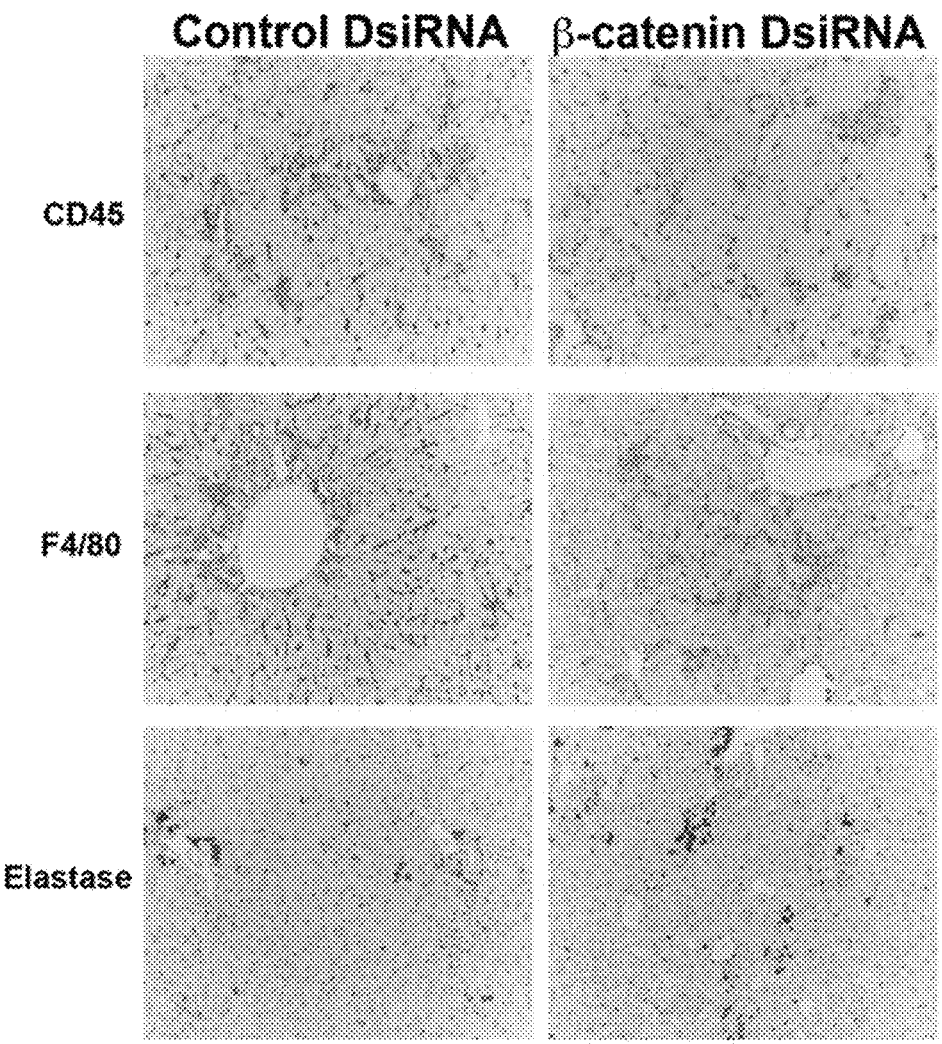

To address the relevance of therapeutic intervention, we next suppressed β-catenin exogenously in DDC-induced injury. We administered 3 mg/kg control or β-catenin DsiRNA formulated into a lipid nanoparticle (LNP) to mice once weekly beginning 3 days after starting DDC; the CD-1 strain was used in these studies to assure rigor and reproducibility (FIG. 9A). WB shows successful knockdown of β-catenin protein (FIG. 9B), and that the LNP preferentially targets the DsiRNA to hepatocytes (FIG. 10A). As in KO1 and KO2, livers of mice treated with β-catenin DsiRNA were notably smaller and lighter in color, with significantly decreased liver weight/body weight ratio (FIG. 9C). Both ALP and ALT were also significantly decreased after β-catenin DsiRNA administration (FIG. 9D), although overall injury was lesser compared to WT1 and comparable to WT2, likely due to strain-specific differences. The reduced injury after β-catenin DsiRNA treatment also resulted in a notable and significant decrease in fibrosis, as assessed by Sirius red staining and ImageJ quantification (FIG. 9E), although α-smooth muscle actin-positive myofibroblasts were evident in both control and β-catenin DsiRNA-treated livers (FIG. 10B). Mice treated with β-catenin DsiRNA also had decreased hepatocyte proliferation (FIG. 10C). CD45- and F4/80-positive cells were decreased after β-catenin DsiRNA, while elastase IHC shows equivalent neutrophil accumulation in both treatment groups (FIG. 10D), indicating that as in KO1 and KO2, exogenous β-catenin suppression alters the inflammatory response after DDC.

Figure 10E:
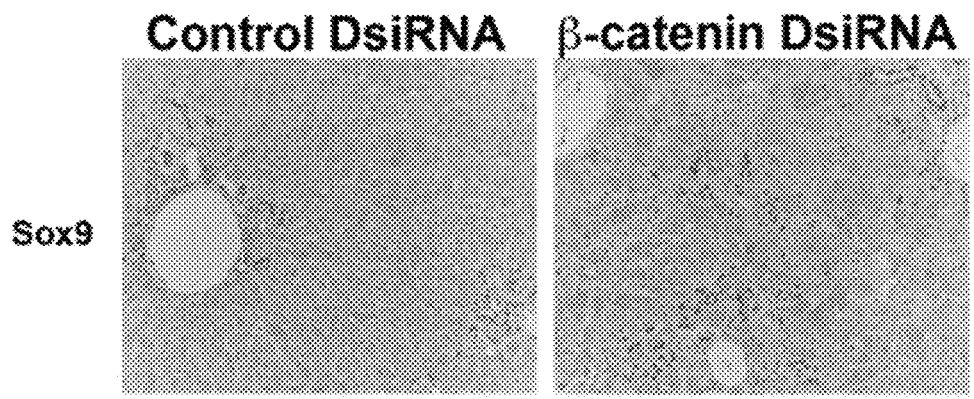
Figure 11A:
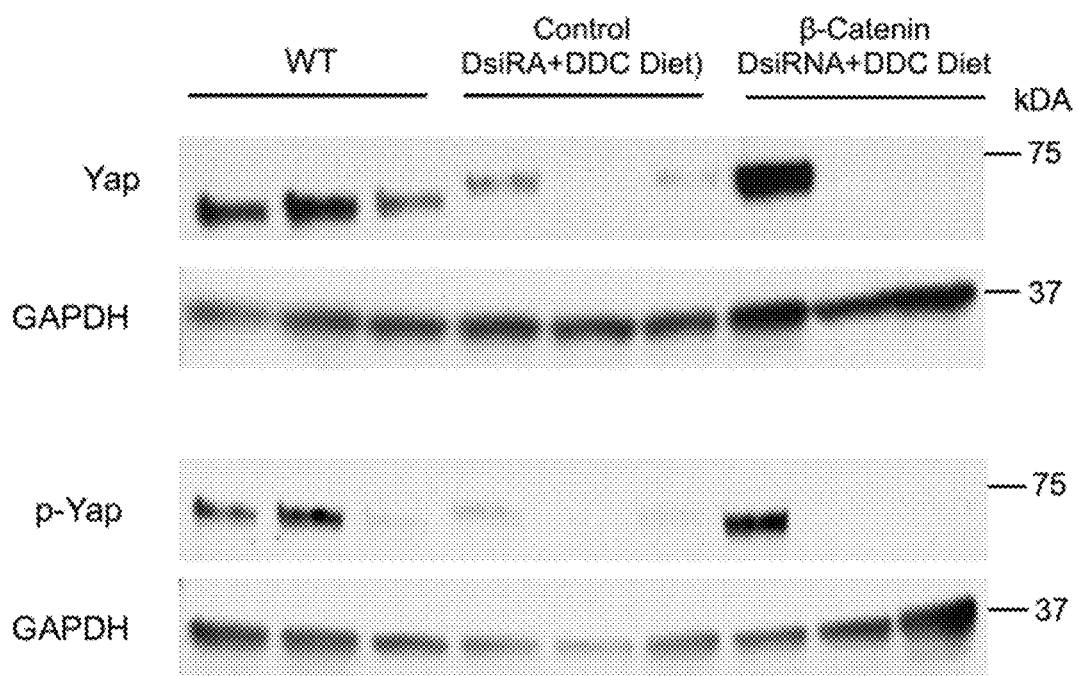
FIGS. 11A-11B: No change in biliary/cholangiocyte markers after β-catenin inhibition and DDC.
Figure 11B:
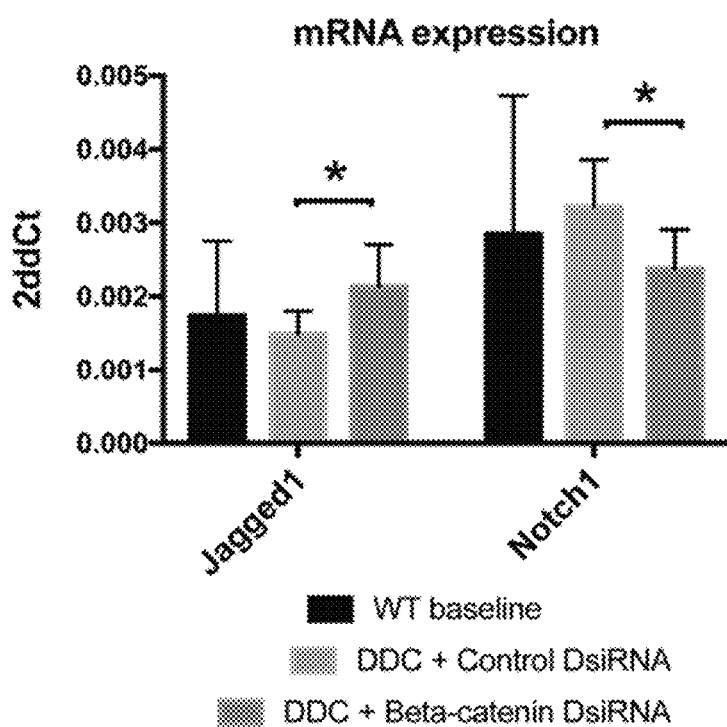

Interestingly, the ductular response in the β-catenin DsiRNA-treated livers extended from the periportal region into the parenchyma, as shown by Sox9 staining (FIG. 10E). Despite the expansion of these atypical ductules, we did not detect an increase in either Notch or Yap signaling in the absence of β-catenin (FIG. 11A; FIG. 11B), indicating that loss of β-catenin does not alter the ductular response.

Figure 12A:
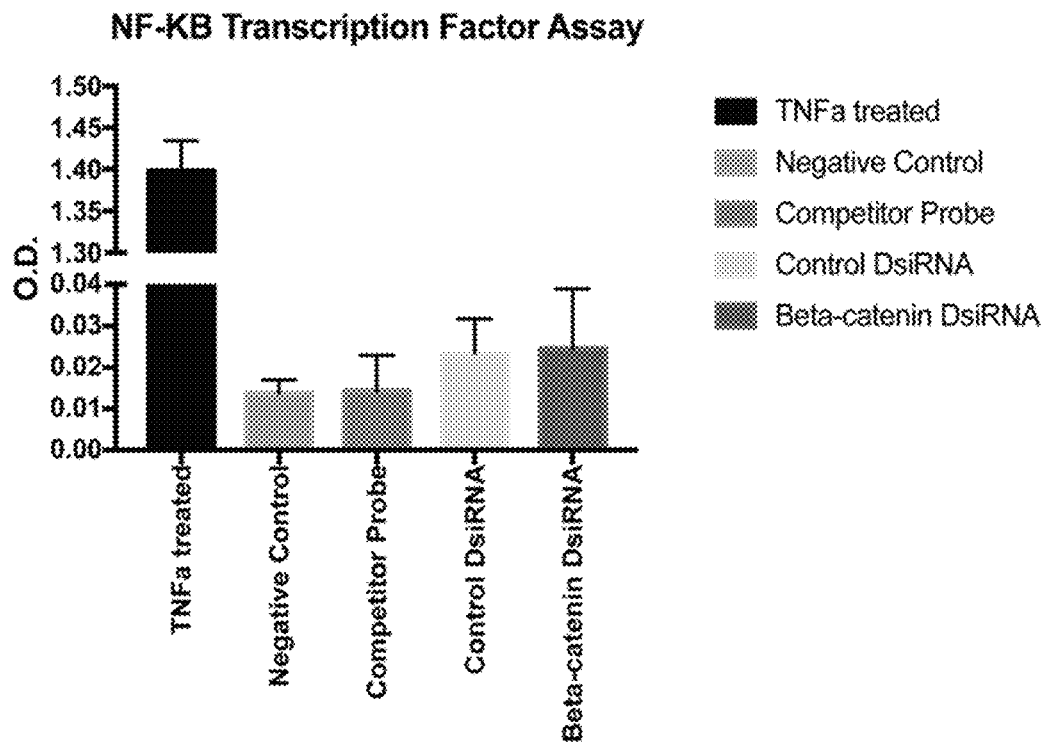
FIGS. 12A-12B: Protection from DDC in β-catenin DsiRNA treated livers is not due to NF-κB activation or decreased bile acid accumulation.
Figure 12B:
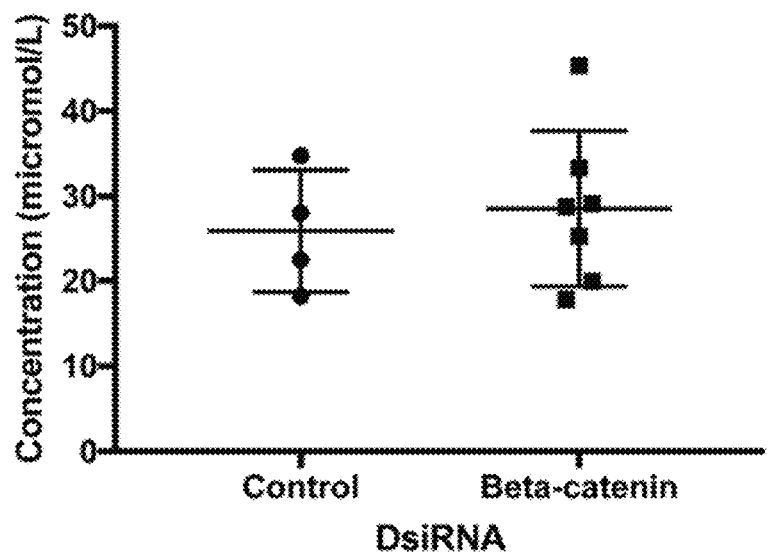
Figure 13A:
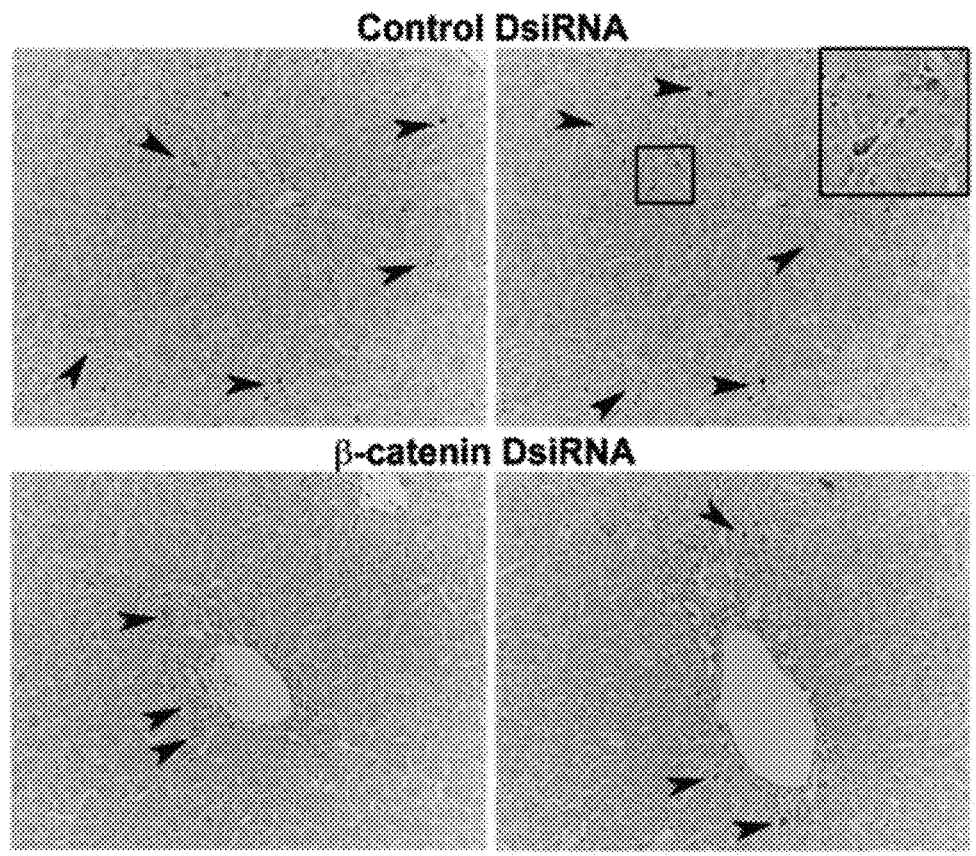
FIGS. 13A-13D: There is decreased porphyrin accumulation in β-catenin DsiRNA treated mice after DDC compared to DDC alone.
Figure 13B:
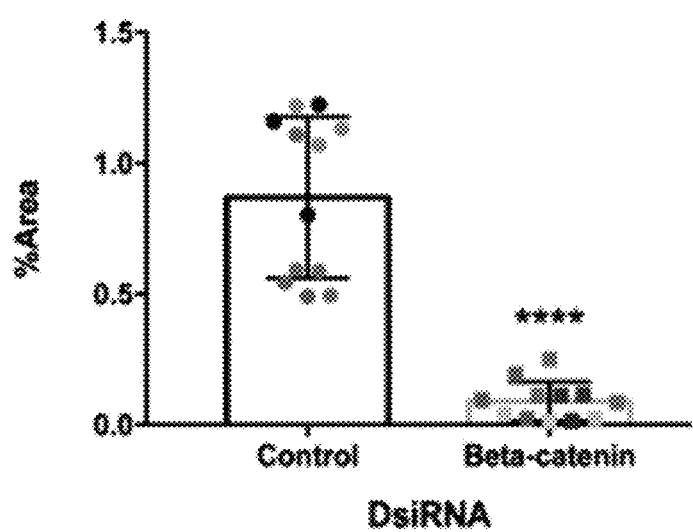
Figure 13C:
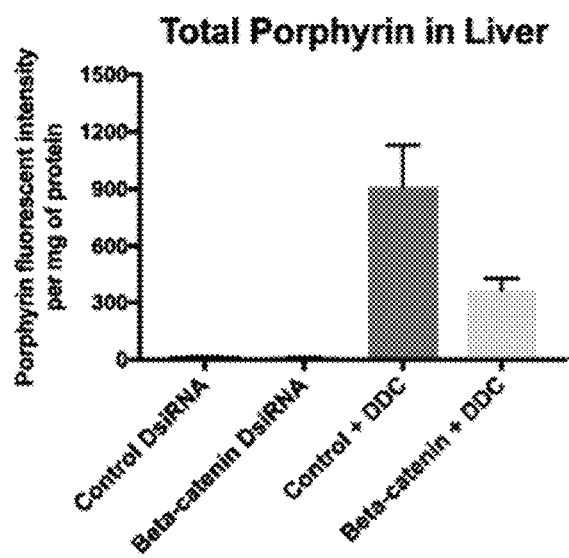
Figure 13D:
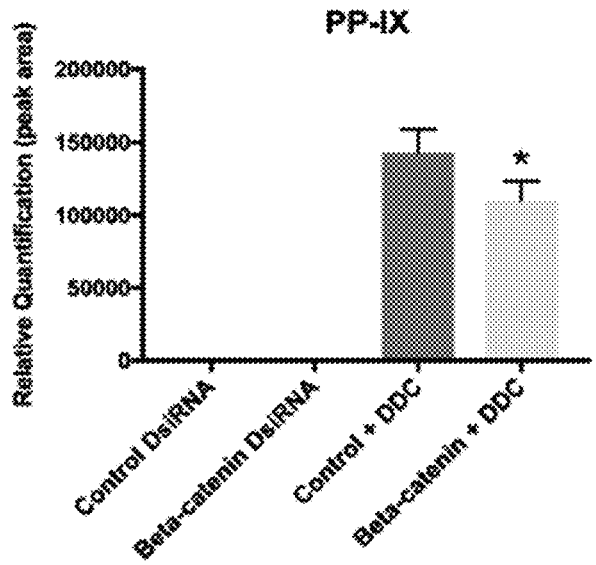

Protection from injury is independent of NF-κB activation or bile acid accumulation. We previously reported that β-catenin KO mice are protected from TNF-α-induced apoptosis and bile acid induced injury through activation of NF-κB and farnesoid X receptor (FXR), respectively (Thompson, M. D., et al. Beta-catenin regulation of farnesoid X receptor signaling and bile acid metabolism during murine cholestasis. *Hepatology* 2018; 67 (3): 955-971 and Nejak-Bowen, K., et al. Beta-catenin-NF-kappaB interactions in murine hepatocytes: a complex to die for. *Hepatology* 2013;57:763-774); thus, we wanted to determine whether either of these mechanisms were playing a role in protection from DDC-induced injury in the absence of β-catenin. Transcription factor assay showed a mild increase in NF-κB DNA binding activity after DDC, which was not further increased with β-catenin DsiRNA (FIG. 12A). We have also previously shown that 4 weeks of DDC induces only a modest increase in bile acids in WT1 mice which was insignificantly decreased in KO1 (Thompson, M. D., et al. Beta-catenin regulation of farnesoid X receptor signaling and bile acid metabolism during murine cholestasis. *Hepatology* 2018; 67 (3): 955-971). However, the amount of total bile acids in the liver was not significantly different between control DsiRNA and β-catenin DsiRNA treatment groups after DDC (FIG. 12B). Therefore, neither increased cytoprotection nor decreased bile acid-induced injury explains the protection from injury seen after DDC in the β-catenin DsiRNA-treated group.

β-catenin DsiRNA treatment reduces the amount of protoporphyrin in livers after DDC compared to control DDC. One of the remarkable features of livers treated with β-catenin DsiRNA and DDC was a decrease in porphyrin accumulation, which gives the DDC-treated livers their characteristic dark-brown color. Similar findings were also noted in livers of KO1 and KO2 mice on DDC (FIG. 4F; FIG. 13F). Whereas in control DsiRNA-treated livers porphyrin was evident throughout the parenchyma as well as in the periportal region, in β-catenin DsiRNA treated livers, only a few porphyrin plugs were evident, and these were exclusively located within the bile ductules (FIG. 13A). Quantification of porphyrin accumulation by channel splitting of brightfield images confirms this decrease (FIG. 13B). Furthermore, when total liver homogenates were assayed for porphyrin and the porphyrin fluorescence normalized to total protein, a 3-fold reduction in total porphyrin was evident in mice treated with β-catenin DsiRNA and DDC compared to mice treated with control DsiRNA and DDC (FIG. 13C). Using liquid chromatography-mass spectrometry (LC-MS) as an additional modality of measuring porphyrin content, we observed that PP-IX levels are significantly less in livers of β-catenin DsiRNA treated mice after DDC (FIG. 13D). Thus, inhibition of β-catenin prevents porphyrin accumulation after DDC.

Figure 14A:
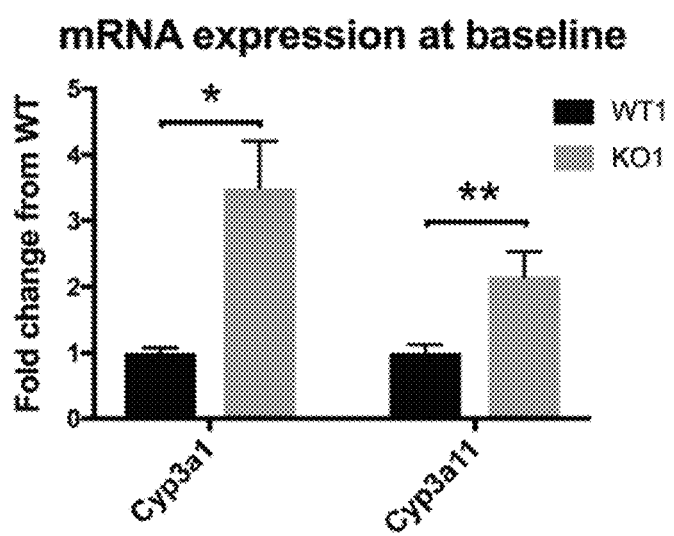
FIGS. 14A-14D: β-catenin inhibition alters pathways involved in DDC metabolism.
Figure 14B:
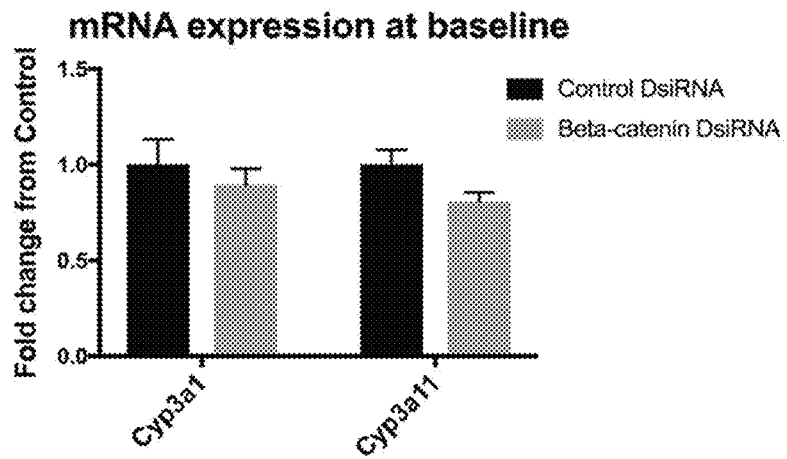
Figure 14C:
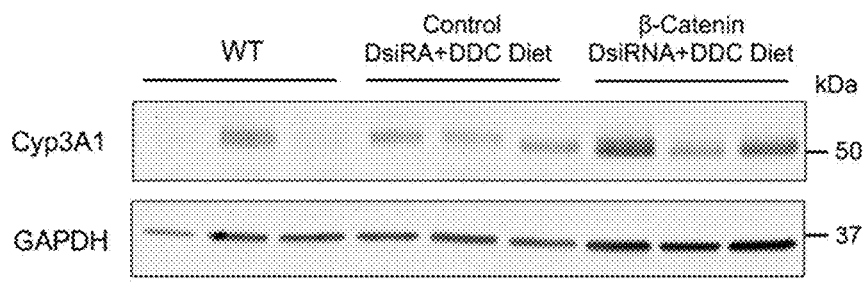

Alterations in expression of cytochrome P450 enzymes and CAR in the absence of β-catenin do not contribute significantly to protection from DDC. To determine if detoxification plays a role in decreasing hepatic injury after DDC in mice lacking β-catenin, we examined mRNA levels of two Cyp3a isoforms, Cyp3a1 and Cyp3a11, at baseline and found a significant increase in both in KO1 livers compared to WT1 (FIG. 14A). However, levels of these Cyp3a isoforms are unchanged in mice treated with β-catenin DsiRNA at baseline before DDC (FIG. 14B), suggesting that the upregulation seen in KO1 may be a compensatory response. Although β-catenin DsiRNA livers showed a modest increase in Cyp3a protein expression compared to control DsiRNA in the presence of DDC (FIG. 14C), it is unclear if this indicative of increased enzymatic activity or rather due to lack of Cyp degradation in these mice.

Figure 14D:
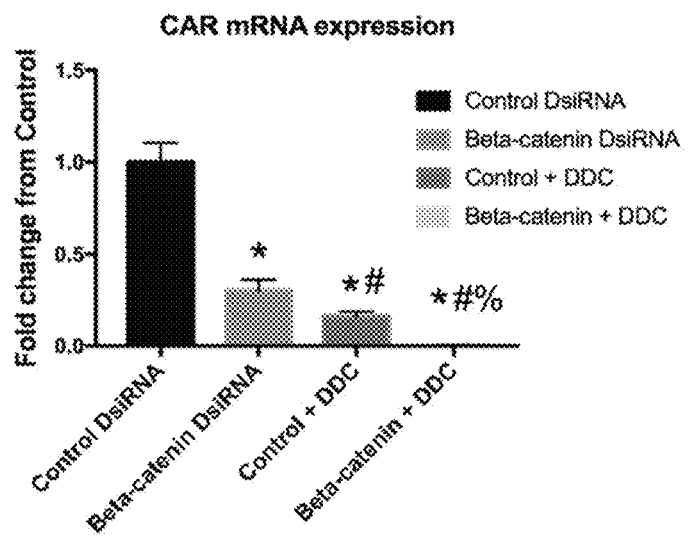

DDC also activates the constitutive androstane receptor (CAR), which contributes to hepatic injury. β-catenin regulates CAR expression, and deletion of β-catenin in KO1 mice results in loss of CAR at both the mRNA and protein level. Similarly, knockdown of β-catenin with DsiRNA significantly decreases CAR expression at baseline (FIG. 14D). Interestingly, CAR expression is suppressed in controls as a response to DDC, while DDC further decreases CAR in β-catenin DsiRNA treated mice.

To rule out if increased Cyp3a and decreased CAR expression after DDC in mice lacking hepatocyte β-catenin is interfering with DDC metabolism and hence is model-specific, we performed an activity assay on ferrochelatase (FC) isolated from DDC-fed mice after control DsiRNA and β-catenin DsiRNA treatment. Notably, there was no measurable activity of FC in either group after DDC treatment (not shown), despite positive controls demonstrating the validity of the assay and confirming the negative results. Thus, despite alterations in pathways that regulate DDC metabolism, these are not the primary mechanism by which these mice evade profound injury, as β-catenin-inhibited mice are responsive to DDC toxicity as seen by complete inhibition of FC.

Figure 15A:
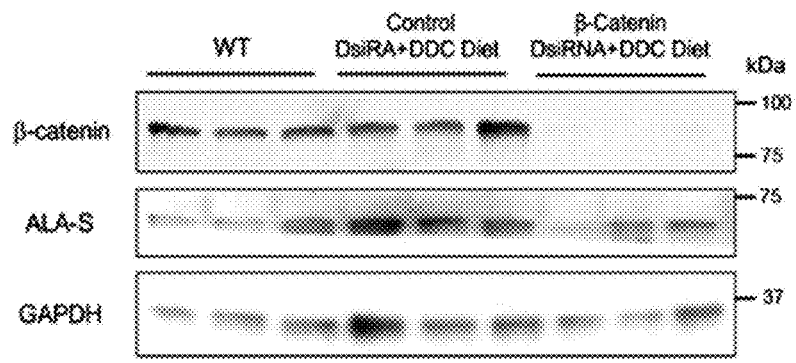
FIGS. 15A-15F: Decreased porphyrin accumulation in β-catenin DsiRNA-treated livers is due to alterations in heme biosynthesis pathway enzymes.
Figure 15B:
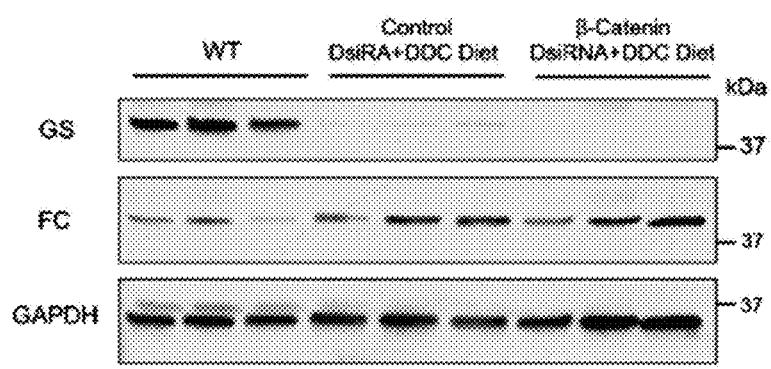
Figure 15C:
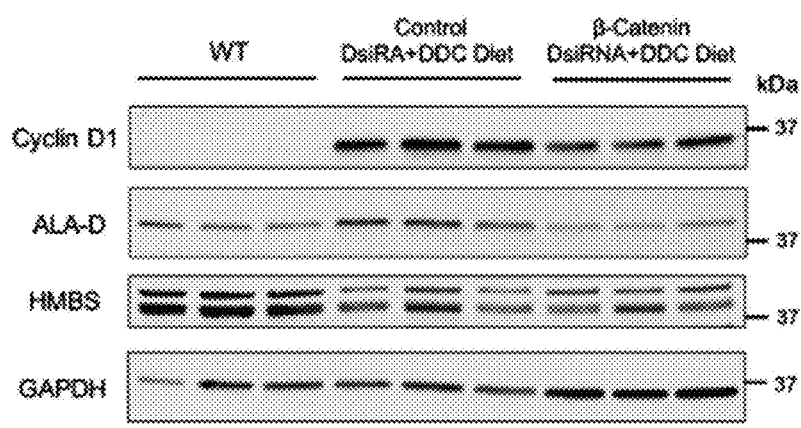

Decreased porphyrin accumulation after β-catenin DsiRNA treatment is a result of decreased expression of enzymes involved in heme biosynthesis. We next determined if upstream inhibition of the heme biosynthesis pathway is responsible for the lack of protoporphyrin accumulation in β-catenin-inhibited animals. We first examined the expression of ALA-S, the rate limiting step in heme biosynthesis, in controls with or without DDC and in β-catenin DsiRNA-treated DDC livers by WB. There was a marked decrease in ALA-S protein in livers treated with β-catenin DsiRNA after DDC, in contrast to livers with control DsiRNA, which had greater ALA-S than WT baseline samples FIG. 15A). Protein levels of FC, which catalyzes the final step in heme biosynthesis, were unchanged after either DDC or administration of either DsiRNA, despite its absent activity (FIG. 15B). We also examined expression of several other enzymes in the heme biosynthesis pathway, specifically δ-aminolevulinic acid dehydratase (ALA-D), which synthesizes porphobilinogen, and HMBS, which catalyzes the synthesis of hydroxymethylbilane. While levels of HMBS were unchanged, ALA-D, like ALA-S, was decreased after-catenin DsiRNA treatment (FIG. 15C).

Figure 15D:
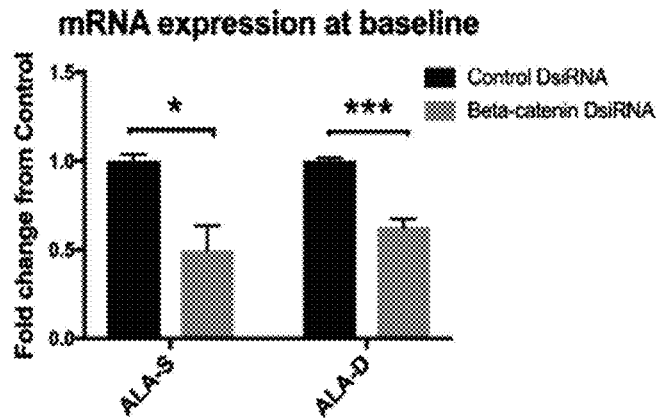
Figure 15E:
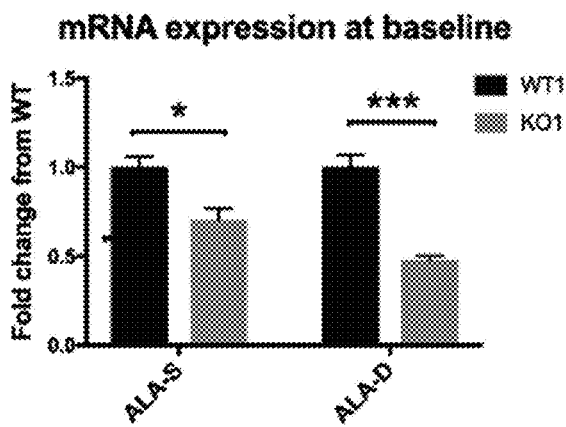
Figure 15F:
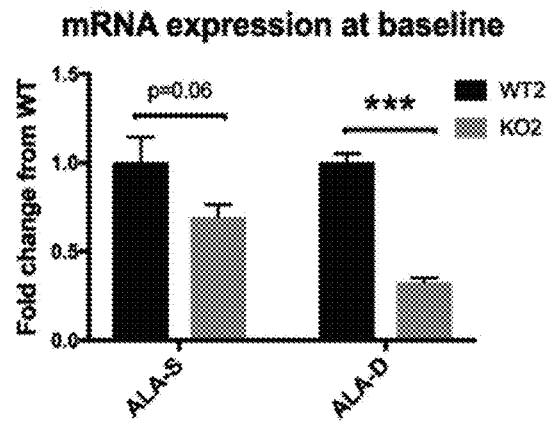
Figure 16:
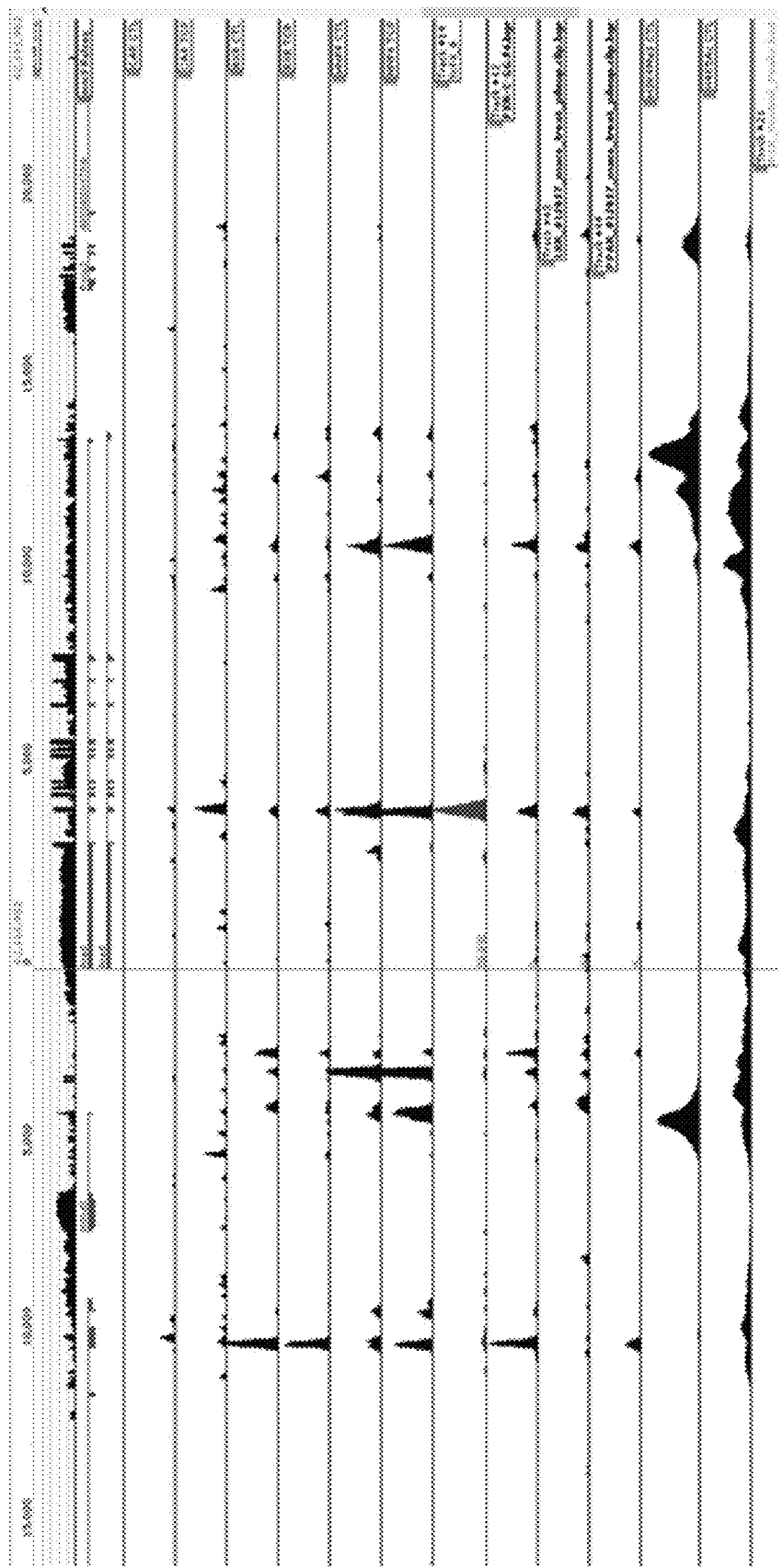
FIG. 16: The ALA-D gene contains a TCF4 binding site. ChIP-seq map across a 50,000 bp region of the ALA-D gene showing binding sites for RXRα, FXR, TCF4, HNF4, as well as H4K5Ac (transcriptionally active chromatin) and H3K4Me3 (active promoter regions) relative to the transcription start site. TCF4 (red peak) binds to an intron downstream of the ALA-D promoter. This binding peak coincides with strong peaks for other nuclear receptors such as CAR, RXRα, FXR, and HNF4.

To determine whether these enzymes were transcriptionally regulated by β-catenin, we analyzed mRNA expression from livers treated with control or β-catenin DsiRNA in the absence of DDC. Notably, both ALA-S and ALA-D were significantly suppressed in the presence of β-catenin DsiRNA (FIG. 15D). Similar decreases in the mRNA expression of these enzymes were also noted in both KO1 and KO2 at baseline (FIG. 15E; FIG. 15F). Furthermore, a strong TCF4 binding site was identified in the intron region of the ALA-D gene by ChIP-seq (FIG. 16), which also corresponds to the binding sites for several other nuclear receptors, like FXR and HNF4. These data indicate that ALA-D may be a direct Wnt/β-catenin target, and that suppression of this enzyme inhibits the early steps in the heme biosynthesis pathway, potentially preventing the accumulation of protoporphyrins.

Figure 17A:
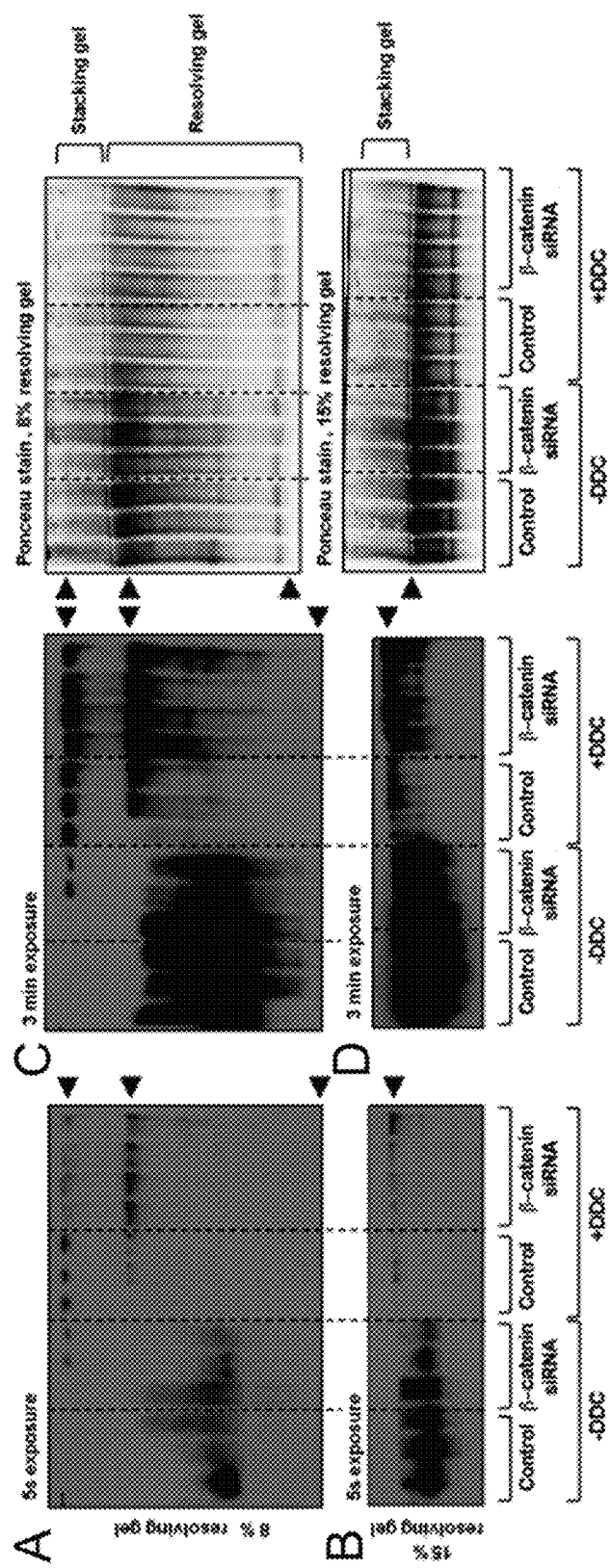
FIGS. 17A-17C: Loss of β-catenin protects mice from DDC-mediated depletion of heme. Total liver homogenates were separated on non-reducing non-denaturing PAGE (8% resolving gel.
Figure 17B:
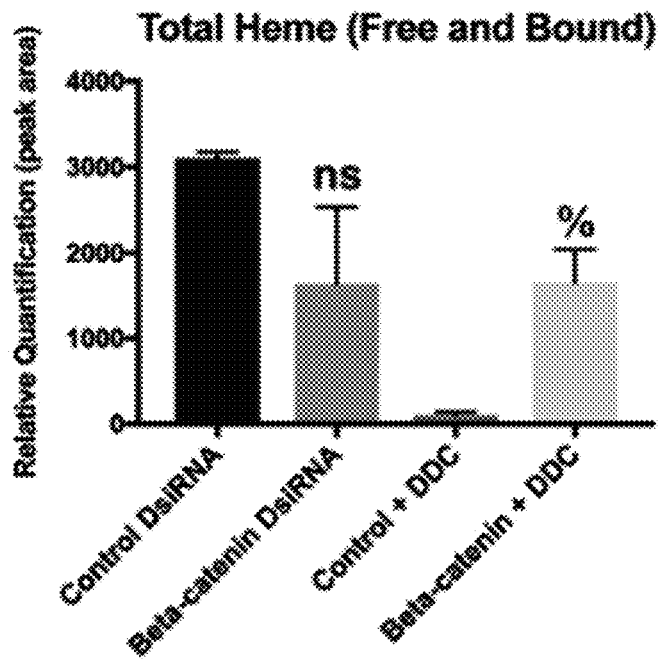
Figure 17C:
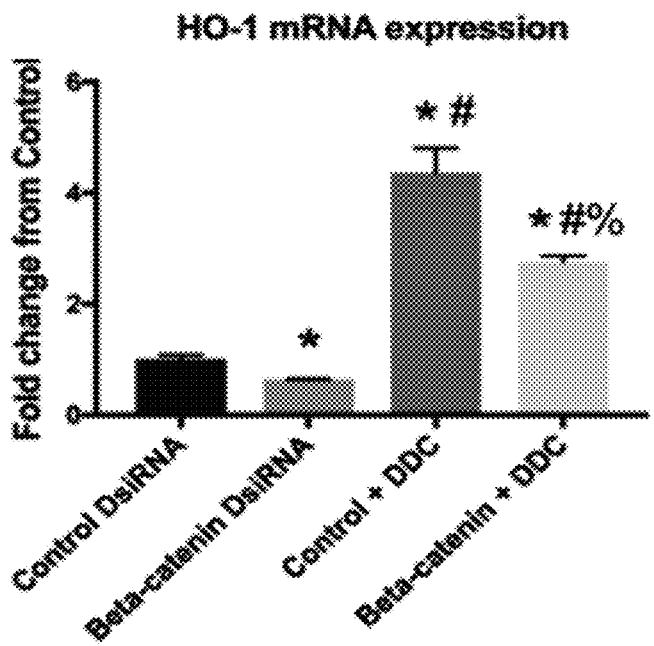

Loss of β-catenin blunts the ability of DDC to deplete heme. One of the major pathways by which DDC mediates its porphyrinogenic effect is through heme depletion, which inhibits the function of hemoproteins such as Cyps that can metabolize and detoxify DDC. Because β-catenin DsiRNA treated livers had less porphyrin accumulation after DDC feeding, we determined whether loss of protein bound heme after DDC feeding is decreased in-catenin inhibited mice compared to mice on DDC alone. We assayed for heme content in hepatic heme-containing proteins and found DDC feeding caused massive heme depletion (FIG. 17A (panel A); FIG. 17A (panel B)). However, upon longer exposure of the film, there is residual protein-bound heme apparent in β-catenin DsiRNA treated livers after DDC feeding compared to controls on DDC (FIG. 17A (panel C); FIG. 17A (panel D)), indicating lesser DDC-mediated heme destruction. A similar trend was observed in denaturing PAGE (FIG. 18 (panels A, B, C, and D). We also measured heme levels in the livers by LC-MS and found preservation of total heme (free and protein-bound) in β-catenin inhibited livers after DDC (FIG. 17B). The increased heme content in the livers of β-catenin DsiRNA treated mice relative to control DDC mice could also be a function of decreased heme degradation, which is catalyzed by heme oxygenase (HO1). We found HO-1 expression was significantly repressed in β-catenin DsiRNA treated livers, both before and after DDC (FIG. 17C). Thus, heme depletion as a consequence of DDC is blunted in the absence of β-catenin through multiple mechanisms.

Figure 18:
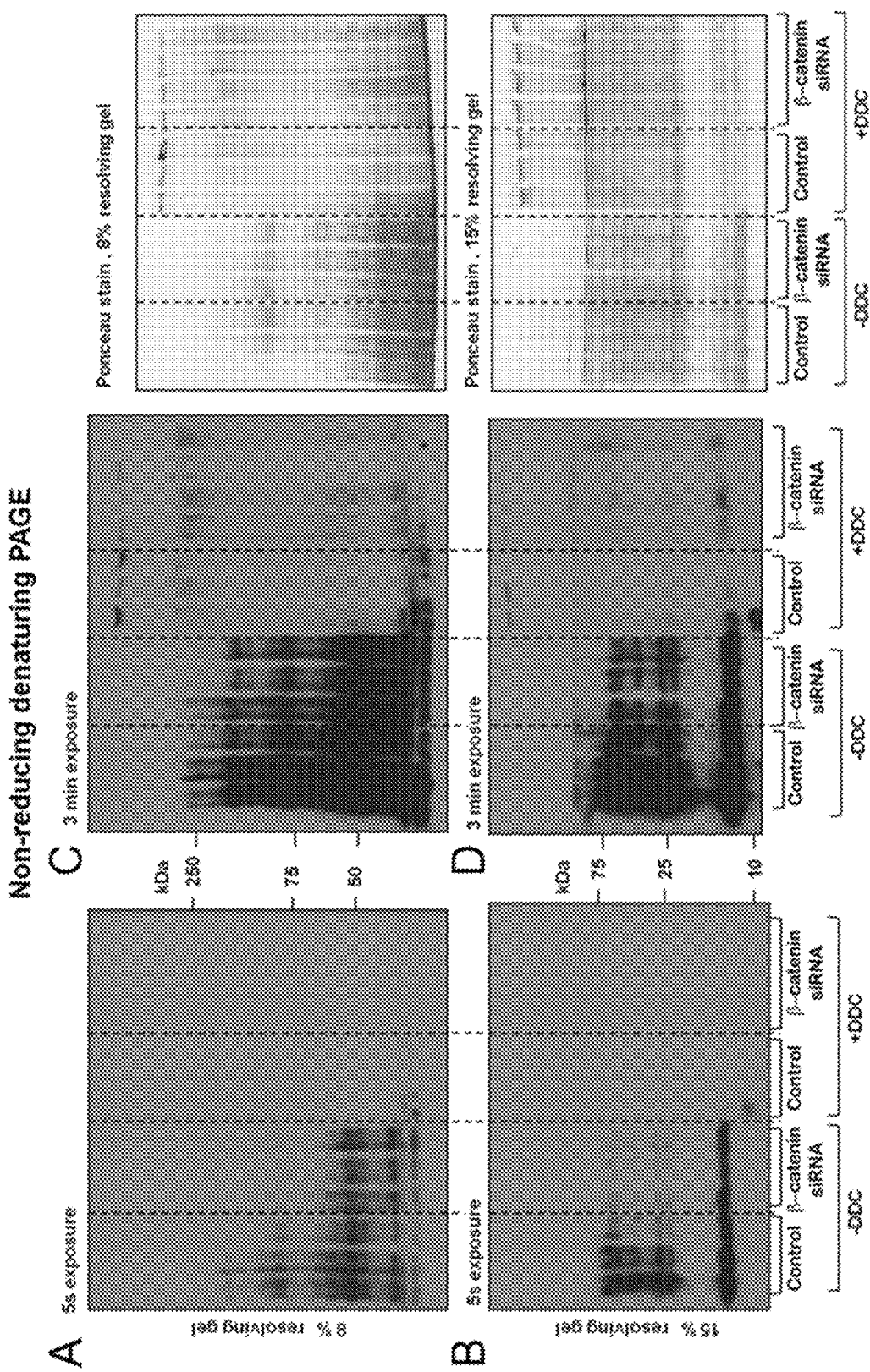
FIG. 18: Loss of β-catenin protects from DDC-mediated destruction of heme-containing proteins.
Figure 19:
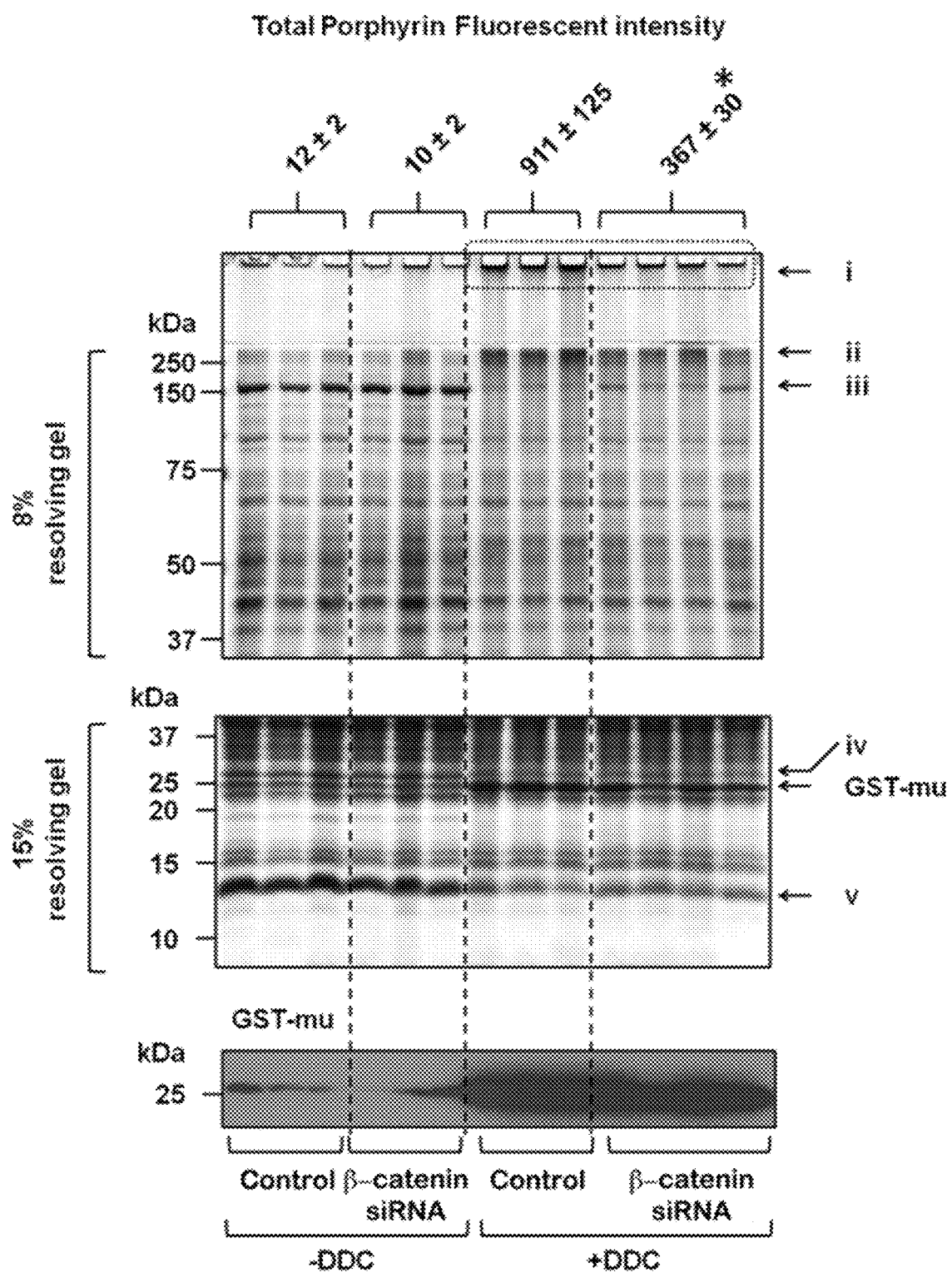
FIG. 19: β-catenin DsiRNA decreases total porphyrin and alters protein aggregation after DDC. (Top two panels) SDS-PAGE stained with Coomassie Blue highlights changes in protein banding pattern (Arrows with roman numerals i-v) as a function of DDC in control vs. β-catenin DsiRNA-treated livers. Porphyrin fluorescence normalized to mg of protein (top of gel) shows a significant decrease in porphyrin accumulation after β-catenin DsiRNA treatment and DDC compared to control DsiRNA after DDC. (Bottom panel) DDC feeding also led to marked induction of GST-mu, visible by Coomassie staining and also validated by immunoblotting. *P<0.05 by Student's t test.
Figure 20A:
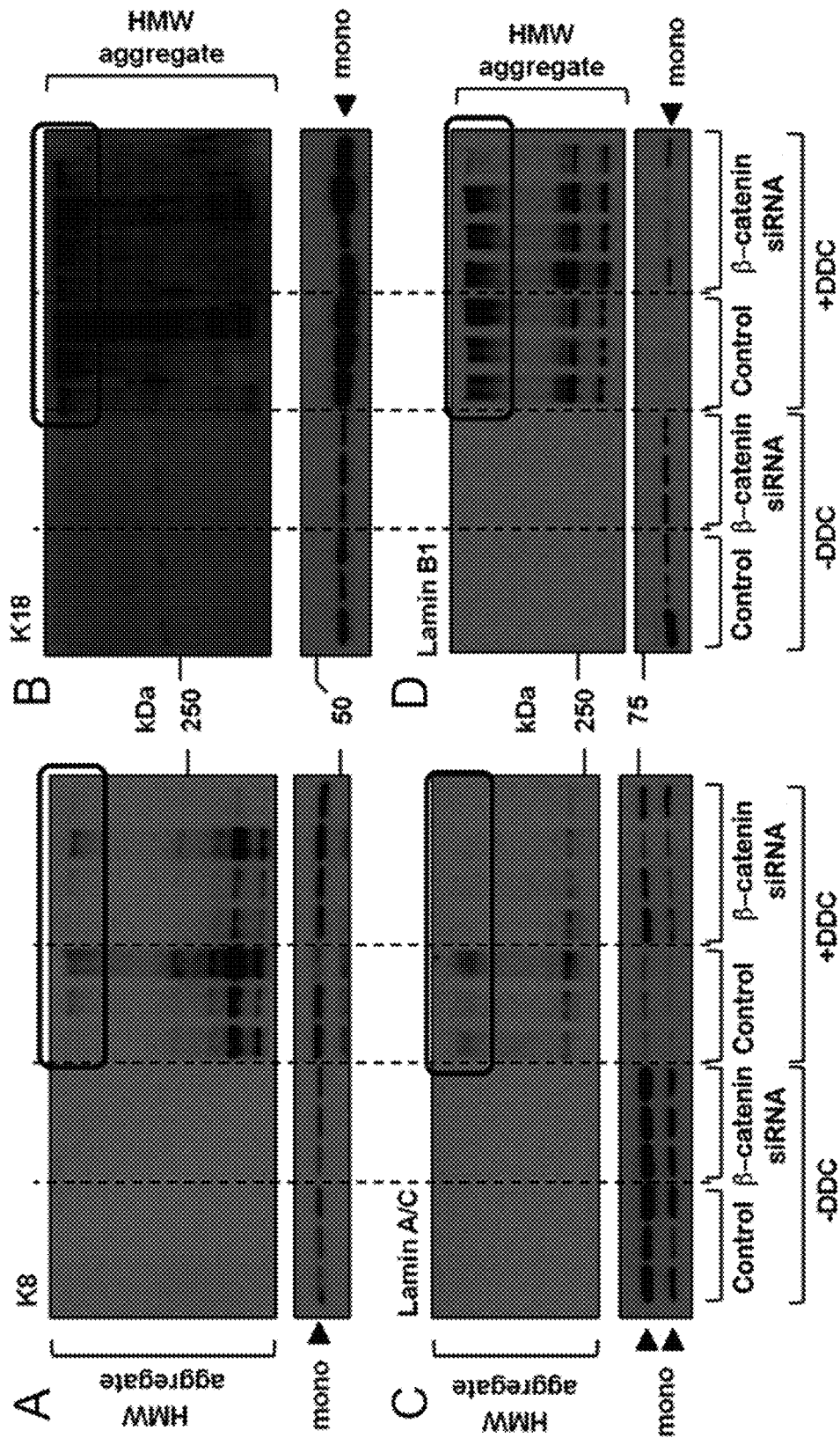
FIGS. 20A-20C: β-catenin inhibition prevents DDC-mediated nuclear IF protein damage.
Figure 20B:
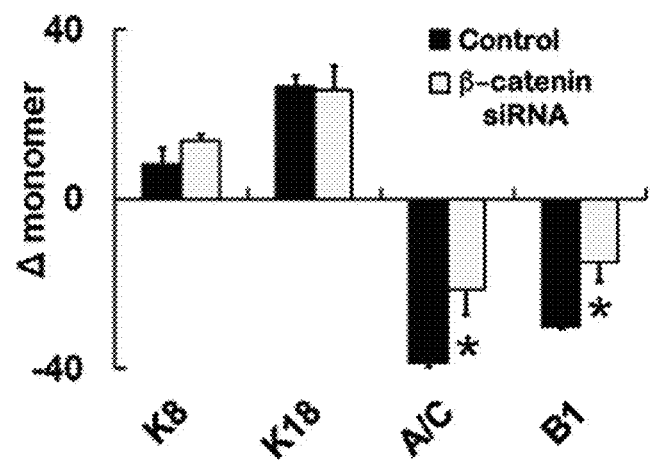
Figure 20C:
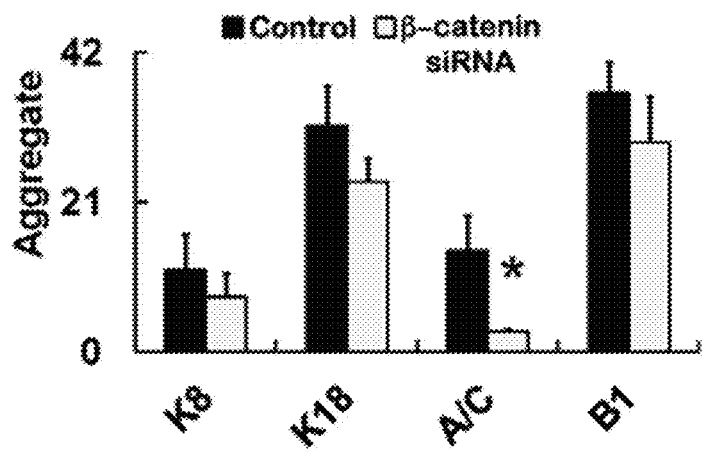

Loss of β-catenin decreased protein aggregation after DDC. We next analyzed the extent of protein aggregation after DDC. SDS-PAGE and Coomassie blue staining shows changes in the protein banding pattern as a function of DDC (FIG. 19). Firstly, there is a loss of discrete banding patterns after porphyrin accumulation (compare bands in position iii, iv, v in DDC fed vs. normal diet fed mice). Secondly, there is an accumulation of high molecular weight (HMW) aggregates (see i and ii and loss of band intensity at position iii) after DDC. Relative to control DsiRNA, treatment with β-catenin DsiRNA led to lower HMW aggregates and increased residual monomer at position iii, which mirrors the difference in the porphyrin levels in these samples. However, induction of glutathione-S-transferase-mu-1 (GST mu), which is upregulated by oxidative stress, was unchanged between control and β-catenin DsiRNA after DDC, as assessed by Coomassie staining and also validated by immunoblotting (FIG. 19; FIG. 18 (panel B)) (Hanada, S., et al. Gender dimorphic formation of mouse Mallory body formation in drug-primed mouse liver. *Am. J. Pathol.* 2002; 161:2019-2026). Thus, while DDC induces protein aggregation, the absence of β-catenin significantly alters the aggregation pattern and reduces total protein aggregates.

β-catenin loss mitigates DDC-mediated nuclear intermediate filament (IF) protein damage. Cytosolic (K8/K18) and nuclear (Lamin A/C, Lamin B1) IF proteins have been reported to be highly susceptible to porphyrin-mediated aggregation. Since inhibition of β-catenin after DDC resulted in decreased porphyrin accumulation, we determined if IF protein aggregation is lower in the absence of β-catenin. DDC feeding has been reported to cause upregulation of cytosolic IF protein K8/K18. Although DDC caused upregulation of both K8 and K18 in both control and β-catenin DsiRNA-treated mice, there was no statistically significant difference in the amount of aggregate formed between the two groups (FIG. 20A (panel A), FIG. 20A (panel B), upper panel, and FIG. 20C). DDC feeding also causes a dramatic loss of the monomer form of nuclear IF proteins, and a concomitant increase in HMW aggregates. Our results showed that inhibition of β-catenin protected against DDC-mediated loss in monomer forms of both Lamin A/C and Lamin B1 (FIG. 20A (panel C), FIG. 20A (panel D), lower panel, and FIG. 20B). Similarly, there was a significantly higher amount of HMW Lamin A/C aggregate in DDC fed control mice compared to β-catenin-inhibited mice (FIG. 20A (panels C and D), upper panel, and FIG. 20C). Thus, loss of β-catenin does not affect cytosolic IF protein damage, but protects against nuclear IF protein damage.

Figure 21A:
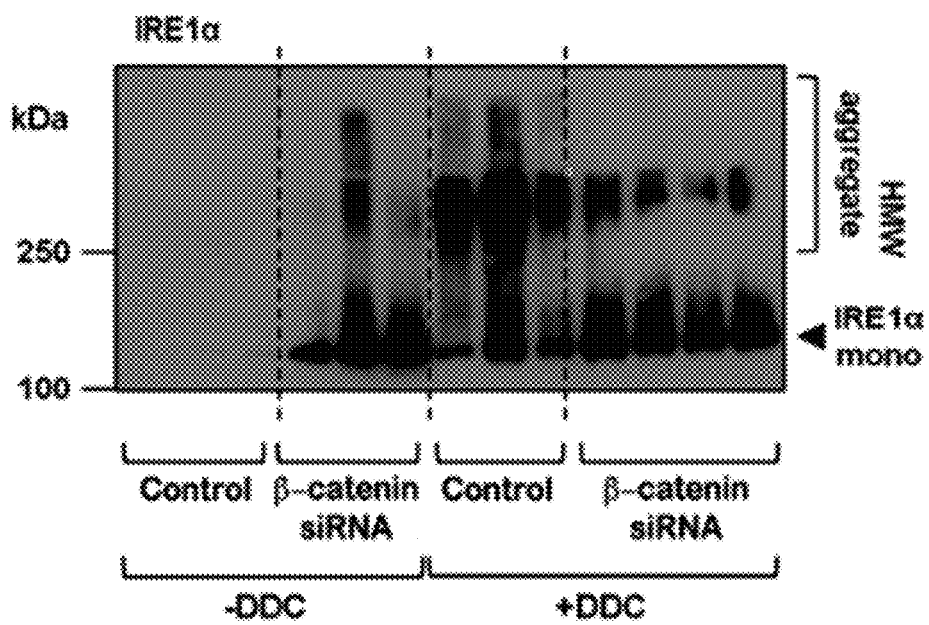
FIGS. 21A-21F: β-catenin ameliorates DDC-associated perturbation of protein clearance and autophagy pathways.
Figure 21B:
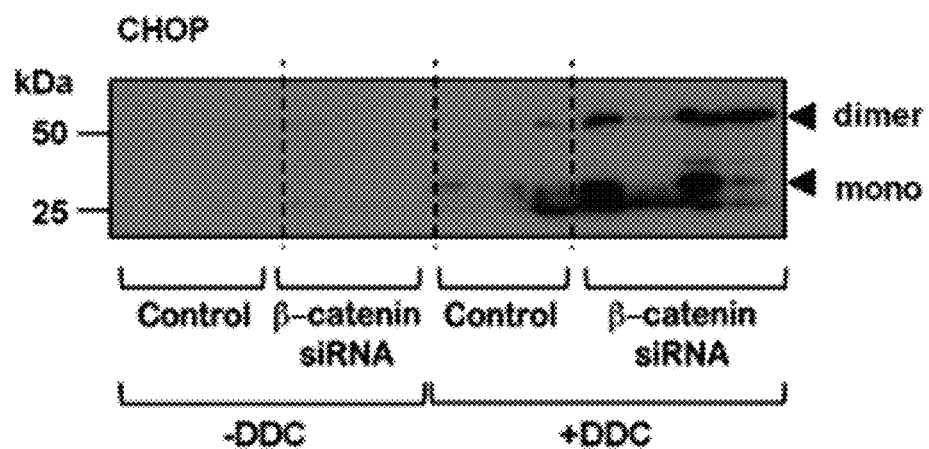

DDC-mediated endoplasmic reticulum (ER) protein damage and autophagy are attenuated by β-catenin DsiRNA. Porphyrins cause ER stress through a non-canonical pathway that involves aggregation of several ER proteins (e.g., BiP, PDI, IRE1α) required for protein quality control. Since IRE1α is essential in activating the unfolded protein response (UPR) during ER stress, we analyzed its protein expression before and after DDC. Under basal conditions, we saw increased IRE1α expression in β-catenin DsiRNA treated livers (FIG. 21A), which may be due to the role of β-catenin in regulating the expression of antioxidant genes. DDC led to an increase in the formation of HMW aggregates; however, the IRE1α monomer was greater in livers of mice treated with β-catenin DsiRNA than in control DDC livers, while the aggregate form was decreased. Mice treated with β-catenin DsiRNA also had markedly higher levels of both the monomer and dimer forms of CCAAT-enhancer-binding protein homologous protein (CHOP), another mediator of ER stress (FIG. 21B). Thus, while DDC increases the aggregation of misfolded ER proteins such as IRE1α, this effect is decreased in the absence of β-catenin, leading to increased functionality of the ER stress response.

Figure 21C:
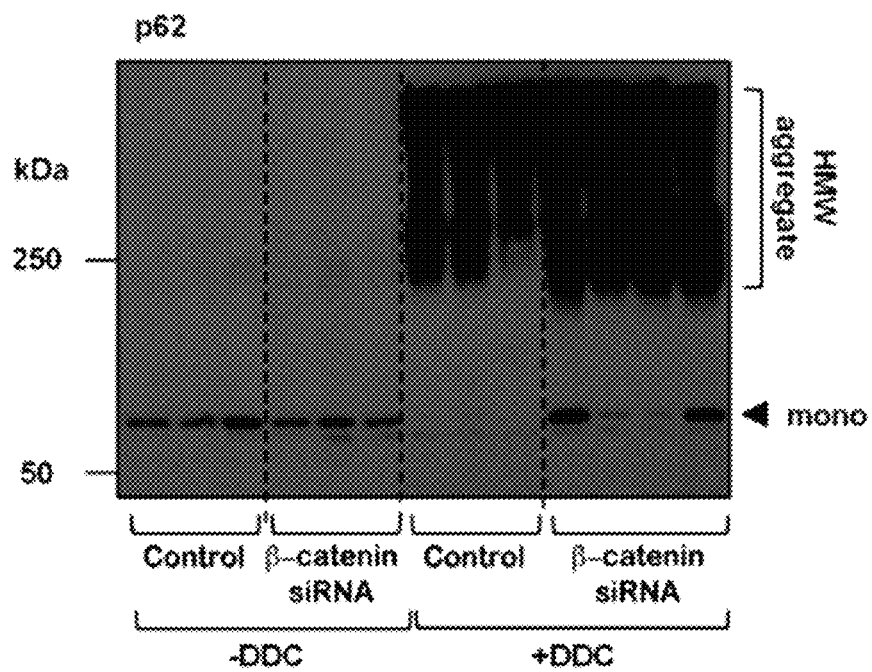
Figure 21D:
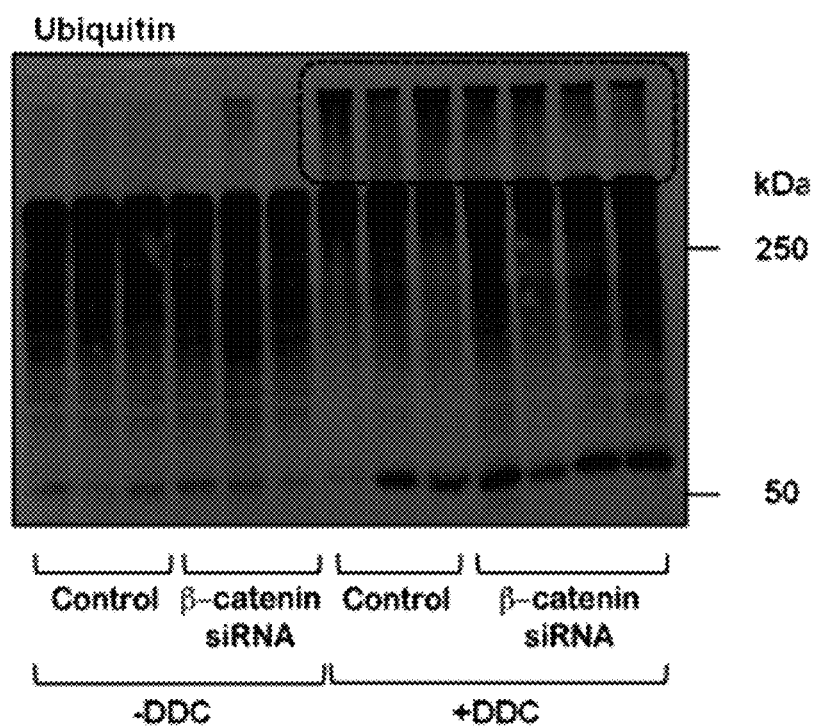

A similar finding was observed with p62, a poly ubiquitin (Ub) binding protein that is upregulated after DDC. p62 increased in both control and β-catenin DsiRNA-treated livers after DDC and was mainly contained in HMW aggregates (FIG. 21C). However, p62 monomers were also present in β-catenin DsiRNA livers, with complete loss of monomer observed in controls after DDC feeding, suggesting preservation of protein functionality. Interestingly, although both control and β-catenin DsiRNA-treated mice show increased poly-ubiquitinated proteins after DDC, the extent of proteasomal inhibition was similar in both groups (FIG. 21D).

Figure 21E:
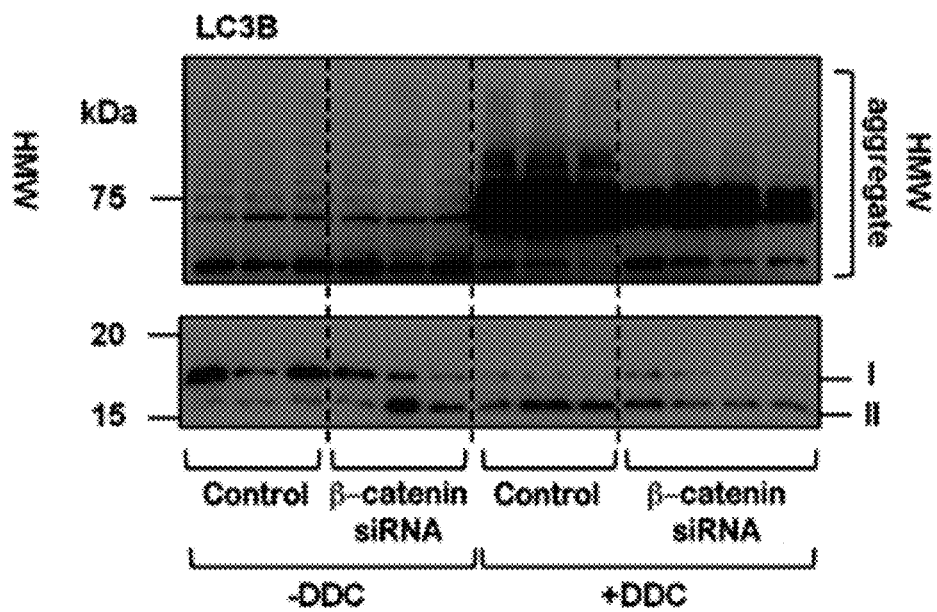
Figure 21F:
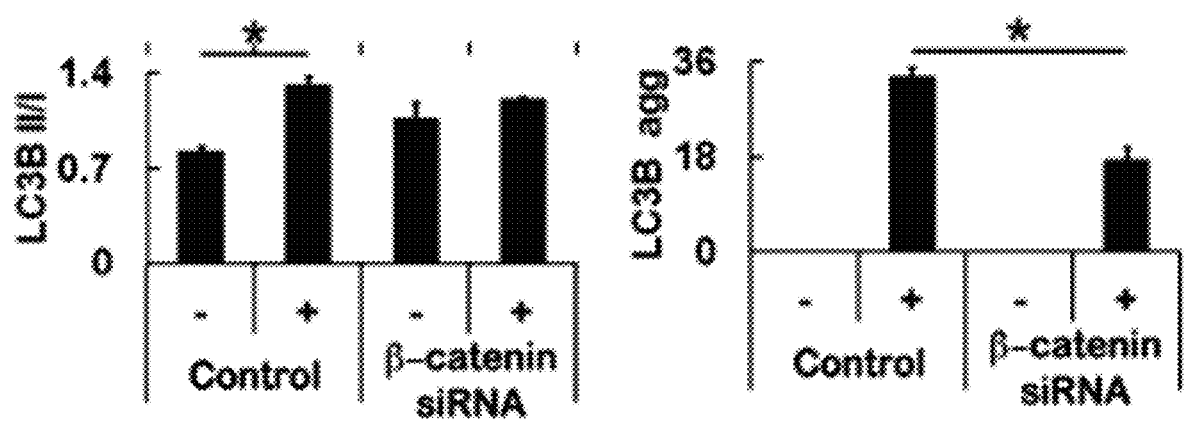

Protein aggregation as a function of porphyrin accumulation also induces an autophagic response in order to clear the misfolded proteins. The increase in the level of LC3B-II compared to LC3B-I in the cell is a measure of autophagy activity in the cell. The LC3B II/I ratio was increased under basal conditions in mice treated with β-catenin DsiRNA compared with controls, albeit insignificantly (FIG. 21E; FIG. 21F). However, after DDC there was no further induction of autophagy over baseline in β-catenin DsiRNA treated mice, whereas control mice showed a significant increase in the LC3B II/I ratio compared to baseline. In a similar trend, control mice showed significantly higher levels of HMW LC3B aggregates than mice lacking β-catenin (FIG. 21E;

FIG. 21F). Thus, DDC-induced autophagy activation is blunted in the presence of β-catenin DsiRNA, likely due to the decrease in HMW protein aggregates compared to controls.

Figure 22A:
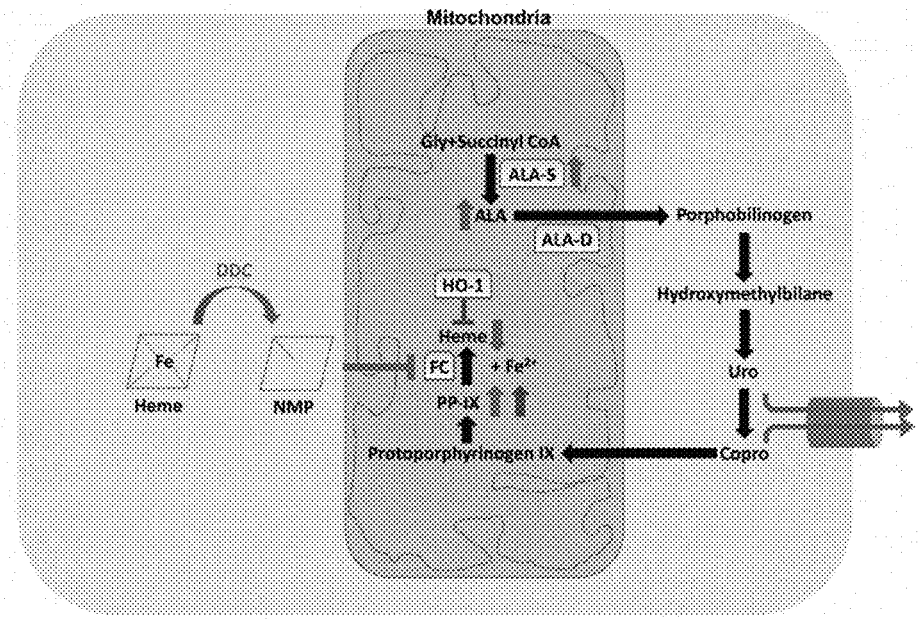
FIGS. 22A-22B: Model showing the interaction of DDC with heme biosynthetic pathway, and its modulation by β-catenin.
Figure 22B:
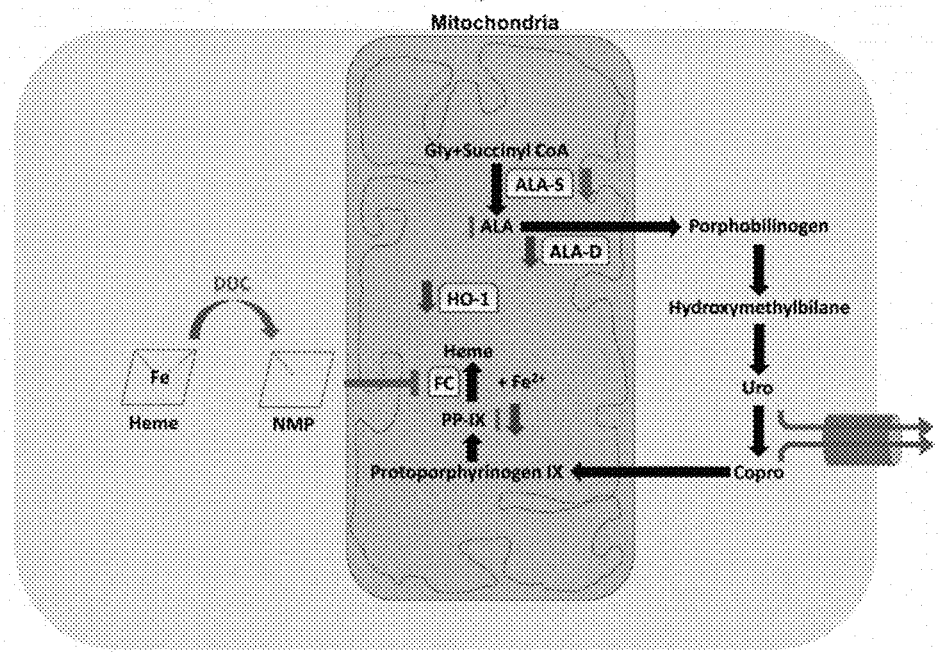

In mouse models, we demonstrate a therapeutic benefit of inhibiting β-catenin in protecting livers from *porphyria*-induced injury. This inhibition affected multiple points in the pathway, including suppression of CAR, ALA-D, and HO-1, and negative feedback regulation of ALA-S (FIG. 22). Although there may be negative effects of long-term β-catenin suppression, such as counteracting oxidative stress (Nejak-Bowen, K. N., et al. Beta-catenin regulates vitamin C biosynthesis and cell survival in murine liver. *J. Biol. Chem.* 2009; 284:28115-28127 and Zhang, X. F., et al. Conditional beta-catenin loss in mice promotes chemical hepatocarcinogenesis: role of oxidative stress and platelet-derived growth factor receptor alpha/phosphoinositide 3-kinase signaling. *Hepatology* 2010; 52:954-965), and therefore sustained β-catenin inhibition may be contra-indicated, treatment cycles with a β-catenin suppressor are believed to be both safe and efficacious at ameliorating liver injury caused by porphyrin disorders.

Example 2

Two-month old CD-1 mice were started on a 0.1% DDC diet to induce *porphyria*. Three days after starting the diet, mice received intraperitoneal (i.p.) injections of 30 mg/kg Porcupine (PORCN) inhibitor Wnt-C59. The Wnt-C59 was delivered on a five days on, two days off schedule for two weeks. Mice were sacrificed 6 hours after the final dose of Wnt-C59. Serum and livers from the control and experimental groups were utilized for IHC, Western blotting, and biochemical assays, as described in Example 1.

Figure 23A:
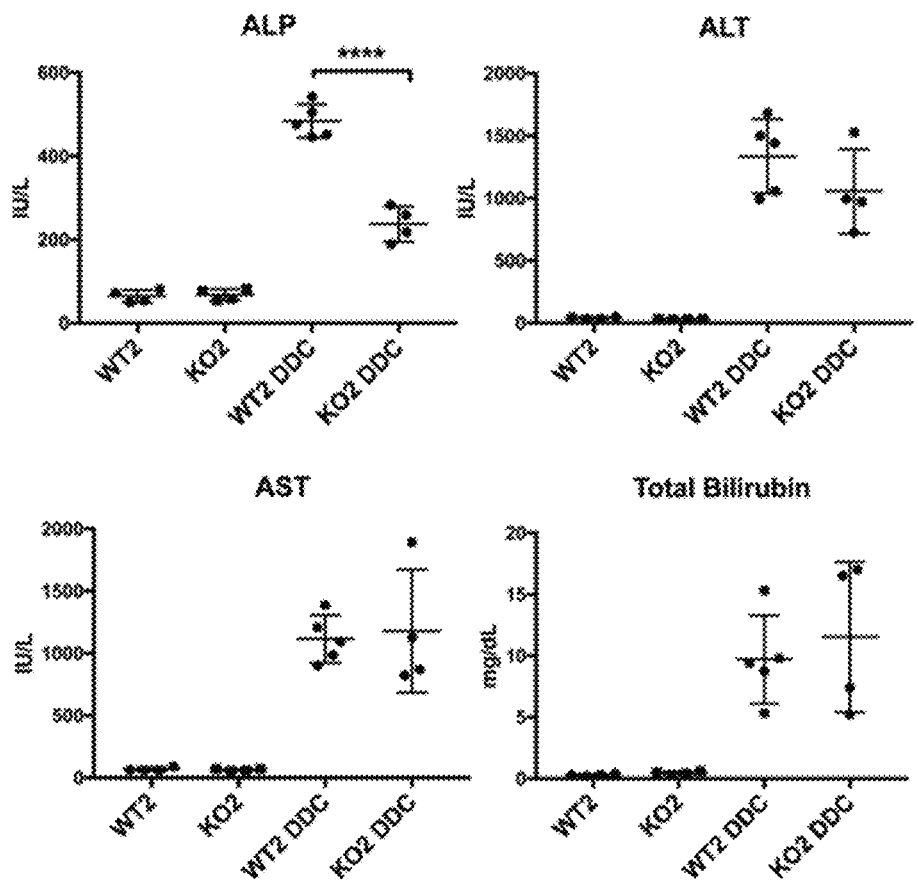
FIGS. 23A-23C: β-Catenin transcriptional inhibitor Wnt-C59 reduces injury after DCC.
Figure 23B:
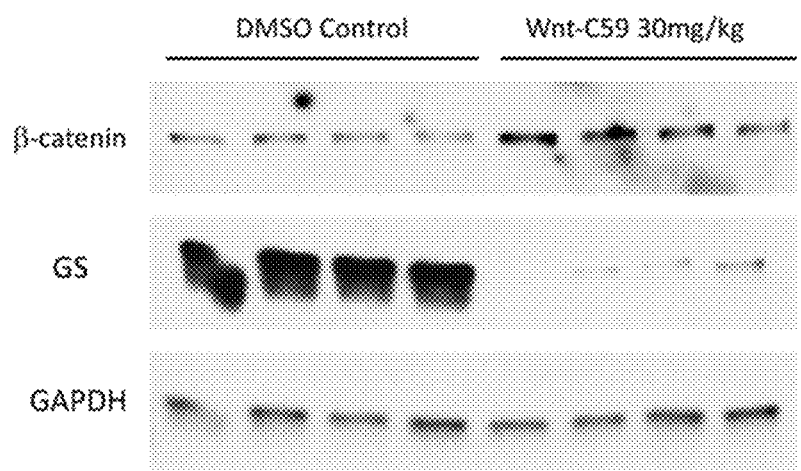
Figure 23C:
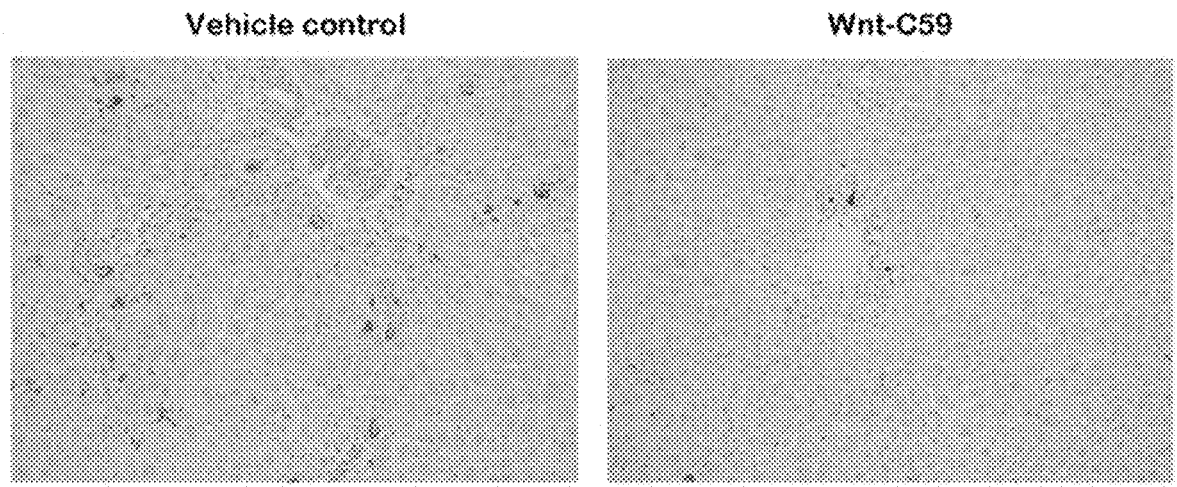

Results show that serum markers of hepatobiliary injury (ALP, ALT, AST, and total bilirubin) are significantly reduced (FIG. 23A). In addition, Wnt-C59 effectively inhibited β-catenin activity, as shown by the decrease in glutamine synthetase (GS) in FIG. 23B and a decreased porphyrin accumulation in the Wnt-C59 experimental group in FIG. 23C. Treatment of mice with Wnt-C59, abolishes Wnt secretion and prevents β-catenin activation, recapitulates the findings in genetic knockout of β-catenin and RNAi-based inhibition of β-catenin.

Example 3

WT1/T2 mice were utilized as these mice show approximately 30% of normal hydroxymethylbilane synthase (HMBS) activity and mimic acute intermittent *porphyria* (AIP) upon administration of phenobarbital, due to the massive accumulation of porphyrin precursors. Two-month old WT1/WT2 mice received i.p. injections of 30 mg/kg Wnt-C59. The same dosing regimen and sacrifice schedule was utilized as in Example 2. Livers from the control and experimental groups were utilized for protein extraction and Western blotting, as described in Example 1.

Figure 24:
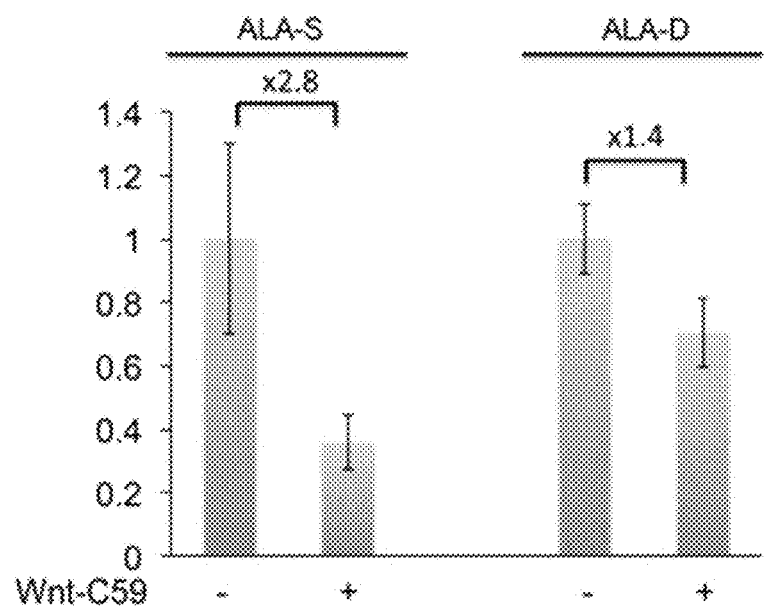
FIG. 24: β-Catenin inhibition reduces basal hepatic ALA-S and ALA-D mRNA levels in WT1/WT2 mice.

Results from Western blot show that mRNA levels of ALA-S and ALA-D (the first two enzymes in the heme biosynthesis pathway) is significantly reduced in Wnt-C59 WT1/WT2 mouse experimental group, as compared to the control group (FIG. 24). These results were also observed with the DDC-treated mice with inhibition of β-catenin.

Example 4

An additional mechanism through which β-catenin suppression may be alleviating *porphyria* is through the β-catenin/GS/mTOR axis to induce autophagy. Autophagy is a potential mechanism for the clearance of aggregated or misfolded proteins caused by porphyrin inclusions.

A group of two-month old WT1/WT2 control mice and mice injected with β-catenin DsiRNA were fed a diet lacking DCC, as described in Example 1. In a second group, control mice and mice injected with β-catenin DsiRNA were fed a diet containing DCC, as described in Example 1. Livers from the controls and β-catenin DsiRNA experimental groups were utilized for protein extraction, SDS-Page, Western blotting, and biochemical assays as described in Example 1.

To test the effect of Wnt-C59 on GS and p-mTOR levels, two-month old WT1/WT2 mice were exposed to a DCC diet, as described in Example 1, and received i.p. injections of Wnt-C59, as described in Example 2. Livers from the control and experimental groups were utilized for IHC, as described in Example 1.

Figure 25A:
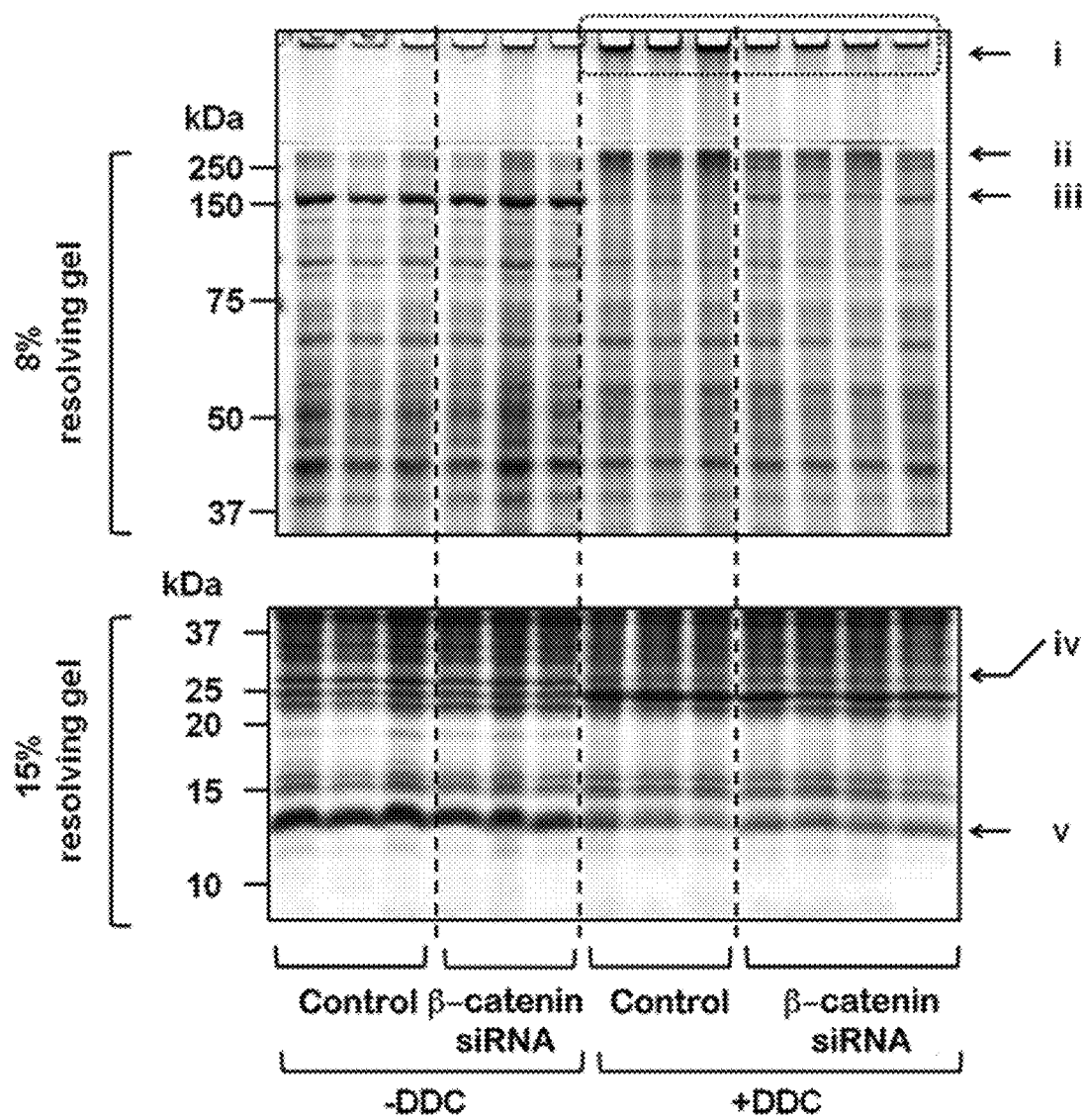
FIGS. 25A-25B: β-Catenin inhibition ameliorates DDC-associated protein aggregation and promotes autophagy.
Figure 25B:
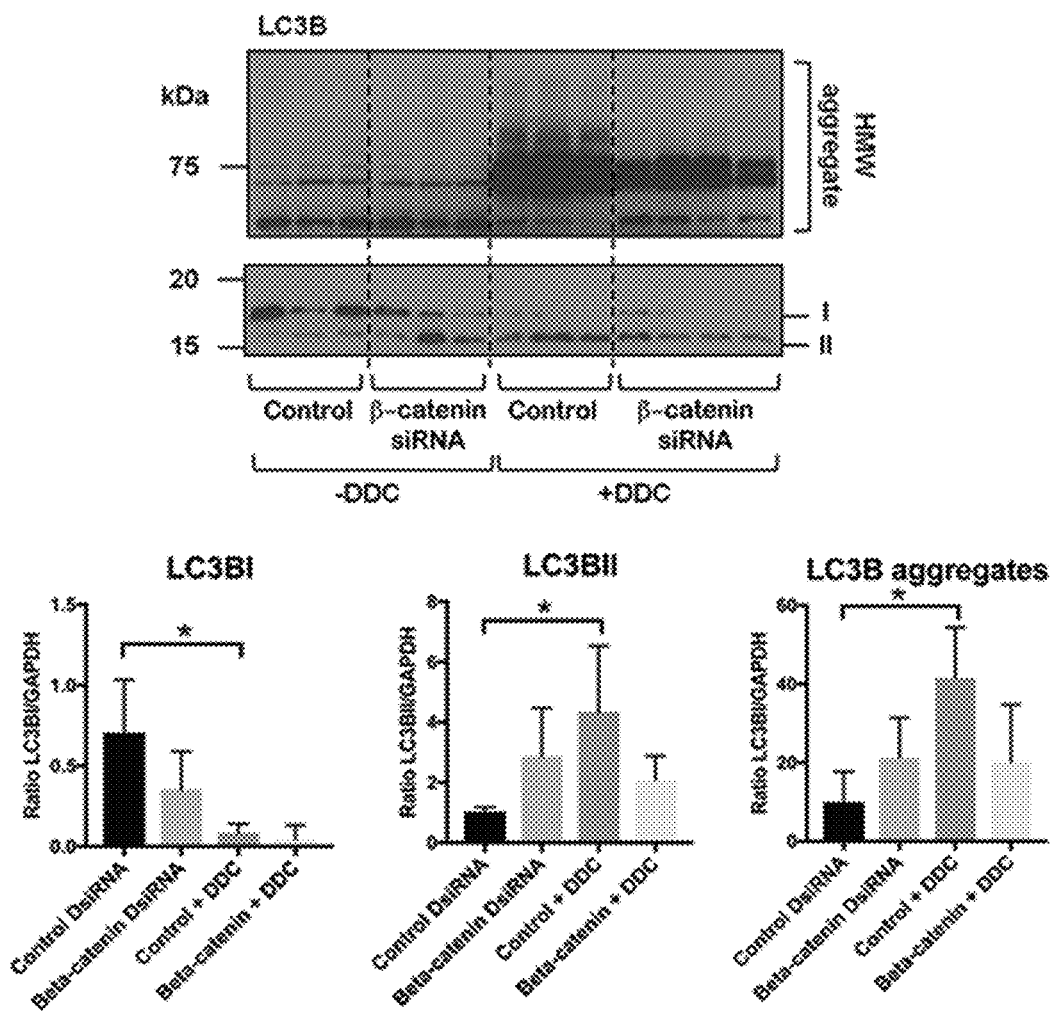

SDS-Page was utilized to highlight the changes in the protein banding pattern between controls and β-catenin DsiRNA experimental groups, as a function of a DCC diet (FIG. 25A). Western blot and assays showed a decrease in LC3BI protein and an increase in LC3BII protein produced after β-catenin DsiRNA treatment (FIG. 25B). Increased levels of LC3BII indicated activated autophagy, as the loss of β-catenin led to the loss of p-mTOR expression. Control mice fed DCC also showed an induction of autophagy, likely a result of increased protein aggregation. The level of LC3B aggregates decreased in mice treated with β-catenin and DCC, as compared to the control.

Figure 26:
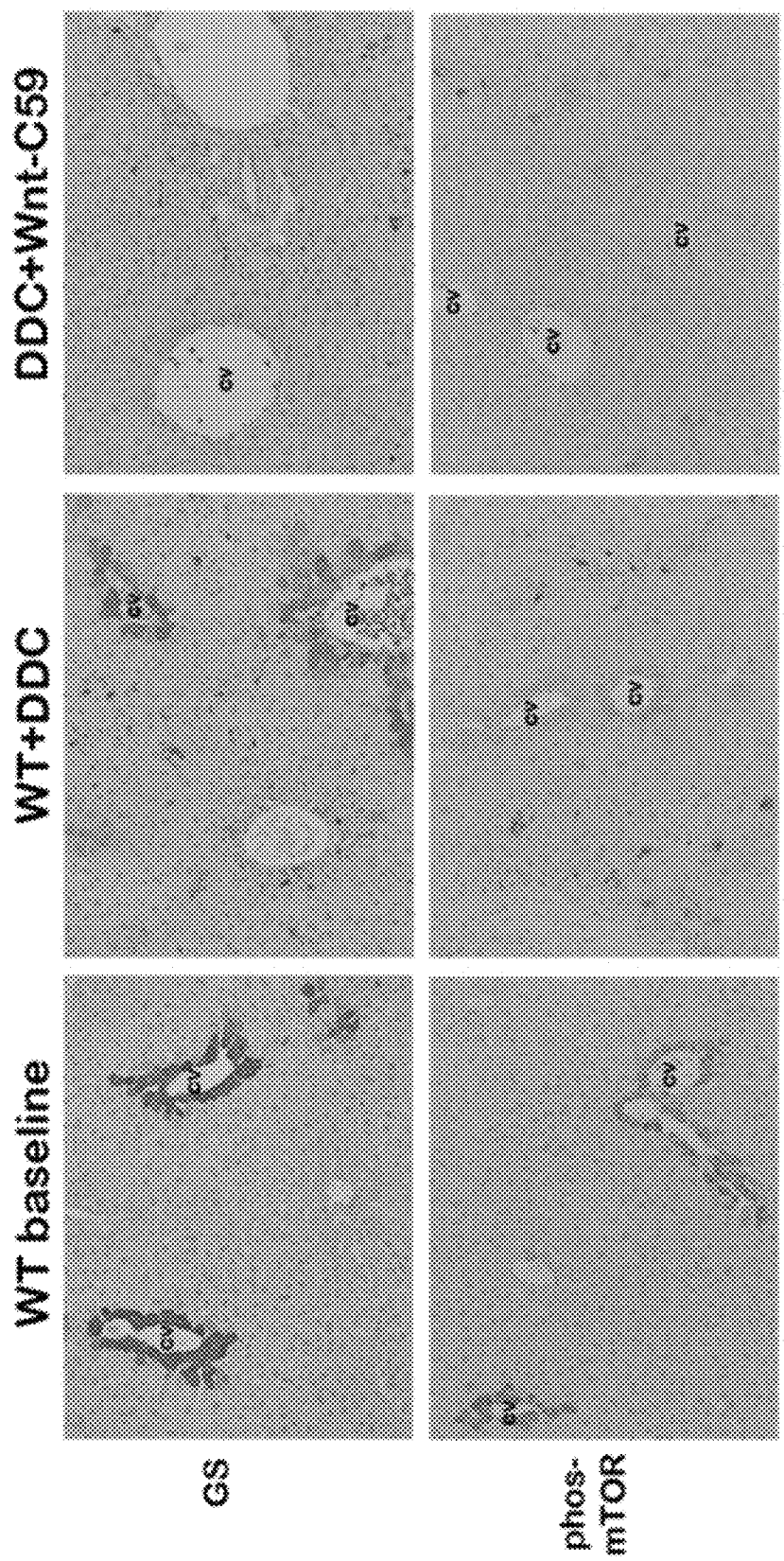
FIG. 26: GS and p-mTOR-S2448 are absent after Wnt-C59 treatment and DDC. IHC shows presence of both GS and p-mTOR around the central vein (cv) in WT at baseline. After DDC, expression of both proteins is decreased; the combination of DDC and Wnt-C59 inhibition, however, leads to complete loss of GS and p-mTOR in zone 3.

IHC of WT1/WT2 mice livers showed that β-catenin is able to regulate phospho-mTOR S2448 (p-mTOR) (FIG. 26). The expression of p-mTOR is through the β-catenin transcriptional regulation of GS, which sequentially regulates the glutamine levels that can phosphorylate mTOR directly. Control WT1/WT2 mice had both GS and p-mTOR proteins around the central vein location. The expression of both GS and p-mTOR proteins decreased with a DCC diet, while a DCC diet and Wnt-C59 injection led to no expression of the GS and p-mTOR proteins.

Although the methods have been described in detail for the purpose of illustration based on what is currently considered to be the most practical and preferred embodiments, it is to be understood that such detail is solely for that purpose and that the methods are not limited to the disclosed embodiments, but on the contrary, is intended to cover modifications and equivalent arrangements that are within the spirit and scope of the appended claims. For example, it is to be understood that the present methods contemplate that, to the extent possible, one or more features of any embodiment can be combined with one or more features of any other embodiment.

The present invention is also directed to the following clauses:

Clause 1: A method of treating *porphyria* in a patient in need thereof, comprising: decreasing expression or activity of β-catenin in the patient, thereby decreasing porphyrin production and/or accumulation, or reducing one or more symptoms of *porphyria*, such as liver injury in the patient by administering to a patient an amount of a therapeutic agent effective to decrease expression or activity of β-catenin in a patient, thereby decreasing porphyrin production and/or accumulation, or reducing one or more symptoms of *porphyria*, such as liver injury in a patient.

Clause 2: The method of clause 1, wherein expression of β-catenin is knocked-down in the patient.

Clause 3: The method of clause 2, wherein expression of β-catenin is transiently knocked-down in the patient.

Clause 4: The method of clause 2 or 3, wherein the expression of β-catenin is decreased by an RNAi reagent.

Clause 5: The method of any of clauses 2 to 4, wherein the expression of β-catenin is decreased by an siRNA, such as a DsiRNA reagent, specific to β-catenin.

Clause 6: The method of clause 4, wherein the RNAi reagent has the sequence of any one of SEQ ID NOS: 2-21.

Clause 7: The method of clause 2, wherein expression of β-catenin is decreased by use of an antisense reagent, such as a nucleic acid or nucleic acid analog.

Clause 8: The method of clause 2, wherein expression of β-catenin is decreased by use of gene editing.

Clause 9: The method of any of clauses 1 to 8, wherein activity of β-catenin in decreased by use of an inhibitor of Wnt/β-catenin/TCF-mediated transcription.

Clause 10: The method of clause 8, wherein the inhibitor is ICG001, or an isomer or enantiomer thereof, including racemic mixtures thereof.

Clause 11: The method of clause 8, wherein the inhibitor is PRI724.

Clause 12: The method of clause 8, wherein the inhibitor of Wnt/β-catenin/TCF-mediated transcription is a PORCN inhibitor.

Clause 13: The method of clause 12, wherein the PORCN inhibitor is LGK974, CGX1321, ETC-1922159 (ETC-159), IWP2, IWP1, IWP-01, RXC004, IPW-3, IPW-4, GNF-6231, IWP-12, or IWP-L6.

Clause 14: The method of clause 12, wherein the PORCN inhibitor is Wnt-C59.

Clause 15: The method of any of clauses 1 to 14, wherein expression or activity of β-catenin in the liver of the patient is decreased.

Clause 16: The method of any of clauses 1 to 15, wherein the patient's liver is targeted for decreasing expression or activity of β-catenin.

What is claimed is:

1. A method of treating *porphyria* in a patient in need thereof, comprising: decreasing porphyrin production and/or accumulation in the patient by administering to the patient an amount of a therapeutic agent effective to decrease porphyrin production and/or accumulation in the patient, wherein the therapeutic agent is selected from the group consisting of Wnt-C59, PRI724, ICG001, an isomer, stereoisomer, or enantiomer of ICG001, and combinations thereof.

2. The method of claim 1, wherein the therapeutic agent is Wnt-C59.

3. The method of claim 1, wherein the therapeutic agent is ICG001.

4. The method of claim 3, wherein the therapeutic agent is PRI724.

5. The method of claim 1, wherein activity of β-catenin is decreased by use of the therapeutic agent.

6. The method of claim 1, wherein expression or activity of β-catenin in a liver of the patient is decreased.

7. The method of claim 1, wherein the patient's liver is targeted for decreasing porphyrin production and/or accumulation.

8. The method of claim 1, wherein the patient has one or more symptoms of *porphyria*.

9. The method of claim 8, wherein the one or more symptoms of *porphyria* is liver injury.

10. A method of decreasing porphyrin production in a patient, comprising: administering to the patient an amount of a therapeutic agent effective to decrease porphyrin production in the patient, wherein the therapeutic agent is selected from the group consisting of Wnt-C59, PRI724, ICG001 an isomer, stereoisomer, or enantiomer of ICG001, and combinations thereof.

11. The method of claim 10, wherein the therapeutic agent is Wnt-C59.

12. The method of claim 10, wherein the therapeutic agent is ICG001.

13. The method of claim 10, wherein the therapeutic agent is PRI724.

14. The method of claim 10, wherein the patient's liver is targeted for decreasing porphyrin production.

15. A method of decreasing porphyrin accumulation in a patient, comprising: administering to the patient an amount of a therapeutic agent effective to decrease porphyrin accumulation in the patient, wherein the therapeutic agent is selected from the group consisting of Wnt-C59, PRI724, ICG001 an isomer, stereoisomer, or enantiomer of ICG001, and combinations thereof.

16. The method of claim 15, wherein the therapeutic agent is Wnt-C59.

17. The method of claim 15, wherein the therapeutic agent is ICG001.

18. The method of claim 17, wherein the therapeutic agent is PRI724.

19. The method of claim 15, wherein the patient's liver is targeted for decreasing porphyrin accumulation.

* * * * *

SEQUENCE LISTING

```
<160> NUMBER OF SEQ IDS: 21

<210> SEQ ID NO 1
<211> LENGTH: 3720
<212> TYPE: PRT
<213> ORGANISM: Homo sapiens

<400> SEQUENCE: 1

Ala Gly Gly Ala Thr Ala Cys Ala Gly Cys Gly Gly Cys Thr Thr Cys
1               5                   10                  15

Thr Gly Cys Gly Cys Gly Ala Cys Thr Thr Ala Thr Ala Ala Gly Ala
                20                  25                  30

Gly Cys Thr Cys Cys Thr Thr Gly Thr Gly Cys Gly Gly Cys Gly Cys
            35                  40                  45

Cys Ala Thr Thr Thr Thr Ala Ala Gly Cys Cys Thr Cys Thr Cys Gly
        50                  55                  60

Gly Thr Cys Thr Gly Thr Gly Cys Ala Gly Cys Ala Gly Cys Gly
65                  70                  75                  80

Thr Thr Gly Gly Cys Cys Cys Gly Gly Cys Cys Cys Cys Gly Gly Gly
                85                  90                  95

Ala Gly Cys Gly Gly Ala Gly Ala Gly Cys Gly Ala Gly Gly Gly Gly
                100                 105                 110

Ala Gly Gly Cys Gly Gly Ala Gly Ala Cys Gly Gly Ala Gly Gly Ala
            115                 120                 125

Ala Gly Gly Thr Cys Thr Gly Ala Gly Gly Ala Gly Cys Ala Gly Cys
        130                 135                 140

Thr Thr Cys Ala Gly Thr Cys Cys Cys Gly Cys Cys Gly Ala Gly
145                 150                 155                 160

Cys Cys Gly Cys Cys Ala Cys Cys Gly Cys Ala Gly Gly Thr Cys Gly
                165                 170                 175

Ala Gly Gly Ala Cys Gly Gly Thr Cys Gly Gly Ala Cys Thr Cys Cys
                180                 185                 190

Cys Gly Cys Gly Gly Cys Gly Gly Ala Gly Gly Ala Gly Cys Cys
            195                 200                 205

Thr Gly Thr Thr Cys Cys Cys Thr Gly Ala Gly Gly Thr Ala
        210                 215                 220

Thr Thr Thr Gly Ala Ala Gly Thr Ala Thr Ala Cys Cys Ala Thr Ala
225                 230                 235                 240
```

-continued

Cys Ala Ala Cys Thr Gly Thr Thr Thr Thr Gly Ala Ala Ala Ala Thr
245 250 255

Cys Cys Ala Gly Cys Gly Thr Gly Gly Ala Cys Ala Ala Thr Gly Gly
260 265 270

Cys Thr Ala Cys Thr Cys Ala Ala Gly Cys Thr Gly Ala Thr Thr Thr
275 280 285

Gly Ala Thr Gly Gly Ala Gly Thr Thr Gly Gly Ala Cys Ala Thr Gly
290 295 300

Gly Cys Cys Ala Thr Gly Gly Ala Ala Cys Cys Ala Gly Ala Cys Ala
305 310 315 320

Gly Ala Ala Ala Ala Gly Cys Gly Gly Cys Thr Gly Thr Thr Ala Gly
325 330 335

Thr Cys Ala Cys Thr Gly Gly Cys Ala Gly Cys Ala Ala Cys Ala Gly
340 345 350

Thr Cys Thr Thr Ala Cys Cys Thr Gly Gly Ala Cys Thr Cys Thr Gly
355 360 365

Gly Ala Ala Thr Cys Cys Ala Thr Thr Cys Thr Gly Gly Thr Gly Cys
370 375 380

Cys Ala Cys Thr Ala Cys Cys Ala Cys Ala Gly Cys Thr Cys Cys Thr
385 390 395 400

Thr Cys Thr Cys Thr Gly Ala Gly Thr Gly Gly Thr Ala Ala Ala Gly
405 410 415

Gly Cys Ala Ala Thr Cys Cys Thr Gly Ala Gly Gly Ala Ala Gly Ala
420 425 430

Gly Gly Ala Thr Gly Thr Gly Gly Ala Thr Ala Cys Cys Thr Cys Cys
435 440 445

Cys Ala Ala Gly Thr Cys Cys Thr Gly Thr Ala Thr Gly Ala Gly Thr
450 455 460

Gly Gly Gly Ala Ala Cys Ala Gly Gly Gly Ala Thr Thr Thr Thr Cys
465 470 475 480

Thr Cys Ala Gly Thr Cys Cys Thr Thr Cys Ala Cys Thr Cys Ala Ala
485 490 495

Gly Ala Ala Cys Ala Ala Gly Thr Ala Gly Cys Thr Gly Ala Thr Ala
500 505 510

Thr Thr Gly Ala Thr Gly Gly Ala Cys Ala Gly Thr Ala Thr Gly Cys
515 520 525

Ala Ala Thr Gly Ala Cys Thr Cys Gly Ala Gly Cys Thr Cys Ala Gly
530 535 540

Ala Gly Gly Gly Thr Ala Cys Gly Ala Gly Cys Thr Gly Cys Thr Ala
545 550 555 560

Thr Gly Thr Thr Cys Cys Cys Thr Gly Ala Gly Ala Cys Ala Thr Thr
565 570 575

Ala Gly Ala Thr Gly Ala Gly Gly Gly Cys Ala Thr Gly Cys Ala Gly
580 585 590

Ala Thr Cys Cys Cys Ala Thr Cys Thr Ala Cys Ala Cys Ala Gly Thr
595 600 605

Thr Thr Gly Ala Thr Gly Cys Thr Gly Cys Thr Cys Ala Thr Cys Cys
610 615 620

Cys Ala Cys Thr Ala Ala Thr Gly Thr Cys Cys Ala Gly Cys Gly Thr
625 630 635 640

Thr Thr Gly Gly Cys Thr Gly Ala Ala Cys Cys Ala Thr Cys Ala Cys
645 650 655

-continued

```
Ala Gly Ala Thr Gly Cys Thr Gly Ala Ala Ala Cys Ala Thr Gly Cys
            660                 665                 670

Ala Gly Thr Thr Gly Thr Ala Ala Ala Cys Thr Thr Gly Ala Thr Thr
        675                 680                 685

Ala Ala Cys Thr Ala Thr Cys Ala Ala Gly Ala Thr Gly Ala Thr Gly
    690                 695                 700

Cys Ala Gly Ala Ala Cys Thr Thr Gly Cys Cys Ala Cys Ala Cys Gly
705                 710                 715                 720

Thr Gly Cys Ala Ala Thr Cys Cys Cys Thr Gly Ala Ala Cys Thr Gly
                725                 730                 735

Ala Cys Ala Ala Ala Ala Cys Thr Gly Cys Thr Ala Ala Ala Thr Gly
            740                 745                 750

Ala Cys Gly Ala Gly Gly Ala Cys Cys Ala Gly Gly Thr Gly Gly Thr
        755                 760                 765

Gly Gly Thr Thr Ala Ala Thr Ala Ala Gly Gly Cys Thr Gly Cys Ala
    770                 775                 780

Gly Thr Thr Ala Thr Gly Gly Thr Cys Cys Ala Thr Cys Ala Gly Cys
785                 790                 795                 800

Thr Thr Thr Cys Thr Ala Ala Ala Ala Ala Gly Gly Ala Ala Gly Cys
                805                 810                 815

Thr Thr Cys Cys Ala Gly Ala Cys Ala Cys Gly Cys Thr Ala Thr Cys
            820                 825                 830

Ala Thr Gly Cys Gly Thr Thr Cys Thr Cys Cys Thr Cys Ala Gly Ala
        835                 840                 845

Thr Gly Gly Thr Gly Thr Cys Thr Gly Cys Thr Ala Thr Thr Gly Thr
    850                 855                 860

Ala Cys Gly Thr Ala Cys Cys Ala Thr Gly Cys Ala Gly Ala Ala Thr
865                 870                 875                 880

Ala Cys Ala Ala Ala Thr Gly Ala Thr Gly Thr Ala Gly Ala Ala Ala
                885                 890                 895

Cys Ala Gly Cys Thr Cys Gly Thr Thr Gly Thr Ala Cys Cys Gly Cys
            900                 905                 910

Thr Gly Gly Gly Ala Cys Cys Thr Thr Gly Cys Ala Thr Ala Ala Cys
        915                 920                 925

Cys Thr Thr Thr Cys Cys Cys Ala Thr Cys Ala Thr Cys Gly Thr Gly
    930                 935                 940

Ala Gly Gly Gly Cys Thr Thr Ala Cys Thr Gly Gly Cys Cys Ala Thr
945                 950                 955                 960

Cys Thr Thr Thr Ala Ala Gly Thr Cys Thr Gly Gly Ala Gly Gly Cys
                965                 970                 975

Ala Thr Thr Cys Cys Thr Gly Cys Cys Cys Thr Gly Gly Thr Gly Ala
            980                 985                 990

Ala Ala Ala Thr Gly Cys Thr Thr  Gly Gly Thr Thr Cys  Ala Cys Cys
        995                 1000                 1005

Ala Gly  Thr Gly Gly Ala Thr  Thr Cys Thr Gly Thr  Gly Thr Thr
    1010                 1015                 1020

Gly Thr  Thr Thr Thr Ala Thr  Gly Cys Cys Ala Thr  Thr Ala Cys
    1025                 1030                 1035

Ala Ala  Cys Thr Cys Thr Cys  Cys Ala Cys Ala Ala  Cys Cys Thr
    1040                 1045                 1050

Thr Thr  Thr Ala Thr Thr Ala  Cys Ala Thr Cys Ala  Ala Gly Ala
    1055                 1060                 1065

Ala Gly  Gly Ala Gly Cys Thr  Ala Ala Ala Ala Thr  Gly Gly Cys
```

-continued

```
1070 1075 1080

Ala Gly Thr Gly Cys Gly Thr Thr Thr Ala Gly Cys Thr Gly Gly
1085 1090 1095

Thr Gly Gly Gly Cys Thr Gly Cys Ala Gly Ala Ala Ala Ala Thr
1100 1105 1110

Gly Gly Thr Thr Gly Cys Cys Thr Thr Gly Cys Thr Cys Ala Ala
1115 1120 1125

Cys Ala Ala Ala Ala Cys Ala Ala Ala Thr Gly Thr Thr Ala Ala
1130 1135 1140

Ala Thr Thr Cys Thr Thr Gly Gly Cys Thr Ala Thr Thr Ala Cys
1145 1150 1155

Gly Ala Cys Ala Gly Ala Cys Thr Gly Cys Cys Thr Thr Cys Ala
1160 1165 1170

Ala Ala Thr Thr Thr Thr Ala Gly Cys Thr Thr Ala Thr Gly Gly
1175 1180 1185

Cys Ala Ala Cys Cys Ala Ala Gly Ala Ala Ala Gly Cys Ala Ala
1190 1195 1200

Gly Cys Thr Cys Ala Thr Cys Ala Thr Ala Cys Thr Gly Gly Cys
1205 1210 1215

Thr Ala Gly Thr Gly Gly Thr Gly Gly Ala Cys Cys Cys Cys Ala
1220 1225 1230

Ala Gly Cys Thr Thr Thr Ala Gly Thr Ala Ala Ala Thr Ala Thr
1235 1240 1245

Ala Ala Thr Gly Ala Gly Gly Ala Cys Cys Thr Ala Thr Ala Cys
1250 1255 1260

Thr Thr Ala Cys Gly Ala Ala Ala Ala Ala Cys Thr Ala Cys Thr
1265 1270 1275

Gly Thr Gly Gly Ala Cys Cys Ala Cys Ala Ala Gly Cys Ala Gly
1280 1285 1290

Ala Gly Thr Gly Cys Thr Gly Ala Ala Gly Gly Thr Gly Cys Thr
1295 1300 1305

Ala Thr Cys Thr Gly Thr Cys Thr Gly Cys Thr Cys Thr Ala Gly
1310 1315 1320

Thr Ala Ala Thr Ala Ala Gly Cys Cys Gly Gly Cys Thr Ala Thr
1325 1330 1335

Thr Gly Thr Ala Gly Ala Ala Gly Cys Thr Gly Gly Thr Gly Gly
1340 1345 1350

Ala Ala Thr Gly Cys Ala Ala Gly Cys Thr Thr Thr Ala Gly Gly
1355 1360 1365

Ala Cys Thr Thr Cys Ala Cys Cys Thr Gly Ala Cys Ala Gly Ala
1370 1375 1380

Thr Cys Cys Ala Ala Gly Thr Cys Ala Ala Cys Gly Thr Cys Thr
1385 1390 1395

Thr Gly Thr Thr Cys Ala Gly Ala Ala Cys Thr Gly Thr Cys Thr
1400 1405 1410

Thr Thr Gly Gly Ala Cys Thr Cys Thr Cys Ala Gly Gly Ala Ala
1415 1420 1425

Thr Cys Thr Thr Thr Cys Ala Gly Ala Thr Gly Cys Thr Gly Cys
1430 1435 1440

Ala Ala Cys Thr Ala Ala Ala Cys Ala Gly Gly Ala Ala Gly Gly
1445 1450 1455

Gly Ala Thr Gly Gly Ala Ala Gly Gly Thr Cys Thr Cys Cys Thr
1460 1465 1470
```

-continued

```
Thr Gly  Gly Gly Ala Cys Thr  Cys Thr Thr Gly Thr  Thr Cys Ala
    1475                 1480                 1485

Gly Cys  Thr Thr Cys Thr Gly  Gly Gly Thr Thr Cys  Ala Gly Ala
    1490                 1495                 1500

Thr Gly  Ala Thr Ala Thr Ala  Ala Ala Thr Gly Thr  Gly Gly Thr
    1505                 1510                 1515

Cys Ala  Cys Cys Thr Gly Thr  Gly Cys Ala Gly Cys  Thr Gly Gly
    1520                 1525                 1530

Ala Ala  Thr Thr Cys Thr Thr  Thr Cys Thr Ala Ala  Cys Cys Thr
    1535                 1540                 1545

Cys Ala  Cys Thr Thr Gly Cys  Ala Ala Thr Ala Ala  Thr Thr Ala
    1550                 1555                 1560

Thr Ala  Ala Gly Ala Ala Cys  Ala Ala Gly Ala Thr  Gly Ala Thr
    1565                 1570                 1575

Gly Gly  Thr Cys Thr Gly Cys  Cys Ala Ala Gly Thr  Gly Gly Gly
    1580                 1585                 1590

Thr Gly  Gly Thr Ala Thr Ala  Gly Ala Gly Gly Cys  Thr Cys Thr
    1595                 1600                 1605

Thr Gly  Thr Gly Cys Gly Thr  Ala Cys Thr Gly Thr  Cys Cys Thr
    1610                 1615                 1620

Thr Cys  Gly Gly Gly Cys Thr  Gly Gly Thr Gly Ala  Cys Ala Gly
    1625                 1630                 1635

Gly Gly  Ala Ala Gly Ala Cys  Ala Thr Cys Ala Cys  Thr Gly Ala
    1640                 1645                 1650

Gly Cys  Cys Thr Gly Cys Cys  Ala Thr Cys Thr Gly  Thr Gly Cys
    1655                 1660                 1665

Thr Cys  Thr Thr Cys Gly Thr  Cys Ala Thr Cys Thr  Gly Ala Cys
    1670                 1675                 1680

Cys Ala  Gly Cys Cys Gly Ala  Cys Ala Cys Cys Ala  Ala Gly Ala
    1685                 1690                 1695

Ala Gly  Cys Ala Gly Ala Gly  Ala Thr Gly Gly Cys  Cys Cys Ala
    1700                 1705                 1710

Gly Ala  Ala Thr Gly Cys Ala  Gly Thr Thr Cys Gly  Cys Cys Thr
    1715                 1720                 1725

Thr Cys  Ala Cys Thr Ala Thr  Gly Gly Ala Cys Thr  Ala Cys Cys
    1730                 1735                 1740

Ala Gly  Thr Thr Gly Thr Gly  Gly Thr Thr Ala Ala  Gly Cys Thr
    1745                 1750                 1755

Cys Thr  Thr Ala Cys Ala Cys  Cys Cys Ala Cys Cys  Ala Thr Cys
    1760                 1765                 1770

Cys Cys  Ala Cys Thr Gly Gly  Cys Cys Thr Cys Thr  Gly Ala Thr
    1775                 1780                 1785

Ala Ala  Ala Gly Gly Cys Thr  Ala Cys Thr Gly Thr  Thr Gly Gly
    1790                 1795                 1800

Ala Thr  Thr Gly Ala Thr Thr  Cys Gly Ala Ala Ala  Thr Cys Thr
    1805                 1810                 1815

Thr Gly  Cys Cys Cys Thr Thr  Thr Gly Thr Cys Cys  Cys Gly Cys
    1820                 1825                 1830

Ala Ala  Ala Thr Cys Ala Thr  Gly Cys Ala Cys Cys  Thr Thr Thr
    1835                 1840                 1845

Gly Cys  Gly Thr Gly Ala Gly  Cys Ala Gly Gly Gly  Thr Gly Cys
    1850                 1855                 1860
```

-continued

```
Cys Ala  Thr Thr Cys Cys Ala  Cys Gly Ala Cys Thr  Ala Gly Thr
    1865                 1870                 1875

Thr Cys  Ala Gly Thr Thr Gly  Cys Thr Thr Gly Thr  Thr Cys Gly
    1880                 1885                 1890

Thr Gly  Cys Ala Cys Ala Thr  Cys Ala Gly Gly Ala  Thr Ala Cys
    1895                 1900                 1905

Cys Cys  Ala Gly Cys Gly Cys  Cys Gly Thr Ala Cys  Gly Thr Cys
    1910                 1915                 1920

Cys Ala  Thr Gly Gly Gly Thr  Gly Gly Gly Ala Cys  Ala Cys Ala
    1925                 1930                 1935

Gly Cys  Ala Gly Cys Ala Ala  Thr Thr Thr Gly Thr  Gly Gly Ala
    1940                 1945                 1950

Gly Gly  Gly Gly Gly Thr Cys  Cys Gly Cys Ala Thr  Gly Gly Ala
    1955                 1960                 1965

Ala Gly  Ala Ala Ala Thr Ala  Gly Thr Thr Gly Ala  Ala Gly Gly
    1970                 1975                 1980

Thr Thr  Gly Thr Ala Cys Cys  Gly Gly Ala Gly Cys  Cys Cys Thr
    1985                 1990                 1995

Thr Cys  Ala Cys Ala Thr Cys  Cys Thr Ala Gly Cys  Thr Cys Gly
    2000                 2005                 2010

Gly Gly  Ala Thr Gly Thr Thr  Cys Ala Cys Ala Ala  Cys Cys Gly
    2015                 2020                 2025

Ala Ala  Thr Thr Gly Thr Thr  Ala Thr Cys Ala Gly  Ala Gly Gly
    2030                 2035                 2040

Ala Cys  Thr Ala Ala Ala Thr  Ala Cys Cys Ala Thr  Thr Cys Cys
    2045                 2050                 2055

Ala Thr  Thr Gly Thr Thr Thr  Gly Thr Gly Cys Ala  Gly Cys Thr
    2060                 2065                 2070

Gly Cys  Thr Thr Thr Ala Thr  Thr Cys Thr Cys Cys  Cys Ala Thr
    2075                 2080                 2085

Thr Gly  Ala Ala Ala Ala Cys  Ala Thr Cys Cys Ala  Ala Ala Gly
    2090                 2095                 2100

Ala Gly  Thr Ala Gly Cys Thr  Gly Cys Ala Gly Gly  Gly Gly Thr
    2105                 2110                 2115

Cys Cys  Thr Cys Thr Gly Thr  Gly Ala Ala Cys Thr  Thr Gly Cys
    2120                 2125                 2130

Thr Cys  Ala Gly Gly Ala Cys  Ala Ala Gly Gly Ala  Ala Gly Cys
    2135                 2140                 2145

Thr Gly  Cys Ala Gly Ala Ala  Gly Cys Thr Ala Thr  Thr Gly Ala
    2150                 2155                 2160

Ala Gly  Cys Thr Gly Ala Gly  Gly Gly Ala Gly Cys  Cys Ala Cys
    2165                 2170                 2175

Ala Gly  Cys Thr Cys Cys Thr  Cys Thr Gly Ala Cys  Ala Gly Ala
    2180                 2185                 2190

Gly Thr  Thr Ala Cys Thr Thr  Cys Ala Cys Thr Cys  Thr Ala Gly
    2195                 2200                 2205

Gly Ala  Ala Thr Gly Ala Ala  Gly Gly Thr Gly Thr  Gly Gly Cys
    2210                 2215                 2220

Gly Ala  Cys Ala Thr Ala Thr  Gly Cys Ala Gly Cys  Thr Gly Cys
    2225                 2230                 2235

Thr Gly  Thr Thr Thr Thr Gly  Thr Thr Cys Cys Gly  Ala Ala Thr
    2240                 2245                 2250

Gly Thr  Cys Thr Gly Ala Gly  Gly Ala Cys Ala Ala  Gly Cys Cys
```

-continued

|      | 2255 |      |      | 2260 |      |      |      | 2265 |      |      |      |
|------|------|------|------|------|------|------|------|------|------|------|------|
| Ala  | Cys  | Ala  | Ala  | Gly  | Ala  | Thr  | Thr  | Ala  | Cys  | Ala  | Ala  | Gly | Ala | Ala |

Ala Cys Ala Ala Gly Ala Thr Thr Ala Cys Ala Ala Gly Ala Ala
2270                2275                2280

Ala Cys Gly Gly Cys Thr Thr Thr Cys Ala Gly Thr Thr Gly Ala
2285                2290                2295

Gly Cys Thr Gly Ala Cys Cys Ala Gly Cys Thr Cys Thr Cys Thr
2300                2305                2310

Cys Thr Thr Cys Ala Gly Ala Ala Cys Ala Gly Ala Gly Cys Cys
2315                2320                2325

Ala Ala Thr Gly Gly Cys Thr Gly Gly Ala Ala Thr Gly Ala
2330                2335                2340

Gly Ala Cys Thr Gly Cys Thr Gly Ala Thr Cys Thr Thr Gly Gly
2345                2350                2355

Ala Cys Thr Thr Gly Ala Thr Ala Thr Thr Gly Gly Thr Gly Cys
2360                2365                2370

Cys Cys Ala Gly Gly Gly Ala Gly Ala Ala Cys Cys Cys Cys Thr
2375                2380                2385

Thr Gly Gly Ala Thr Ala Thr Cys Gly Cys Cys Ala Gly Gly Ala
2390                2395                2400

Thr Gly Ala Thr Cys Cys Thr Ala Gly Cys Thr Ala Thr Cys Gly
2405                2410                2415

Thr Thr Cys Thr Thr Thr Thr Cys Ala Cys Thr Cys Thr Gly Gly
2420                2425                2430

Thr Gly Gly Ala Thr Ala Thr Gly Gly Cys Cys Ala Gly Gly Ala
2435                2440                2445

Thr Gly Cys Cys Thr Thr Gly Gly Gly Thr Ala Thr Gly Gly Ala
2450                2455                2460

Cys Cys Cys Cys Ala Thr Gly Ala Thr Gly Gly Ala Ala Cys Ala
2465                2470                2475

Thr Gly Ala Gly Ala Thr Gly Gly Gly Thr Gly Gly Cys Cys Ala
2480                2485                2490

Cys Cys Ala Cys Cys Cys Thr Gly Gly Thr Gly Cys Thr Gly Ala
2495                2500                2505

Cys Thr Ala Thr Cys Cys Ala Gly Thr Thr Gly Ala Thr Gly Gly
2510                2515                2520

Gly Cys Thr Gly Cys Cys Ala Gly Ala Thr Cys Thr Gly Gly Gly
2525                2530                2535

Gly Cys Ala Thr Gly Cys Cys Ala Gly Gly Ala Cys Cys Thr
2540                2545                2550

Cys Ala Thr Gly Gly Ala Thr Gly Gly Gly Cys Thr Gly Cys Cys
2555                2560                2565

Thr Cys Cys Ala Gly Gly Thr Gly Ala Cys Ala Gly Cys Ala Ala
2570                2575                2580

Thr Cys Ala Gly Cys Thr Gly Gly Cys Cys Thr Gly Gly Thr Thr
2585                2590                2595

Thr Gly Ala Thr Ala Cys Thr Gly Ala Cys Cys Thr Gly Thr Ala
2600                2605                2610

Ala Ala Thr Cys Ala Thr Cys Cys Thr Thr Thr Ala Gly Gly Thr
2615                2620                2625

Ala Ala Gly Ala Ala Gly Thr Thr Thr Ala Ala Ala Ala Ala
2630                2635                2640

Gly Cys Cys Ala Gly Thr Thr Thr Gly Gly Gly Thr Ala Ala Ala
2645                2650                2655

-continued

Ala Thr Ala Cys Thr Thr Thr Thr Ala Cys Thr Cys Thr Gly Cys
2660 2665 2670

Cys Thr Ala Cys Ala Gly Ala Ala Cys Thr Thr Cys Ala Gly Ala
2675 2680 2685

Ala Ala Gly Ala Cys Thr Thr Gly Gly Thr Thr Gly Gly Thr Ala
2690 2695 2700

Gly Gly Gly Thr Gly Gly Gly Ala Gly Thr Gly Gly Thr Thr Thr
2705 2710 2715

Ala Gly Gly Cys Thr Ala Thr Thr Thr Gly Thr Ala Ala Ala Thr
2720 2725 2730

Cys Thr Gly Cys Cys Ala Cys Ala Ala Ala Ala Ala Cys Ala Gly
2735 2740 2745

Gly Thr Ala Thr Ala Thr Ala Cys Thr Thr Thr Gly Ala Ala Ala
2750 2755 2760

Gly Gly Ala Gly Ala Thr Gly Thr Cys Thr Thr Gly Gly Ala Ala
2765 2770 2775

Cys Ala Thr Thr Gly Gly Ala Ala Thr Gly Thr Thr Cys Thr Cys
2780 2785 2790

Ala Gly Ala Thr Thr Thr Cys Thr Gly Gly Thr Thr Gly Thr Thr
2795 2800 2805

Ala Thr Gly Thr Gly Ala Thr Cys Ala Thr Gly Thr Gly Thr Gly
2810 2815 2820

Gly Ala Ala Gly Thr Thr Ala Thr Thr Ala Ala Cys Thr Thr Thr
2825 2830 2835

Ala Ala Thr Gly Thr Thr Thr Thr Thr Thr Gly Cys Cys Ala Cys
2840 2845 2850

Ala Gly Cys Thr Thr Thr Thr Gly Cys Ala Ala Cys Thr Thr Ala
2855 2860 2865

Ala Thr Ala Cys Thr Cys Ala Ala Ala Thr Gly Ala Gly Thr Ala
2870 2875 2880

Ala Cys Ala Thr Thr Thr Gly Cys Thr Gly Thr Thr Thr Thr Ala
2885 2890 2895

Ala Ala Cys Ala Thr Thr Ala Ala Thr Ala Gly Cys Ala Gly Cys
2900 2905 2910

Cys Thr Thr Thr Cys Thr Cys Thr Cys Thr Thr Thr Ala Thr Ala
2915 2920 2925

Cys Ala Gly Cys Thr Gly Thr Ala Thr Thr Gly Thr Cys Thr Gly
2930 2935 2940

Ala Ala Cys Thr Thr Gly Cys Ala Thr Thr Gly Thr Gly Ala Thr
2945 2950 2955

Thr Gly Gly Cys Cys Thr Gly Thr Ala Gly Ala Gly Thr Thr Gly
2960 2965 2970

Cys Thr Gly Ala Gly Ala Gly Gly Gly Cys Thr Cys Gly Ala Gly
2975 2980 2985

Gly Gly Gly Thr Gly Gly Gly Cys Thr Gly Gly Thr Ala Thr Cys
2990 2995 3000

Thr Cys Ala Gly Ala Ala Ala Gly Thr Gly Cys Cys Thr Gly Ala
3005 3010 3015

Cys Ala Cys Ala Cys Thr Ala Ala Cys Cys Ala Ala Gly Cys Thr
3020 3025 3030

Gly Ala Gly Thr Thr Thr Cys Cys Thr Ala Thr Gly Gly Gly Ala
3035 3040 3045

```
Ala Cys Ala Ala Thr Thr Gly Ala Ala Gly Thr Ala  Ala Ala Cys
    3050                3055               3060

Thr Thr Thr Thr Thr Gly Thr Thr Cys Thr Gly Gly  Thr Cys Cys
    3065                3070               3075

Thr Thr Thr Thr Thr Gly Gly Thr Cys Gly Ala Gly  Gly Ala Gly
    3080                3085               3090

Thr Ala Ala Cys Ala Ala Thr Ala Cys Ala Ala Ala  Thr Gly Gly
    3095                3100               3105

Ala Thr Thr Thr Thr Gly Gly Gly Ala Gly Thr Gly  Ala Cys Thr
    3110                3115               3120

Cys Ala Ala Gly Ala Ala Gly Thr Gly Ala Ala Gly  Ala Ala Thr
    3125                3130               3135

Gly Cys Ala Cys Ala Ala Gly Ala Ala Thr Gly Gly  Ala Thr Cys
    3140                3145               3150

Ala Cys Ala Ala Gly Ala Thr Gly Gly Ala Ala Thr  Thr Thr Ala
    3155                3160               3165

Thr Cys Ala Ala Ala Cys Cys Cys Thr Ala Gly Cys  Cys Thr Thr
    3170                3175               3180

Gly Cys Thr Thr Gly Thr Thr Ala Ala Ala Thr Thr  Thr Thr Thr
    3185                3190               3195

Thr Thr Thr Thr Thr Thr Thr Thr Thr Thr Thr Thr  Thr Thr Ala
    3200                3205               3210

Ala Gly Ala Ala Thr Ala Thr Cys Thr Gly Thr Ala  Ala Thr Gly
    3215                3220               3225

Gly Thr Ala Cys Thr Gly Ala Cys Thr Thr Thr Gly  Cys Thr Thr
    3230                3235               3240

Gly Cys Thr Thr Thr Gly Ala Ala Gly Thr Ala Gly  Cys Thr Cys
    3245                3250               3255

Thr Thr Thr Thr Thr Thr Thr Thr Thr Thr Thr Thr  Thr Thr Thr
    3260                3265               3270

Thr Thr Thr Thr Thr Thr Thr Thr Thr Thr Gly Cys  Ala Gly Thr
    3275                3280               3285

Ala Ala Cys Thr Gly Thr Thr Thr Thr Thr Thr Ala  Ala Gly Thr
    3290                3295               3300

Cys Thr Cys Thr Cys Gly Thr Ala Gly Thr Gly Thr  Thr Ala Ala
    3305                3310               3315

Gly Thr Thr Ala Thr Ala Gly Thr Gly Ala Ala Thr  Ala Cys Thr
    3320                3325               3330

Gly Cys Thr Ala Cys Ala Gly Cys Ala Ala Thr Thr  Thr Cys Thr
    3335                3340               3345

Ala Ala Thr Thr Thr Thr Thr Ala Ala Gly Ala Ala  Thr Thr Gly
    3350                3355               3360

Ala Gly Thr Ala Ala Thr Gly Gly Thr Gly Thr Ala  Gly Ala Ala
    3365                3370               3375

Cys Ala Cys Thr Ala Ala Thr Thr Cys Ala Thr Ala  Ala Thr Cys
    3380                3385               3390

Ala Cys Thr Cys Thr Ala Ala Thr Thr Ala Ala Thr  Thr Gly Thr
    3395                3400               3405

Ala Ala Thr Cys Thr Gly Ala Ala Thr Ala Ala Ala  Gly Thr Gly
    3410                3415               3420

Thr Ala Ala Cys Ala Ala Thr Gly Thr Gly Thr Ala  Gly Ala Cys
    3425                3430               3435

Cys Thr Thr Thr Thr Thr Gly Thr Ala Thr Ala Ala  Ala Ala Thr
```

Ala Gly Ala Cys Ala Ala Ala Thr Ala Gly Ala Ala Ala Ala Thr
            3455                3460                3465

Gly Gly Thr Cys Cys Ala Ala Thr Thr Ala Gly Thr Thr Thr Cys
            3470                3475                3480

Cys Thr Thr Thr Thr Thr Ala Ala Thr Ala Thr Gly Cys Thr Thr
            3485                3490                3495

Ala Ala Ala Ala Thr Ala Ala Gly Cys Ala Gly Gly Thr Gly Gly
            3500                3505                3510

Ala Thr Cys Thr Ala Thr Thr Cys Ala Thr Gly Thr Thr Thr
            3515                3520                3525

Thr Thr Gly Ala Thr Cys Ala Ala Ala Ala Cys Thr Ala Thr
            3530                3535                3540

Thr Thr Gly Gly Gly Ala Thr Ala Thr Gly Thr Ala Thr Gly Gly
            3545                3550                3555

Gly Thr Ala Gly Gly Gly Thr Ala Ala Ala Thr Cys Ala Gly Thr
            3560                3565                3570

Ala Ala Gly Ala Gly Gly Thr Gly Thr Thr Ala Thr Thr Thr Gly
            3575                3580                3585

Gly Ala Ala Cys Cys Thr Thr Gly Thr Thr Thr Thr Gly Gly Ala
            3590                3595                3600

Cys Ala Gly Thr Thr Thr Ala Cys Cys Ala Gly Thr Thr Gly Cys
            3605                3610                3615

Cys Thr Thr Thr Thr Ala Thr Cys Cys Cys Ala Ala Ala Gly Thr
            3620                3625                3630

Thr Gly Thr Thr Gly Thr Ala Ala Cys Cys Thr Gly Cys Thr Gly
            3635                3640                3645

Thr Gly Ala Thr Ala Cys Gly Ala Thr Gly Cys Thr Thr Cys Ala
            3650                3655                3660

Ala Gly Ala Gly Ala Ala Ala Ala Thr Gly Cys Gly Gly Thr Thr
            3665                3670                3675

Ala Thr Ala Ala Ala Ala Ala Thr Gly Gly Thr Thr Cys Ala
            3680                3685                3690

Gly Ala Ala Thr Thr Ala Ala Ala Cys Thr Thr Thr Thr Ala Ala
            3695                3700                3705

Thr Thr Cys Ala Thr Thr Cys Gly Ala Thr Thr Gly
            3710                3715                3720

<210> SEQ ID NO 2
<211> LENGTH: 27
<212> TYPE: DNA
<213> ORGANISM: Artificial Sequence
<220> FEATURE:
<223> OTHER INFORMATION: DsiRNA

<400> SEQUENCE: 2
cagggatttt ctcagtcctt cactcaa                                       27

<210> SEQ ID NO 3
<211> LENGTH: 27
<212> TYPE: DNA
<213> ORGANISM: Artificial Sequence
<220> FEATURE:
<223> OTHER INFORMATION: DsiRNA

<400> SEQUENCE: 3
tgatggacag tatgcaatga ctcgagc                                       27

```
<210> SEQ ID NO 4
<211> LENGTH: 27
<212> TYPE: DNA
<213> ORGANISM: Artificial Sequence
<220> FEATURE:
<223> OTHER INFORMATION: DsiRNA

<400> SEQUENCE: 4
tgctgctcat cccactaatg tccagcg                                       27

<210> SEQ ID NO 5
<211> LENGTH: 27
<212> TYPE: DNA
<213> ORGANISM: Artificial Sequence
<220> FEATURE:
<223> OTHER INFORMATION: DsiRNA

<400> SEQUENCE: 5
gcagaataca aatgatgtag aaacagc                                       27

<210> SEQ ID NO 6
<211> LENGTH: 27
<212> TYPE: DNA
<213> ORGANISM: Artificial Sequence
<220> FEATURE:
<223> OTHER INFORMATION: DsiRNA

<400> SEQUENCE: 6
cacctgtgca gctggaattc tttctaa                                       27

<210> SEQ ID NO 7
<211> LENGTH: 27
<212> TYPE: DNA
<213> ORGANISM: Artificial Sequence
<220> FEATURE:
<223> OTHER INFORMATION: DsiRNA

<400> SEQUENCE: 7
tgaacttgct caggacaagg aagctgc                                       27

<210> SEQ ID NO 8
<211> LENGTH: 27
<212> TYPE: DNA
<213> ORGANISM: Artificial Sequence
<220> FEATURE:
<223> OTHER INFORMATION: DsiRNA

<400> SEQUENCE: 8
tagccttgct tgttaaattt ttttttt                                       27

<210> SEQ ID NO 9
<211> LENGTH: 27
<212> TYPE: DNA
<213> ORGANISM: Artificial Sequence
<220> FEATURE:
<223> OTHER INFORMATION: DsiRNA

<400> SEQUENCE: 9
gtagaacact aattcataat cactcta                                       27

<210> SEQ ID NO 10
<211> LENGTH: 27
<212> TYPE: DNA
<213> ORGANISM: Artificial Sequence
<220> FEATURE:
```

```
<223> OTHER INFORMATION: DsiRNA

<400> SEQUENCE: 10
taaatcagta agaggtgtta tttggaa                                          27

<210> SEQ ID NO 11
<211> LENGTH: 27
<212> TYPE: DNA
<213> ORGANISM: Artificial Sequence
<220> FEATURE:
<223> OTHER INFORMATION: DsiRNA

<400> SEQUENCE: 11
aaaaatggtt cagaattaaa cttttaa                                          27

<210> SEQ ID NO 12
<211> LENGTH: 21
<212> TYPE: DNA
<213> ORGANISM: Artificial Sequence
<220> FEATURE:
<223> OTHER INFORMATION: DsiRNA

<400> SEQUENCE: 12
cagggatttt ctcagtcctt c                                                21

<210> SEQ ID NO 13
<211> LENGTH: 21
<212> TYPE: DNA
<213> ORGANISM: Artificial Sequence
<220> FEATURE:
<223> OTHER INFORMATION: DsiRNA

<400> SEQUENCE: 13
tgatggacag tatgcaatga c                                                21

<210> SEQ ID NO 14
<211> LENGTH: 21
<212> TYPE: DNA
<213> ORGANISM: Artificial Sequence
<220> FEATURE:
<223> OTHER INFORMATION: DsiRNA

<400> SEQUENCE: 14
tgctgctcat cccactaatg t                                                21

<210> SEQ ID NO 15
<211> LENGTH: 21
<212> TYPE: DNA
<213> ORGANISM: Artificial Sequence
<220> FEATURE:
<223> OTHER INFORMATION: DsiRNA

<400> SEQUENCE: 15
gcagaataca aatgatgtag a                                                21

<210> SEQ ID NO 16
<211> LENGTH: 21
<212> TYPE: DNA
<213> ORGANISM: Artificial Sequence
<220> FEATURE:
<223> OTHER INFORMATION: DsiRNA

<400> SEQUENCE: 16
cacctgtgca gctggaattc t                                                21
```

```
<210> SEQ ID NO 17
<211> LENGTH: 21
<212> TYPE: DNA
<213> ORGANISM: Artificial Sequence
<220> FEATURE:
<223> OTHER INFORMATION: DsiRNA

<400> SEQUENCE: 17
tgaacttgct caggacaagg a                                              21

<210> SEQ ID NO 18
<211> LENGTH: 21
<212> TYPE: DNA
<213> ORGANISM: Artificial Sequence
<220> FEATURE:
<223> OTHER INFORMATION: DsiRNA

<400> SEQUENCE: 18
tagccttgct tgttaaattt t                                              21

<210> SEQ ID NO 19
<211> LENGTH: 21
<212> TYPE: DNA
<213> ORGANISM: Artificial Sequence
<220> FEATURE:
<223> OTHER INFORMATION: DsiRNA

<400> SEQUENCE: 19
gtagaacact aattcataat c                                              21

<210> SEQ ID NO 20
<211> LENGTH: 21
<212> TYPE: DNA
<213> ORGANISM: Artificial Sequence
<220> FEATURE:
<223> OTHER INFORMATION: DsiRNA

<400> SEQUENCE: 20
taaatcagta agaggtgtta t                                              21

<210> SEQ ID NO 21
<211> LENGTH: 21
<212> TYPE: DNA
<213> ORGANISM: Artificial Sequence
<220> FEATURE:
<223> OTHER INFORMATION: DsiRNA

<400> SEQUENCE: 21
aaaaatggtt cagaattaaa c                                              21
```

UNITED STATES PATENT AND TRADEMARK OFFICE
CERTIFICATE OF CORRECTION

PATENT NO. : 12,180,474 B2
APPLICATION NO. : 17/194706
DATED : December 31, 2024
INVENTOR(S) : Satdarshan Monga et al.

Page 1 of 1

It is certified that error appears in the above-identified patent and that said Letters Patent is hereby corrected as shown below:

On the Title Page

Column 2, item [56] Other Publications, Line 42, delete "Poren" and insert -- Porcn --

In the Claims

Column 47, Line 66, Claim 4, delete "3," and insert -- 1, --

Column 49, Line 2, Claim 10, delete "ICG001" and insert -- ICG001, --

Column 49, Line 17, Claim 15, delete "ICG001" and insert -- ICG001, --

Column 49, Line 23, Claim 18, delete "17," and insert -- 15, --

Signed and Sealed this
Fourth Day of March, 2025

Coke Morgan Stewart
*Acting Director of the United States Patent and Trademark Office*